(12) United States Patent
Stoessel et al.

(10) Patent No.: US 9,481,826 B2
(45) Date of Patent: Nov. 1, 2016

(54) ELECTRONIC DEVICE COMPRISING METAL COMPLEXES

(75) Inventors: Philipp Stoessel, Frankfurt am Main (DE); Esther Breuning, Ober-Ramstadt (DE)

(73) Assignee: Merck Patent GmbH (DE)

( * ) Notice: Subject to any disclaimer, the term of this patent is extended or adjusted under 35 U.S.C. 154(b) by 1363 days.

(21) Appl. No.: 12/996,257

(22) PCT Filed: May 7, 2009

(86) PCT No.: PCT/EP2009/003277
§ 371 (c)(1),
(2), (4) Date: Dec. 3, 2010

(87) PCT Pub. No.: WO2009/146770
PCT Pub. Date: Dec. 10, 2009

(65) Prior Publication Data
US 2011/0089410 A1    Apr. 21, 2011

(30) Foreign Application Priority Data

Jun. 5, 2008 (DE) .................. 10 2008 027 005

(51) Int. Cl.
| | |
|---|---|
| H01L 51/00 | (2006.01) |
| H01L 51/54 | (2006.01) |
| C09K 11/06 | (2006.01) |
| C07F 1/00 | (2006.01) |
| C07F 11/00 | (2006.01) |
| C07F 15/00 | (2006.01) |
| C09B 57/10 | (2006.01) |
| H01L 51/50 | (2006.01) |
| H05B 33/14 | (2006.01) |

(52) U.S. Cl.
CPC ............ *C09K 11/06* (2013.01); *C07F 1/005* (2013.01); *C07F 11/005* (2013.01); *C07F 15/0033* (2013.01); *C09B 57/10* (2013.01); *H01L 51/0081* (2013.01); *H01L 51/0084* (2013.01); *H01L 51/0085* (2013.01); *H01L 51/0086* (2013.01); *H01L 51/0087* (2013.01); *H01L 51/0088* (2013.01); *H01L 51/0091* (2013.01); *H01L 51/5016* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1051* (2013.01); *C09K 2211/1055* (2013.01); *C09K 2211/1059* (2013.01); *C09K 2211/1092* (2013.01); *C09K 2211/182* (2013.01); *C09K 2211/183* (2013.01); *C09K 2211/185* (2013.01); *C09K 2211/186* (2013.01); *C09K 2211/188* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,621,131 A | 4/1997 | Kreuder et al. | |
| 5,679,760 A | 10/1997 | Mullen et al. | |
| 5,840,217 A | 11/1998 | Lupo et al. | |
| 6,458,909 B1 | 10/2002 | Spreitzer et al. | |
| 6,605,317 B1 | 8/2003 | Kathirgamanathan | |
| 6,653,438 B1 | 11/2003 | Spreitzer et al. | |
| 7,084,273 B2 | 8/2006 | Stossel et al. | |
| 7,179,915 B2 | 2/2007 | Stossel et al. | |
| 7,345,301 B2 | 3/2008 | Gerhard et al. | |
| 7,423,151 B2 | 9/2008 | Stossel et al. | |
| 7,482,450 B2 | 1/2009 | Bach et al. | |
| 7,557,249 B2 | 7/2009 | Bagala' Rampazzo et al. | |
| 7,569,692 B2 | 8/2009 | Nii et al. | |
| 7,659,540 B2 | 2/2010 | Heun et al. | |
| 7,701,131 B2 | 4/2010 | Gerhard et al. | |
| 7,723,455 B2 | 5/2010 | Becker et al. | |
| 7,728,137 B2 | 6/2010 | Stossel et al. | |
| 7,737,276 B2 | 6/2010 | Bach et al. | |
| 7,795,801 B2 | 9/2010 | Ueda et al. | |
| 7,816,531 B2 | 10/2010 | Stossel et al. | |
| 7,820,822 B2 | 10/2010 | Fortte et al. | |
| 7,825,249 B2 | 11/2010 | Stossel et al. | |

(Continued)

FOREIGN PATENT DOCUMENTS

| | | |
|---|---|---|
| DE | 102007053771 A1 | 5/2009 |
| DE | 102008015526 A1 | 10/2009 |

(Continued)

OTHER PUBLICATIONS

Ito, A., et al., "*N*-Methyl-Substituted Aza[$1_n$]metacyclophane: Preparation, Structure, and Properties", J. Org. Chem., vol. 64, (1999), pp. 8236-8241.

Japanese Office Action (English Translation) for Japanese Application No. 2011-511992, mailing date Nov. 12, 2013.

Kumar, S., et al., "Heterocalizarenes. Part 4. Synthesis of oxocalix[1]heterocycle[2]-arenas: a unique H-bonding network in calix[1]benzimidazol-2-one[2]arene.½H$_2$O", J. Chem. Soc., Perkin Trans. 1, (2000), pp. 2295-2301.

Moshfegh, A., et al., "118.The Synthesis of 5,11,17-Trihalotetracyclo [13.3.1.13,7.19,13]henicosa-1(19),3,5,7 (20),9,11,13 (21),15,17-nonaene-19,20,21-triols and 5,11,17-Trihalo-19,20,21-trihydroxytetracyclo [13.3.1.13,7 .1 9,13]henicosa-1 (19),3,5,7 (20),9,11,13 (21), 15,17-nonaene-8,14-dione [1]. Cyclo-derivatives of Phloroglucide Analogues", Helvetica Chimica Acta, vol. 65, No. 118, (1982), pp. 1264-1270.

Mysliborski, R., et al., "Subpyriporphyrin-A [14]Triphyrin(1.1.1) Homologue with an Embedded Pyridine Moiety", Angew. Chem. Int. Ed., vol. 45, (2006), pp. 3670-3674.

(Continued)

*Primary Examiner* — Marie R. Yamnitzky
(74) *Attorney, Agent, or Firm* — Drinker Biddle & Reath LLP

(57) ABSTRACT

Organic electroluminescent devices comprising metal complexes according to the formula (1)

formula (1)

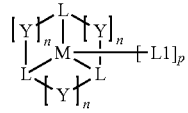

and metal complexes for use in organic electroluminescent devices.

17 Claims, No Drawings

(56) References Cited

U.S. PATENT DOCUMENTS

| | | |
|---|---|---|
| 7,834,136 B2 | 11/2010 | Parham et al. |
| 2005/0069729 A1 | 3/2005 | Ueda et al. |
| 2005/0221115 A1* | 10/2005 | Tsuboyama et al. ......... 428/690 |
| 2005/0260445 A1* | 11/2005 | Walters et al. ............... 428/690 |
| 2006/0284140 A1 | 12/2006 | Breuning et al. |
| 2007/0176147 A1 | 8/2007 | Buesing et al. |
| 2007/0205714 A1 | 9/2007 | Busing et al. |
| 2008/0067925 A1 | 3/2008 | Oshiyama et al. |
| 2008/0312396 A1 | 12/2008 | Stoessel et al. |
| 2009/0134384 A1 | 5/2009 | Stoessel et al. |
| 2009/0167166 A1 | 7/2009 | Bach et al. |
| 2009/0174324 A1 | 7/2009 | Nii et al. |
| 2009/0226759 A1 | 9/2009 | Heun et al. |
| 2009/0270600 A1* | 10/2009 | Raccurt et al. ................. 534/16 |
| 2009/0302742 A1 | 12/2009 | Komori et al. |
| 2009/0302752 A1 | 12/2009 | Parham et al. |
| 2010/0102305 A1 | 4/2010 | Heun et al. |
| 2010/0187977 A1 | 7/2010 | Kai et al. |
| 2010/0227978 A1 | 9/2010 | Stoessel et al. |
| 2010/0244009 A1 | 9/2010 | Parham et al. |
| 2010/0288974 A1 | 11/2010 | Buesing et al. |

FOREIGN PATENT DOCUMENTS

| | | |
|---|---|---|
| DE | 102008036982 A1 | 2/2010 |
| EP | 652273 A1 | 5/1995 |
| EP | 676461 A2 | 10/1995 |
| EP | 707020 A2 | 4/1996 |
| EP | 849107 A1 | 6/1998 |
| EP | 842208 B1 | 5/2000 |
| EP | 1028136 A2 | 8/2000 |
| EP | 1191612 A2 | 3/2002 |
| EP | 1191613 A2 | 3/2002 |
| EP | 1191614 A2 | 3/2002 |
| EP | 1205527 A1 | 5/2002 |
| EP | 1531193 A2 | 5/2005 |
| EP | 1617710 A1 | 1/2006 |
| EP | 1617711 A1 | 1/2006 |
| EP | 1731584 A1 | 12/2006 |
| JP | 05323635 A | 7/1993 |
| JP | 2000044577 A | 2/2000 |
| JP | 03120236 B2 | 12/2000 |
| JP | 2002531913 A | 9/2002 |
| JP | 2003-332074 A | 11/2003 |
| JP | 2004-288381 A | 10/2004 |
| JP | 2005017832 A | 1/2005 |
| JP | 2005162661 A | 6/2005 |
| JP | 2005-531590 | 10/2005 |
| JP | 2005-347160 A | 12/2005 |
| JP | 2006076969 A | 3/2006 |
| JP | 2007214364 A | 8/2007 |
| JP | 2008-506652 | 3/2008 |
| WO | WO-92/018552 A1 | 10/1992 |
| WO | WO-98/027136 A1 | 6/1998 |
| WO | WO-00/22026 A1 | 4/2000 |
| WO | WO-00/70655 A2 | 11/2000 |
| WO | WO-01/41512 A1 | 6/2001 |
| WO | WO-02/02714 A2 | 1/2002 |
| WO | WO-02/15645 A1 | 2/2002 |
| WO | WO-02/060910 A1 | 8/2002 |
| WO | WO-2004/013080 A1 | 2/2004 |
| WO | WO-2004/041901 A1 | 5/2004 |
| WO | WO-2004/070772 A2 | 8/2004 |
| WO | WO-2004/081017 A1 | 9/2004 |
| WO | WO-2004/085449 A1 | 10/2004 |
| WO | WO-2004/093207 A2 | 10/2004 |
| WO | WO-2004/108738 A1 | 12/2004 |
| WO | WO-2004/108857 A1 | 12/2004 |
| WO | WO-2004/113412 A2 | 12/2004 |
| WO | WO-2004/113468 A1 | 12/2004 |
| WO | WO-2005/011013 A1 | 2/2005 |
| WO | WO-2005/014689 A2 | 2/2005 |
| WO | WO-2005/033244 A1 | 4/2005 |
| WO | WO-2005/039246 A1 | 4/2005 |
| WO | WO-2005/040302 A1 | 5/2005 |
| WO | WO-2005/104264 A1 | 11/2005 |
| WO | WO-2005/111172 A2 | 11/2005 |
| WO | WO-2005/113563 A1 | 12/2005 |
| WO | WO-2006/005627 A1 | 1/2006 |
| WO | WO-2006/008069 A1 | 1/2006 |
| WO | WO-2006/061181 A1 | 6/2006 |
| WO | WO-2006/117052 A1 | 11/2006 |
| WO | WO-2007/017066 A1 | 2/2007 |
| WO | WO-2007/063754 A1 | 6/2007 |
| WO | WO-2007/065523 A1 | 6/2007 |
| WO | WO-2007/079585 A1 | 7/2007 |
| WO | WO-2007/137725 A1 | 12/2007 |
| WO | WO-2008/056746 A1 | 5/2008 |
| WO | WO-2008/086851 A1 | 7/2008 |

OTHER PUBLICATIONS

Newkome, G., et al., "1,3,5-Tri[2,6]pyridacyclohexaphane-2,4,6,-trione Ketals: Synthesis, Structural Analysis, and Complexation", J. Org. Chem., vol. 55, (1990), pp. 5714-5719.

Orimoto, Y., et al., "Analytical Method for Predicting Ferromagnetic Properties of Benzyl-Radical Polymers Based on NBMO theory", J. Chem. Theory Comput., vol. 2, (2006), pp. 786-796.

Rajca, A., et al., "Macrocyclic π-Conjugated Carbopolyanions and Polyradicals Based upon Calix[4]arene and and Calix[3]arene Rings", J. Am. Chem. Soc., vol. 117, (1995), pp. 806-816.

Suzuki, Y., et al., "Preparation of N-(p-Tolyl)azacalix[n] (2,6) pyridines Constructed of Various Numbers Of the Recurring Unit", Synlett. No. 2, (2005), pp. 263-266.

Zhang, J., et al., "Using triazine as coupling unit for intramolecular ferromagnetic coupling of multiradicals", Chemical Physics, vol. 246, (1999), pp. 209-215.

Suzuki, Y., et al., "Preparation of N-(0p-Tolyl)azacaliz[n](2,6)pyridines constructed of various numbers of the recurring unit," Synlett 2005, vol. 2, pp. 263-266.

Despotovic, I., et al., "Derivatives of azacalix[3](2,6)pyridine are strong neutral organic superbases: a DFT study," Organic Letters 2007, vol. 9, No. 6, pp. 1101-1104.

Kanbara, T., et al., "New proton-sponge-like macrocyclic compound: synergistic hydrogen bonds of aminopyridine," Eur. J. Org. Chem. 2006, pp. 3314-3316.

Despotovic, I., et al., "Hyperstrong neutral organic bases: phosphazeno azacalix[3](2,6)pyridines," Organic Letters 2007, vol. 9, No. 23, pp. 4709-4712.

Wei, X.-Q., et al., "Synthesis of novel light emitting calix[4]arene derivatives and their luminescent properties," Materials Chemistry and Physics 2007, vol. 102, pp. 214-218.

Legnani, C., et al., "Tunable blue organic light emitting diode based on aluminum calixarene supramolecular complex," Applied Physics Letters 2004, vol. 85, No. 1, pp. 10-12.

English translation of Korean Office Action issued Oct. 29, 2015 for Korean Application No. 2011-7000156.

* cited by examiner

ELECTRONIC DEVICE COMPRISING METAL COMPLEXES

RELATED APPLICATIONS

This application is a national stage application (under 35 U.S.C. §371) of PCT/EP2009/003277, filed May 7, 2009, which claims benefit of German Application No. 10 2008 027 005.9, filed Jun. 5, 2008.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement in OLEDs which exhibit triplet emission, in particular with respect to the stability of the metal complexes, the efficiency, operating voltage and lifetime. Further improvements are therefore desirable here. There is also still a need for improvement in the case of other compounds used in organic electroluminescent devices, such as, for example, matrix materials and charge-transport materials.

In accordance with the prior art, the triplet emitters employed in phosphorescent OLEDs are usually iridium complexes. An improvement in these OLEDs has been achieved by employing metal complexes having polypodal ligands or cryptates, as a consequence of which the complexes have higher thermal stability, which results in a longer lifetime of the OLEDs (WO 04/081017, WO 05/113563, WO 06/008069). However, further improvements in the complexes are still desirable in order to be able to employ these in high-quality and long-lived electroluminescent devices, for example for televisions or computer monitors.

Metal complexes are also employed in other functions in organic electroluminescent devices, for example Alq$_3$ (aluminium tris(hydroxyquinolinate)) as electron-transport material or BAlq (for example T. Tsuji et al., *Journal of the Society of Information Display* 2005, 13(2), 117-122) as triplet matrix material or as hole-blocking material. Further improvements are also still necessary in the case of these materials for use thereof in high-quality electroluminescent devices.

The object of the present invention is therefore to provide novel organic electroluminescent devices comprising metal complexes. The metal complexes can be employed here, in particular depending on the metal used, as emitters, as matrix materials, as hole-blocking materials, as electron-transport materials or also in other functions in the OLED. There is still a particular need for improvement in the case of red-, green- and blue-phosphorescent metal complexes.

Surprisingly, it has been found that certain organic electroluminescent devices comprising the metal chelate complexes described in greater detail below achieve this object and result in significant improvements in the organic electroluminescent device, in particular with respect to the life-time, the efficiency and the stability to heating. This applies, in particular, to green- and blue-phosphorescent electroluminescent devices. The present invention therefore relates to organic electroluminescent devices which comprise these complexes. The present invention furthermore relates to particularly suitable metal complexes which can be used in organic electroluminescent devices.

The prior art includes organic electroluminescent devices which comprise metal complexes having tridentate or polydentate ligands (WO 04/108857), where the ligand represents a linear chain structure. However, it is not evident from this disclosure that it is possible to use a tridentate ligand in the form of a macrocycle, and that this could have advantages with respect to the use of the complex.

Specific metal complexes having tridentate ligands are furthermore known from US 2008/0067925. In these, three coordinating aryl or heteroaryl groups are linked to two divalent connecting groups to form a tridentate linear ligand, which coordinates to a metal from group 8 to 10, in particular to iridium or platinum. These ligands bond to platinum together with a monodentate ligand with formation of a square-planar complex, in which the coordinating atoms of the ligands are in the same plane as the metal atom. However, it is not evident from this disclosure that it is possible also to use these tridentate ligands in the form of a macrocycle, and that this could have advantages with respect to the use of the complex. A corresponding macrocyclic ligand results, in particular, in a different coordination geometry at the metal, meaning that square-planar coordination is no longer possible and that coordination in octahedral complexes can only take place facially.

Metal complexes having tridentate, macrocyclic ligands are generally known (for example WO 07/079,585, EP 1531193). However, these applications only describe the use of these metal complexes as catalytically active activators for inorganic peroxygen compounds in cleaning solutions for hard surfaces and for the removal of oxygen in water-containing systems. A suitability of the metal complexes for organic electronic devices, in particular for organic electroluminescent devices, is not evident from these applications.

The invention thus relates to electronic devices comprising at least one metal complex of the following formula (1)

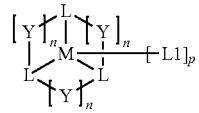

formula (1)

containing a metal M coordinated to a ligand of the formula (2)

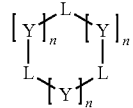

formula (2)

where the following applies to the symbols and indices used:

L is on each occurrence, identically or differently, a substituted or unsubstituted cyclic group, which in each case contains at least one donor atom or a C atom in the ring or an exocyclic donor atom, via which the cyclic group is bonded to the metal M; the groups L are connected to one another via the groups Y;

Y is on each occurrence, identically or differently, a substituted or unsubstituted atom from the third, fourth, fifth or sixth main group, which in each case connects two groups L;

L1 is on each occurrence, identically or differently, a mono-, bi-, tri-, tetra-, penta- or hexadentate ligand which bonds to the metal M;

n is on each occurrence, identically or differently, 0, 1, 2, 3, 4, 5 or 6, where n=0 means that the group Y is not present and a single bond is present between two groups L;

p is 0, 1, 2, 3, 4, 5, 6, 7, 8 or 9.

The index p here is selected so that the coordination number at the metal M corresponds overall, depending on the metal, to the usual coordination number for this metal. For main-group and transition metals, this is usually, depending on the metal, the coordination number 4, 5 or 6, i.e. the index p is usually 1, 2 or 3 for main-group and transition metals if these coordination sites are not saturated by further donor groups bonded to the ligands L. In particular for lanthanides, coordination numbers of up to 12 are also known. It is generally known that metal coordination compounds have different coordination numbers, i.e. bond a different number of ligands, depending on the metal and on the oxidation state of the metal. Since the general expert knowledge of the person skilled in the art in the area of organometallic chemistry or coordination chemistry includes the preferred coordination numbers of metals and metal ions in different oxidation states, it will be easy for the person skilled in the art to use a suitable number of further ligands L1 and thus to select the index p in a suitable manner depending on the metal and its oxidation state and depending on the precise structure of the ligand of the formula (2).

The metal M in compounds of the formula (1) is preferably a transition metal, an alkali metal, an alkaline-earth metal, a main-group metal from main group 3 or 4 or a lanthanide.

An electronic device is taken to mean an electronic device which comprises anode, cathode and at least one layer, where this layer comprises at least one organic or organometallic compound or metal coordination compound. The organic electronic device according to the invention thus comprises anode, cathode and at least one layer which comprises at least one compound of the formula (1) mentioned above. Preferred organic electronic devices here are selected from the group consisting of organic electroluminescent devices (=Organic light-emitting diodes, OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) and organic laser diodes (O-lasers), comprising at least one compound of the formula (1) mentioned above in at least one layer. Particular preference is given to organic electroluminescent devices.

For the purposes of the present invention, a donor atom is taken to mean an atom which has at least one free electron pair and is thus capable of bonding to a metal atom or metal ion. The donor atom here may be neutral or negatively or positively charged. The donor atom is preferably neutral or negatively charged. Examples of neutral donor atoms are nitrogen which is bonded in a heteroaromatic compound, such as, for example, pyridine, or carbon in the form of a carbene. Examples of anionic donor atoms are carbon which is part of an aromatic or heteroaromatic group, such as, for example, a carbon atom in a phenyl group, or nitrogen which is part of a five-membered heteroaromatic group, such as, for example, nitrogen in pyrrole which bonds via the nitrogen. For the purposes of this invention, an exocyclic donor atom is taken to mean a donor atom which is not part of the cyclic group L, but instead is bonded as substituent to L and has at least one free electron pair and is thus capable of bonding to a metal atom. Examples of exocyclic donor atoms are oxygen in the form of a phenolate, sulfur in the form of a thiolate, nitrogen in the form of a nitrile, amine, imine, amide or imide, phosphorus in the form of a phosphine or phosphite or carbon in the form of an isonitrile or acetylide.

The ligand of the formula (2) is an at least tridentate, macrocyclic ligand which bonds to the metal M via the three groups L. For the purposes of this invention, a macrocycle is taken to mean a ring which has at least 10 ring atoms. It should be emphasised here that the ligand of the formula (2) may also have more than three coordination sites and may be, for example, tetradentate, pentadentate or hexadentate, for example if substituents which can likewise bond to the metal M are bonded to the groups Y, as described in greater detail below. Although the complex of the formula (1) and the ligand of the formula (2) are drawn in a planar manner, these structures are not necessarily planar. Instead, the ligand of the formula (2) typically adopts, analogously to calixarenes, a cup-shaped conformation, in which the donor atoms point towards the closed side of the cup and are thus in a conformation which is suitable for bonding to a metal. Further coordination sites to which further ligands, as described by L1 in the structure of the formula (1), can bond are thus sterically accessible on the metal. Thus, for example, tetrahedral complexes are possible, as are octahedral complexes in which the ligand of the formula (2) is facially bonded. In the same way, substituents which are bonded to the groups Y can also bond to the metal M in compounds of the formula (1), depending on the structure. The conformation of the compounds of the formula (1) is shown diagrammatically below, where D generally stands for a donor atom which is coordinated to the metal:

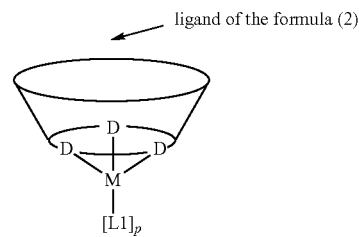

The embodiments of the compound of the formula (1) as are preferably used in the organic electronic device are described below.

Preference is given to compounds of the formula (1), characterised in that they are uncharged, i.e. are electrically neutral. This is achieved in a simple manner by selecting the charge of the groups L and of the bridging units Y and any ligands L1 present in such a way that they compensate for the charge of the complexed metal atom M.

Preference is furthermore given to compounds of the formula (1), characterised in that the sum of the valence electrons around the metal atom is 18. This preference is due to the particular stability of these metal complexes (see, for example, Elschenbroich, Salzer, *Organometallchemie* [Organometallic Chemistry], Teubner Studienbücher, Stuttgart 1993).

The cyclic groups L may be homocycles or heterocycles and may be saturated, olefinic, unsaturated or aromatic or heteroaromatic. In a preferred embodiment of the invention, groups L are, identically or differently on each occurrence, a substituted or unsubstituted aryl or heteroaryl group, or a cyclic, saturated or unsaturated carbene. Preferred substituents are the radicals R indicated below.

A preferred embodiment of the invention is an organic electronic device comprising at least one compound of the formula (3)

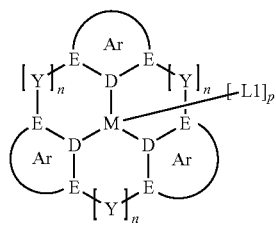

formula (3)

where L1 and p have the same meaning as described above, and the following applies to the other symbols and indices used:

M is a transition metal, a lanthanide, an alkali metal, an alkaline-earth metal or a main-group metal from the third or fourth main group;

D is on each occurrence, identically or differently, C, N, P, C—O$^-$, C—S$^-$, C—NR$_2$ or C—PR$_2$, where the last four groups mentioned bond to the metal as exocyclic donor atoms via O, S, N or P, or C—N≡C, where this group bonds to the metal via the carbon of the exocyclic isonitrile group;

E is on each occurrence, identically or differently, C or N;

Ar is on each occurrence, identically or differently, a group which forms an aryl or heteroaryl group having 5 to 40 aromatic ring atoms together with the group E-D-E and may be substituted by one or more radicals R; or, if D stands for a carbene carbon atom, Ar is a group which forms a cyclic saturated group having 5 to 10 ring atoms together with the group E-D-E;

Y is, identically or differently on each occurrence, BR$^1$, B(R$^1$)$_2^-$, C(R$^1$)$^-$, C(R$^1$)$_2$, Si(R$^1$)$^-$, Si(R$^1$)$_2$, C(=O), C(=NR), N$^-$, NR$^1$, N(R$^1$)$_2^+$, PR$^1$, P(R$^1$)$_2^+$, AsR$^1$, As(R$^1$)$_2^+$, P(=O)R$^1$, As(=O)R$^1$, P(=S)R$^1$, As(=S)R$^1$, O, S, S(R$^1$)$^+$, Se, Te, S(=O), S(=O)$_2$, Se(=O), Se(=O)$_2$, Te(=O) or Te(=O)$_2$;

R is on each occurrence, identically or differently, H, deuterium, F, Cl, Br, I, N(R$^2$)$_2$, CN, NO$_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a diarylamino group, diheteroarylamino group or arylheteroarylamino group having 10 to 40 aromatic ring atoms, which may be substituted by one or more radicals R$^2$, or a combination of these systems; two or more of these substituents R may also form a mono- or polycyclic, aliphatic, aromatic and/or benzo-fused ring system with one another;

R$^1$ is, identically or differently on each occurrence, R or a group L2;

R$^2$ is on each occurrence, identically or differently, H, F or an aliphatic, aromatic and/or heteroaromatic hydrocarbon radical having 1 to 20 C atoms, in which, in addition, one or more H atoms may be replaced by F; two or more substituents R$^2$ here may also form a mono- or polycyclic, aliphatic or aromatic ring system with one another;

L2 is on each occurrence, identically or differently, a donor group having 1 to 40 C atoms, which may form a further bond or coordination to the metal M and may be substituted by one or more radicals R;

n is on each occurrence, identically or differently, 0, 1, 2, 3, 4, 5 or 6, where n=0 means that the group Y is not present and a single bond is present between the two groups L, with the proviso that all indices n do not simultaneously stand for 0.

It should be explicitly emphasised at this point that the radicals R$^1$ which are bonded in the same group Y may also form a ring system with one another. Thus, two radicals R$^1$ which are bonded to the same carbon atom, for example if the group Y stands for C(R$^1$)$_2$, may also form a ring system with one another and thus result in spiro structures. Examples of possible ring systems here are fluorene-like groups if both groups R$^1$ stand for phenyl groups which form a ring system with one another, or 1,3-dioxolanes if both groups R$^1$ stand for alkoxy groups which form a ring system with one another.

It should likewise be explicitly emphasised at this point that radicals R$^1$ which are bonded to the group Y may also form a ring system with radicals R which are bonded to the group L2.

If the symbol D stands for carbon, this formally has, depending on the embodiment, a negative charge, i.e. the corresponding free ligand without the metal M would contain a C—H group at this point, or it stands for a neutral carbene carbon atom. If the symbol D stands for nitrogen, this is, depending on the embodiment, either a neutral donor atom or formally has a negative charge, i.e. the corresponding free ligand without the metal M would contain an N—H group at this point. If the symbol D stands for phosphorus, this is a neutral donor atom.

For the purposes of this invention, a donor group as defined for L2 is taken to mean a substituent or a chemical group which has at least one donor atom which is capable of bonding to the metal M.

For the purposes of this invention, an aryl group contains 6 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc. For the purposes of this invention, a cyclic carbene is a cyclic group which bonds to the metal via a neutral C atom. The cyclic group here may be saturated or unsaturated. Preference is given here to Arduengo carbenes, i.e. carbenes in which two nitrogen atoms are bonded to the carbene C atom. A five-membered Arduengo carbene ring or another unsaturated five-membered carbene ring is likewise regarded as an aryl group for the purposes of this invention.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, etc., are also intended to be taken to mean aromatic ring systems for the purposes of this invention, and likewise systems in which two or more aryl groups are interrupted, for example, by a linear or cyclic alkyl group or by a silyl group.

For the purposes of the present invention, a $C_1$- to $C_{40}$-alkyl group, in which, in addition, individual H atoms or $CH_2$ groups may be substituted by the above-mentioned groups, is preferably taken to mean the radicals methyl, ethyl, n-propyl, i-propyl, n-butyl, 1-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl or cyclooctenyl. An alkynyl group is taken to mean, for example, ethynyl, propynyl, butynyl, pentynyl, hexynyl, heptynyl or octynyl. A $C_1$- to $C_{40}$-alkoxy group is preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and may be linked to the aromatic or heteroaromatic group via any desired positions, is taken to mean, in particular, groups derived from benzene, naphthalene, anthracene, phenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formulae (1) and (3) in which M stands for a transition metal, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, platinum and gold. Very particular preference is given to iridium and platinum. The metals here can be in various oxidation states. The above-mentioned metals are preferably in the Cr(0), Cr(II), Cr(III), Cr(IV), Cr(VI), Mo(0), Mo(II), Mo(III), Mo(IV), Mo(VI), W(O), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V) oxidation states; very particular preference is given to Mo(0), W(0), Re(I), Ru(II), Os(II), Rh(III), Ir(III) and Pt(II).

Preference is furthermore given to compounds of the formulae (1) and (3) in which M stands for a main-group metal selected from the group consisting of lithium, sodium, magnesium, aluminium, gallium, indium and tin, or for scandium, yttrium or lanthanum. Particular preference is given to Li(I), Na(I), Mg(II), Al(III), Ga(III), In(III), Sc(III), Y(III) or La(III), very particularly preferably Al(III).

In a preferred embodiment of the invention, the index n stands on each occurrence, identically or differently, for 0, 1, 2 or 3, with the proviso that all indices n do not simultaneously stand for 0, particularly preferably for 0, 1 or 2, with the proviso that all indices n do not simultaneously stand for 0. In a very particularly preferred embodiment of the invention, the index n stands on each occurrence, identically or differently, for 1 or 2, in particular for 1.

In a preferred embodiment of the invention, Y stands, identically or differently on each occurrence, for $C(R^1)_2$, $C(R^1)^-$, $C(=O)$, $NR^1$, $PR^1$, $P(=O)R^1$, O or S, particularly preferably for $C(R^1)_2$, $C(=O)$ or $NR^1$.

In a further preferred embodiment of the invention, a group Y or, in a particularly preferred embodiment, two groups Y or, in a very particularly preferred embodiment, all three groups Y stand for $BR^1$, $C(R^1)_2$, $Si(R^1)_2$, $NR^1$, $PR^1$, $AsR^1$, $P(=O)R^1$, $As(=O)R^1$, $P(=S)R^1$ or $As(=S)R^1$, and the substituent $R^1$ or one of the substituents $R^1$ in the case of $C(R^1)_2$ and $Si(R^1)_2$ stands for a group L2.

A preferred embodiment of the invention is thus an organic electronic device comprising the compounds of the following formulae (4), (5) and (6):

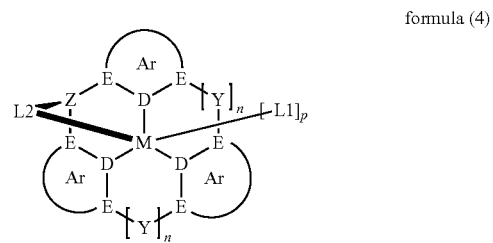

formula (4)

formula (5)

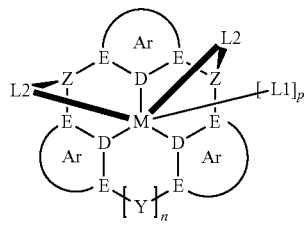

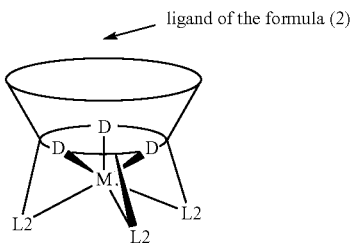

ligand of the formula (2)

If a plurality of substituents R on different ligand groups L2 form a ring system with one another, the formation of cryptates is also possible, as depicted diagrammatically below, where V very generally stands for a bridging unit which is formed by ring closure of a plurality of substituents R:

formula (6)

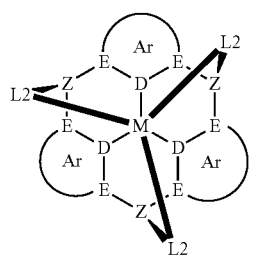

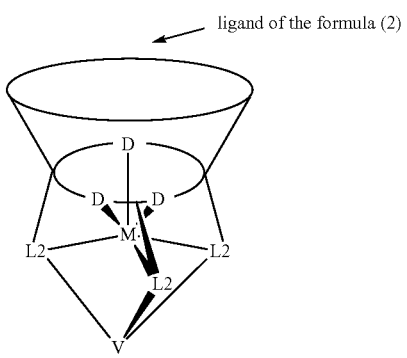

ligand of the formula (2)

where Z stands, identically or differently on each occurrence, for B, B(R$^1$)$^-$, C$^-$, CR$^1$, SiR$^1$, N, P, As, P(=O), As(=O), P(=S) or As(=S), preferably for CR$^1$, N, P or P(=O)R$^1$, and the other symbols and indices have the meanings indicated above.

The compounds of the formula (5) and of the formula (6) are specific embodiments of the compounds of the formula (4). In compounds of the formula (6), the three aromatic groups bond facially to M via the donor atom D, and the three groups L2 bond facially to the metal.

A preferred embodiment of the compounds of the formula (6) are the compounds of the formula (6a)

If the bridging group V in the structure depicted above stands for a group Z, compounds of the formula (6a) indicated above are obtained.

In a further preferred embodiment of compounds of the formula (1), the index p=1, 2 or 3, and the ligand L1 is a ligand of the formula (2), i.e. the metal complex contains two, three or four ligands of the formula (2). This preferred embodiment of compounds of the formula (1) is represented by compounds of the formula (7):

formula (6a)

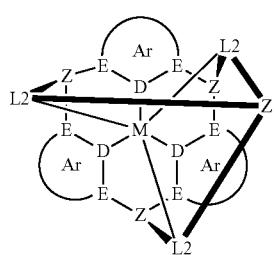

formula (7)

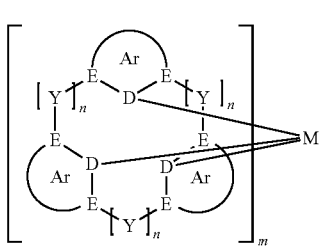

where the symbols used have the same meaning as described above.

It should again be mentioned here that the substituents R on L2 may form a ring system with the substituents R$^1$ on Z.

Although the compounds of the formulae (4), (5) and (6) are depicted flat, these also typically adopt a three-dimensional structure analogously to the compounds of the formula (1) depicted above, as depicted diagrammatically below for compounds of the formula (6), where D generally stands for a donor atom:

where the symbols and indices used have the meanings mentioned above, and m, depending on the metal used, stands for 2, 3 or 4. For main-group and transition metals, m preferably stands for 2; for lanthanides, m may also stand for 3 or 4. Furthermore, two or more ligands of the formula (2) in these complexes may also be linked by a bridge through two or more groups R or R$^1$ being linked to one another.

The compounds of the formula (7) also typically adopt a three-dimensional structure analogously to the compounds of the formula (1) depicted above, as depicted diagrammatically below for m=2, where D generally stands for a donor atom:

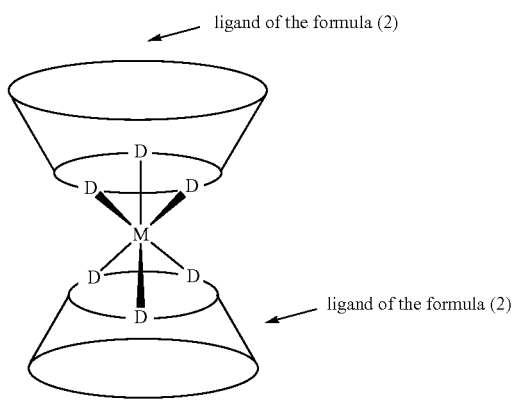
← ligand of the formula (2)

← ligand of the formula (2)

In a preferred embodiment of compounds of the formulae (3) to (7), the symbol D stands, identically or differently on each occurrence, for C or N. The carbon here is either formally negatively charged, i.e. it would have a negative charge in the ligand without the metal, or it is neutral and is a carbene carbon atom. If the symbol D stands for N or a formally negative carbon atom, both symbols E which are bonded to this D preferably simultaneously stand for C. If the symbol D stands for a carbene carbon atom, at least one symbol E, particularly preferably both symbols E which are bonded to this D, preferably stands for N, i.e. Arduengo carbenes are preferably present. This preference is due to the particular stability of these carbenes.

In a further preferred embodiment of the formulae (1) and (3) to (7), the group L or the aryl or heteroaryl group which is formed by E-D-E together with Ar is an aryl or heteroaryl group having 5 to 20 aromatic ring atoms, particularly preferably having 5 to 14 aromatic ring atoms. This may in each case be substituted by one or more radicals R. Particularly preferred aryl or heteroaryl groups are benzene, phenol, thiophenol, naphthalene, anthracene, phenanthrene, thiophene, pyrrole, furan, pyridine, pyrimidine, pyrazine, pyridazine, triazine, benzothiophene, indole, benzofuran, quinoline, isoquinoline, quinoxaline, imidazole, pyrazole, benzimidazole, oxazole, thiazole, benzoxazole or benzothiazole, each of which may be substituted by R. Particular preference is furthermore given to Arduengo carbenes.

Particular preference is given to compounds of the formulae (1) and (3) to (7) in which the group L in compounds of the formula (1) or the aryl or heteroaryl group formed by Ar together with the group E-D-E in compounds of the formulae (3) to (7) stands for a group of the following formulae (8) to (20), where the dashed bond in each case indicates the bonding of this group in the ligand, i.e. the bond to the groups Y, and where * in each case denotes the position of the coordination to the metal M:

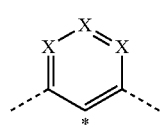
formula (8)

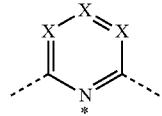
formula (9)

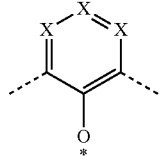
formula (10)

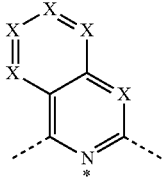
formula (11)

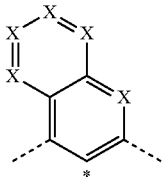
formula (12)

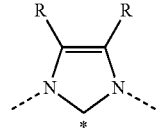
formula (13)

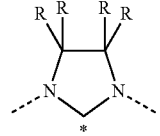
formula (14)

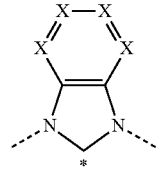
formula (15)

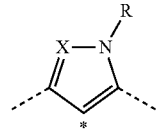
formula (16)

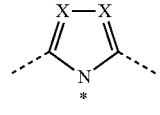
formula (17)

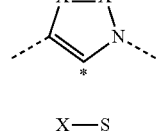
formula (18)

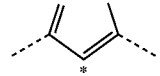
formula (19)

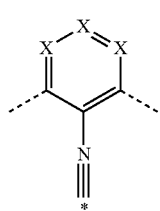

formula (20)

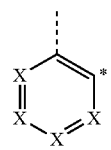

formula (21)

The symbols used here have the same meaning as described above, and X stands, identically or differently on each occurrence, for CR or N, with the proviso that a maximum of three symbols X in each group stand for N. Preferably a maximum of two symbols X in each group stand for N, particularly preferably a maximum of one symbol X in each group stands for N, very particularly preferably all symbols X stand for CR.

In a further preferred embodiment of the invention, the compound of the formula (1) or of the formulae (3) to (7) contains at least one direct metal-carbon bond, preferably at least two direct metal-carbon bonds, particularly preferably three direct metal-carbon bonds. These can be bonds from the groups L of the ligand of the formula (2) or bonds from the donor atom D, if this is equal to carbon, to the metal in compounds of the formulae (3) to (7). However, these can also be bonds from the group L2 to the metal in compounds of the formulae (4) to (6).

In a further preferred embodiment of the invention, the group L2 is, identically or differently on each occurrence, an aryl or heteroaryl group having 5 to 40 aromatic ring atoms, which may be substituted by one or more radicals R and/or which may also contain an exocyclic donor atom, or a neutral or anionic donor group which bonds to the metal via oxygen, nitrogen, phosphorus or sulfur and which may be substituted by one or more radicals R. The aryl or heteroaryl groups here preferably bond to the metal via the ortho-position to the link to Z. Preferred aryl and heteroaryl groups are benzene, 2-phenol, 2-thiophenol, naphthalene, anthracene, phenanthrene, pyridine, quinoline, isoquinoline, pyrazine, quinoxaline, pyrimidine, pyridazine, triazine, pyrrole, indole, imidazole, furan, benzofuran, benzimidazole, pyrazole, triazole, oxazole, thiazole, thiophene, benzothiophene, benzoxazole or benzothiazole, each of which may be substituted by one or more radicals R. The bonding to the group Z of the ligand and the bonding to the metal preferably take place in these groups via two directly adjacent atoms in these groups, i.e. via ortho-positions of the benzene, etc. Depending on the group, the above-mentioned groups are groups which coordinate in a neutral manner, for example pyridine, which bonds via a neutral N atom, or groups which coordinate in an anionic manner, for example benzene, thiophene and phenol, which bond via a negatively charged C atom or O atom. Further preferred groups L2 are unsaturated or saturated cyclic Arduengo carbenes, in particular unsaturated cyclic Arduengo carbenes, each of which may be substituted by one or more radicals R, and alkenes or imines, each of which may be substituted by one or more radicals R.

If the group L2 represents an aryl or heteroaryl group or an alkene or imine, this is particularly preferably selected from groups of the formulae (21) to (49), where the dashed bond in each case indicates the bonding of this group in the ligand, i.e. the bond to the group Z, where * in each case denotes the position of the coordination to the metal M, and where the symbols used have the meanings indicated above:

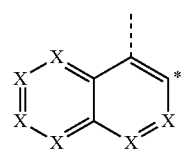

formula (22)

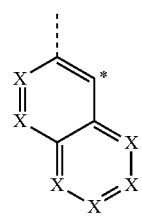

formula (23)

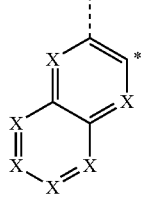

formula (24)

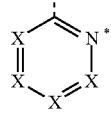

formula (25)

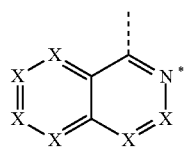

formula (26)

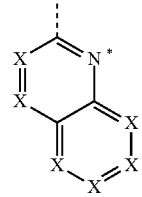

formula (27)

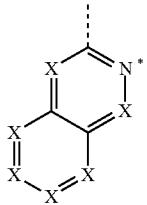

formula (28)

formula (29)
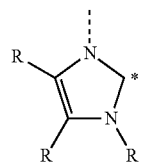
formula (30)
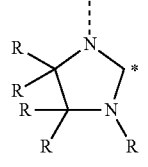
formula (31)
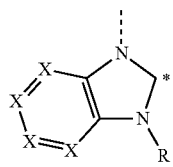
formula (32)
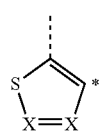
formula (33)
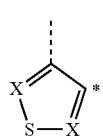
formula (34)
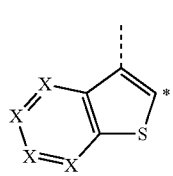
formula (35)
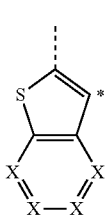
formula (36)
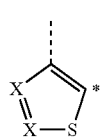
formula (37)
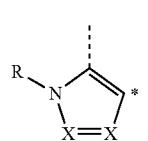
formula (38)
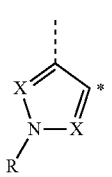
formula (39)
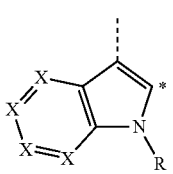
formula (40)
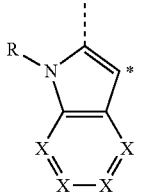
formula (41)
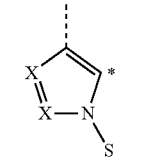
formula (42)
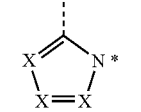
formula (43)
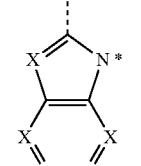
formula (44)
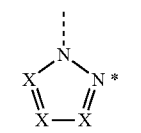
formula (45)
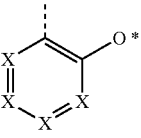
formula (46)
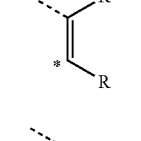
formula (47)
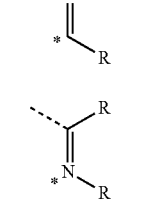
formula (48)

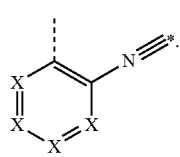

formula (49)

Particularly preferred embodiments of the invention are compounds in which groups (8) to (20) are combined with groups (21) to (49).

L2 may furthermore preferably represent a neutral or anionic donor group, preferably a monodentate or bidentate chelating group, particularly preferably a monodentate group. The donor atoms here are preferably carbon, oxygen, nitrogen, phosphorus or sulfur, particularly preferably nitrogen or oxygen.

Preferred carbon-containing donor groups are acetylides and aliphatic or aromatic isonitriles.

Preferred nitrogen-containing donor groups, apart from the aromatic nitrogen heterocycles mentioned above, are aliphatic amines, preferably containing $C_1$-$C_{20}$-alkyl groups, particularly preferably containing $C_1$-$C_{10}$-alkyl groups, very particularly preferably containing $C_1$-$C_4$-alkyl groups, aliphatic cyclic amines, for example pyrrolidine, piperidine or morpholine, nitriles, amides, imides and imines, each of which may be substituted by groups R or unsubstituted.

Preferred phosphorus-containing donor groups are $PF_2$, $P(NR_2)_2$, where R stands, identically or differently on each occurrence, for a $C_1$-$C_{20}$-alkyl group or an aryl or heteroaryl group in the sense of the definition given above, alkyl-, aryl- or mixed alkylarylphosphines, alkylhalo-, arylhalo- or mixed alkylarylhalophosphines, where the halogen may in each case be F, Cl, Br or I, alkyl, aryl or mixed alkyl aryl phosphites or phosphaaromatic compounds, such as, for example, phosphabenzene, each of which may be substituted by groups R or unsubstituted. The alkyl groups here are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred oxygen-containing donor groups, apart from the phenol mentioned above, are alcohols, alcoholates, open-chain or cyclic, aliphatic or aromatic ethers, oxygen heterocycles, such as, for example, furan, aldehydes, ketones, phosphine oxide groups, phosphates, phosphonates, borates, silicates, sulfoxide groups, carboxylates, phenols, phenolates, oximes, hydroxamates, β-ketoketonates, β-keto esters and β-diesters, each of which may be substituted by groups R or unsubstituted, where the last-mentioned groups represent bidentate-chelating ligands. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred sulfur-containing donor groups, apart from the sulfur heteroaromatic compounds mentioned above, are aliphatic or aromatic thiols and thiolates, open-chain or cyclic thioethers, thiocarbonyl groups, phosphine sulfides and thiocarboxylates, each of which may be substituted by groups R or unsubstituted. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Bidentate-chelating groups can also be formed from these donor groups by combining two of these groups, which may be identical or different and may have identical or different donor atoms. These groups may also be substituted by one or more radicals R. Examples of bidentate-chelating groups of this type are substituted or unsubstituted β-ketoketonates, β-keto esters, β-diesters, carboxylates derived from aminocarboxylic acids, such as, for example, pyridine-2-carboxylic acid, quinoline-2-carboxylic acid, glycine, dimethylglycine, alanine or dimethylaminoalanine, iminoacetoacetonates, hydroxamates, pyridylphosphines, α-phosphinocarboxylates, glycol ethers, ether alcoholates, dialcoholates derived from dialcohols, such as, for example, ethylene glycol or 1,3-propylene glycol, dithiolates derived from dithiols, such as, for example, 1,2-ethylenedithiol or 1,3-propylenedithiol, diamines, such as, for example, ethylenediamine, propylenediamine or cis- or trans-diaminocyclohexane, imines, such as, for example, 2-[1-(phenylimino)ethyl]pyridine, 2-[1-(2-methylphenylimino)-ethyl]pyridine, 2-[1-(2,6-di-iso-propylphenylimino)ethyl]pyridine, 2-[1-(methylimino)ethyl]pyridine, 2-[1-(ethylimino)ethyl]pyridine, 2-[1-(iso-propylimino)ethyl]pyridine or 2-[1-(tert-butylimino)ethyl]pyridine, diimines, such as, for example, 1,2-bis(methylimino)ethane, 1,2-bis(ethylimino)ethane, 1,2-bis(iso-propylimino)ethane, 1,2-bis(tert-butylimino)ethane, 2,3-bis-(methylimino)butane, 2,3-bis(ethylimino)butane, 2,3-bis(iso-propylimino)-butane, 2,3-bis(tert-butylimino)butane, 1,2-bis(phenylimino)ethane, 1,2-bis(2-methylphenylimino)ethane, 1,2-bis(2,6-di-iso-propylphenylimino)-ethane, 1,2-bis(2,6-di-tert-butylphenylimino)ethane, 2,3-bis (phenylimino)-butane, 2,3-bis(2-methylphenylimino)butane, 2,3-bis(2,6-di-iso-propylphenylimino)butane or 2,3-bis(2,6-di-tert-butylphenylimino)butane, diphosphines, such as, for example, bis(diphenylphosphinomethane, bis-(diphenylphosphino)ethane, bis(diphenylphosphino)propane, bis(dimethylphosphino)methane, bis(dimethylphosphino)ethane, bis(dimethylphosphino)propane, bis(diethylphosphino)methane, bis(diethylphosphino)-ethane, bis(diethylphosphino)propane, bis(di-tert-butylphosphino)methane, bis(di-tert-butylphosphino)ethane, bis(tert-butylphosphino)propane, salicyliminates derived from salicylimines, such as, for example, methylsalicylimine, ethylsalicylimine or phenylsalicylimine, etc.

Tridentate- or polydentate-chelating groups can also be formed entirely analogously.

The ligands L1 are preferably neutral, monoanionic, dianionic or trianionic ligands, particularly preferably neutral or monoanionic ligands. They are preferably monodentate, bidentate or tridentate, i.e. have one, two or three coordination sites.

Preferred neutral, monodentate ligands L1 are selected from carbon monoxide, isonitriles, such as, for example, tert-butyl isonitrile, cyclohexyl isonitrile, adamantyl isonitrile, phenyl isonitrile, mesityl isonitrile, 2,6-dimethylphenyl isonitrile, 2,6-di-iso-propylphenyl isonitrile, 2,6-di-tert-butylphenyl isonitrile, amines, such as, for example, trimethylamine, triethylamine, morpholine, phosphines, such as, for example, trifluorophosphine, trimethylphosphine, tricyclohexylphosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tertbutylstibine, triphenylstibine, tris(pentafluorophenyl)stibine, and nitrogen-containing heterocyclic compounds, such as, for example, pyridine, pyridazine, pyrazine, pyrimidine, triazine.

Preferred monoanionic, monodentate ligands L1 are selected from hydride, deuteride, the halides F, Cl, Br and I, alkylacetylides, such as, for example, methyl-C≡C⁻, tert-butyl-C≡C⁻, arylacetylides, such as, for example, phenyl-C≡C⁻, cyanide, cyanate, isocyanate, thiocyanate, isothiocyanate, aliphatic or aromatic alcoholates, such as, for example, methanolate, ethanolate, propanolate, iso-propanolate, tert-butylate, phenolate, aliphatic or aromatic thioalcoholates, such as, for example, methanethiolate, ethanethiolate, propanethiolate, iso-propanethiolate, tert-thiobutylate, thiophenolate, amides, such as, for example, dimethylamide, diethylamide, di-iso-propylamide, morpholide, carboxylates, such as, for example, acetate, trifluoroacetate, propionate, benzoate, and anionic, nitrogen-containing heterocyclic compounds, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are $O^{2-}$, $S^{2-}$, nitrenes, which result in coordination in the form R—N=M, where R generally stands for a substituent, or $N^{3-}$.

Preferred neutral or mono- or dianionic bidentate or polydentate ligands L1 are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-di-iso-propylphenylimino)ethyl]pyridine, 2-[1-(methylimino) ethyl]-pyridine, 2-[1-(ethylimino)ethyl]pyridine, 2-[1-(iso-propylimino)ethyl]pyridine, 2-[1-(tert-butylimino)ethyl] pyridine, diimines, such as, for example, 1,2-bis (methylimino)ethane, 1,2-bis(ethylimino)ethane, 1,2-bis (iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tertbutylimino)butane, 1,2-bis(phenylimino)ethane, 1,2-bis(2-methylphenylimino)ethane, 1,2-bis(2,6-di-iso-propylphenylimino)ethane, 1,2-bis(2,6-di-tert-butylphenylimino)ethane, 2,3-bis (phenylimino)butane, 2,3-bis(2-methylphenylimino)butane, 2,3-bis(2,6-di-iso-propylphenylimino)butane, 2,3-bis(2,6-di-tert-butylphenylimino)butane, heterocyclic compounds containing two nitrogen atoms, such as, for example, 2,2'-bipyridine, o-phenanthroline, diphosphines, such as, for example, bis(diphenylphosphino)-methane, bis(diphenylphosphino)ethane, bis(diphenylphosphino)propane, bis(dimethylphosphino)methane, bis(dimethylphosphino)ethane, bis-(dimethylphosphino)propane, bis(diethylphosphino) methane, bis(diethylphosphino)ethane, bis(diethylphosphino)propane, bis(di-tert-butylphosphino)methane, bis(di-tert-butylphosphino)ethane, bis(tert-butylphosphino)-propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicylimines derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocyclic compounds, such as, for example, tetrakis(1-imidazolyl)borate and tetrakis(1-pyrazolyl)borate.

Preference is furthermore given to bidentate monoanionic ligands L1 which, with the metal, form a cyclometallated five-membered ring containing at least one metal-carbon bond. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of such ligands is known to the person skilled in the art in the area of phosphorescent electroluminescent devices, and he will be able, without inventive step, to select further ligands of this type as ligand L1 for compounds of the formula (1). The combination of two groups as depicted above by the formulae (21) to (49) is generally particularly suitable for this purpose, where one group is bonded via a neutral nitrogen atom or a carbene atom and the other group is bonded via a negatively charged carbon atom or a negatively charged nitrogen atom. The ligand L1 can then be formed from the groups of the formulae (21) to (49) by bonding these groups to one another, in each case at the bond indicated by a dashed bond.

Likewise preferred ligands L1 are $\eta^5$-cyclopentadienyl, $\eta^5$-pentamethyl-cyclopentadienyl, $\eta^6$-benzene or $\eta^7$-cycloheptatrienyl, each of which may be substituted by one or more radicals R.

Likewise preferred ligands L1 are 1,3,5-cis-cyclohexane derivatives, in particular of the formula (50), 1,1,1-tri(methylene)methane derivatives, in particular of the formula (51), and 1,1,1-trisubstituted methanes, in particular of the formula (52):

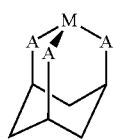

formula (50)

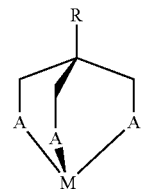

formula (51)

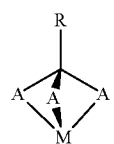

formula (52)

where the coordination to the metal M is depicted in each of the formulae, R has the meaning mentioned above, and A stands, identically or differently on each occurrence, for O⁻, S⁻, COO⁻, $P(R)_2$ or $N(R)_2$.

A further preferred embodiment of the invention is an organic electronic device comprising at least one compound of the formulae (53), (54) and (55):

formula (53)

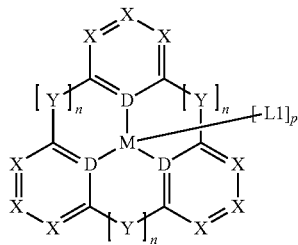

formula (57)

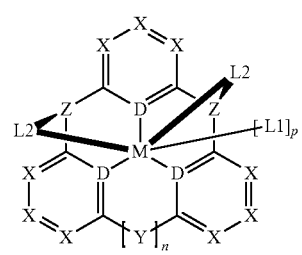

formula (54)

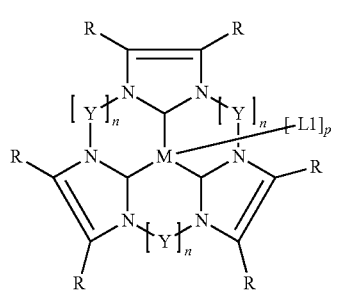

formula (58)

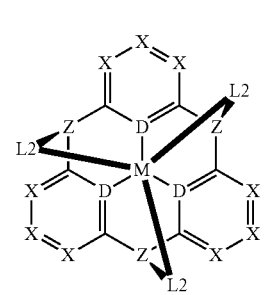

(formula 55)

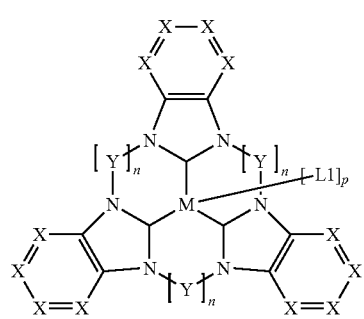

formula (59)

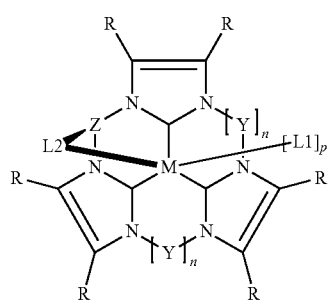

where M, X, Y, L1, R, R¹, n and p have the meanings mentioned above, and furthermore:

D stands on each occurrence, identically or differently, for C, N or C—O⁻.

A particularly preferred embodiment of the invention are compounds of the formulae (53) to (55) in which one group Y, two groups Y or all three groups Y stand for $BR^1$, $C(R^1)_2$, $Si(R^1)_2$, $NR^1$, $PR^1$, $AsR^1$, $P(=O)R^1$, $As(=O)R^1$, $P(=S)R^1$ or $As(=S)R^1$ and the substituent $R^1$ or one of the substituents $R^1$ in the case of $C(R^1)_2$ and $Si(R^1)_2$ stands for a group L2. Particularly preferred embodiments of the invention are thus the compounds of the following formulae (56) to (64):

formula (60)

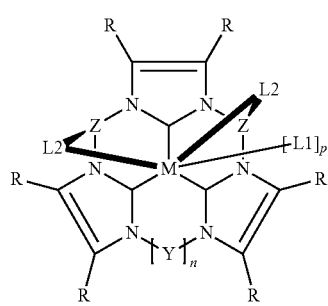

formula (56)

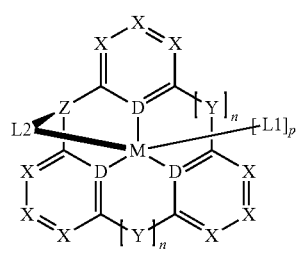

formula (61)

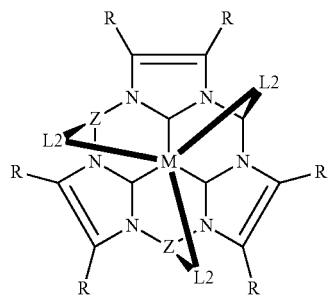

formula (62)

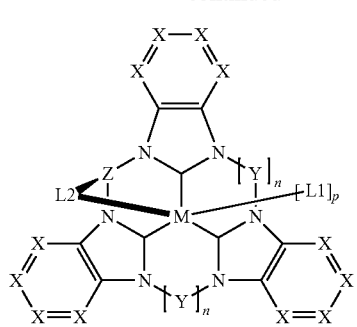

formula (63)

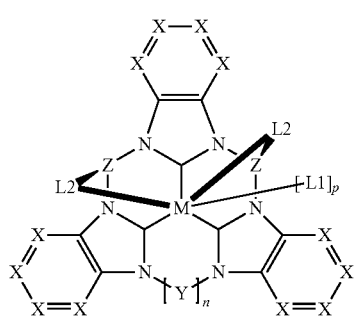

formula (64)

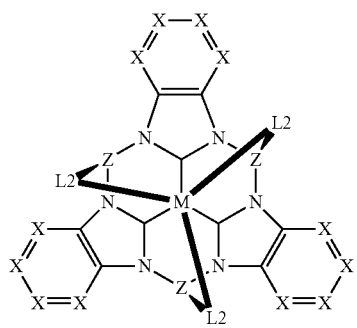

where the symbols and indices have the meanings indicated above. The groups L2 here are preferably, identically or differently on each occurrence, groups of the formulae (21) to (49) depicted above.

A further particularly preferred embodiment of the compounds of the formula (8) are the compounds of the following formula (65):

formula (65)

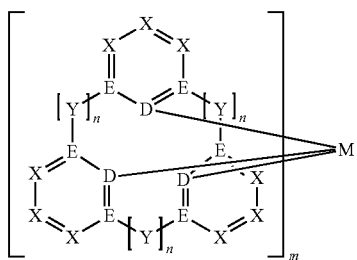

where the symbols and indices have the same meanings as described above.

Preferred embodiments of the compounds of the formulae (53) to (55) and (56) to (65) are those as have already been described in detail above for the compounds of the formulae (3) to (7).

Preference is furthermore given to compounds of the formulae (3) to (7) and (53) to (65) in which R stands on each occurrence, identically or differently, for H, deuterium, F, CN, a straight-chain alkyl or alkoxy group having 1 to 6 C atoms or a branched or cyclic alkyl or alkoxy group having 3 to 6 C atoms, each of which may be substituted by one or more radicals $R^2$, where one or more non-adjacent $CH_2$ groups may be replaced by $R^2C=CR^2$, O or S and one or more H atoms may be replaced by F, or an aryl or heteroaryl group having 5 to 16 aromatic ring atoms, which may in each case be substituted by one or more radicals $R^2$, or a diarylamino group having 10 to 20 aromatic ring atoms, which may be substituted by one or more radicals $R^2$, or a combination of these systems; two or more substituents R here may also form a mono- or polycyclic aliphatic, aromatic and/or benzo-fused ring system with one another. The symbol R particularly preferably stands, identically or differently on each occurrence, for H, deuterium, F, a straight-chain alkyl group having 1 to 4 C atoms or a branched alkyl group having 3 or 4 C atoms, each of which may be substituted by one or more radicals $R^2$, where one or more H atoms may be replaced by F, or an aryl group having 6 to 10 aromatic ring atoms, which may be substituted by one or more radicals $R^2$; two or more substituents R here may also form a mono- or polycyclic aliphatic, aromatic and/or benzo-fused ring system with one another.

The complexes of the formula (1) can in principle be prepared by various processes, but the processes described below have proven particularly suitable. The complexes of the formula (1) are obtained by reaction of the ligand of the formula (2) and optionally further ligands L1 with metal alkoxides of the formula (66), with metal ketoketonates of the formula (67) or metal halides of the formula (68):

formula (66)

$$M(OR^2)_r$$

formula (67)

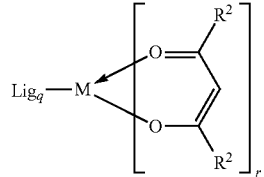

formula (68)

$$MHal_r$$

where M and $R^2$ have the same meaning as described above, and the following applies to the other symbols and indices:

Hal is on each occurrence, identically or differently, F, Cl, Br or I;

Lig is on each occurrence, identically or differently, a neutral or monoanionic, monodentate or bidentate ligand, for example a halide or hydroxide;

q is on each occurrence, identically or differently, 0, 1, 2, 3 or 4, preferably 0, 1 or 2;

r is on each occurrence, identically or differently, 1, 2, 3, 4 or 5, where r in formulae (66) and (68) indicates the valency of the metal M;

the compound of the formula (67) may also be charged and may also contain a counterion; the compounds of the formulae (66) to (68), in particular of the formula (68), may furthermore also be in the form of the hydrate.

A complex-analogous synthesis of the ligands is likewise possible by reacting precursors of the ligand with metal compounds of the formula (66), (67) or (68) and then converting the metal complexes formed in this way further into the finished ligand.

The synthesis can be activated, for example, thermally, photochemically or by microwave radiation. The synthesis of tris-ortho-metallated metal complexes is described in general in WO 02/060910, WO 04/085449, WO 04/108738 and WO 07/065523. The synthetic processes and preferred reaction conditions indicated in these specifications can be applied analogously to the synthesis of compounds of the formula (1). Preferred starting compounds for iridium complexes are compounds of the formula (67), in particular the compound Na[IrCl$_2$(acac)$_2$], and compounds of the formula (68) in the form of hydrates, in particular IrCl$_3$ hydrate.

These processes enable the complexes to be obtained easily in high purity, preferably in a purity of >99% according to $^1$H-NMR or HPLC, particularly preferably >99.9%.

Examples of preferred compounds of the formula (1) are compounds (1) to (307) depicted below. These complexes can be prepared, inter alia, using the synthetic methods explained above.

(1)
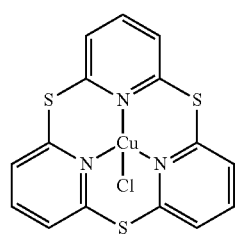

(2)
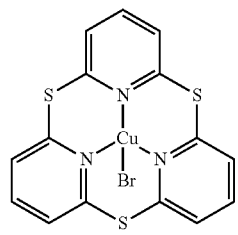

(3)
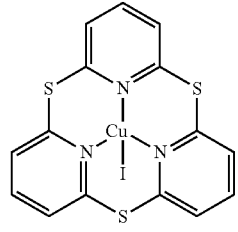

(4)
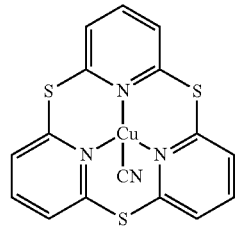

-continued (5)
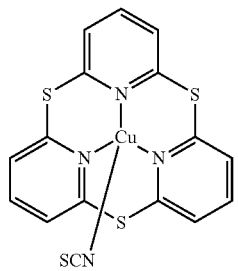

(6)
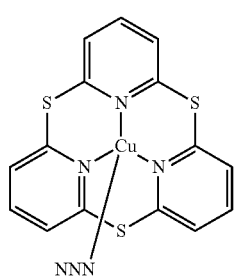

(7)
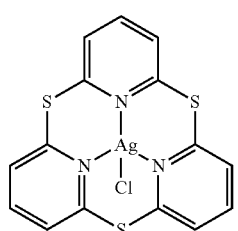

(8)
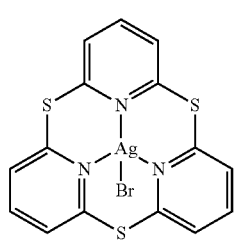

(9)
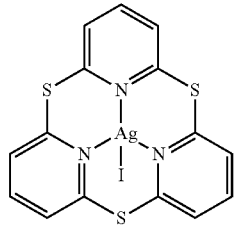

(10)
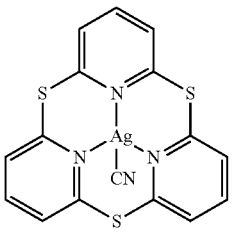

(11) 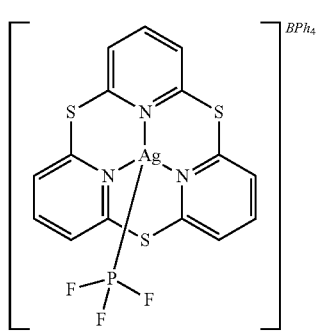
(12) 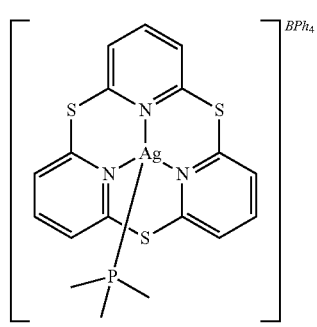
(13) 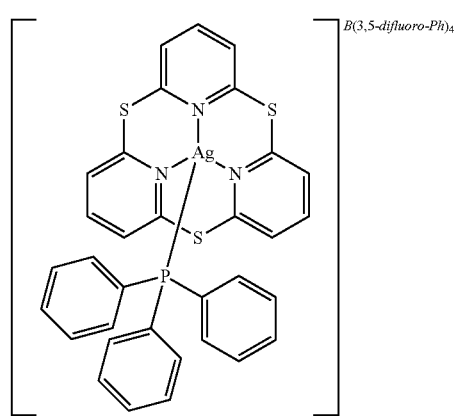
(14) 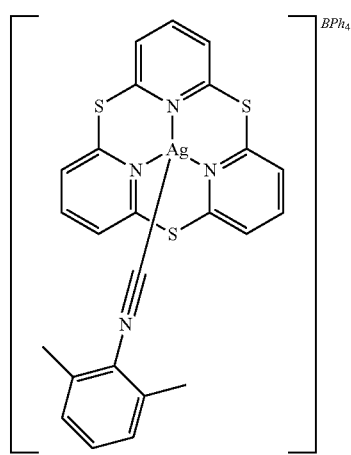
(15) 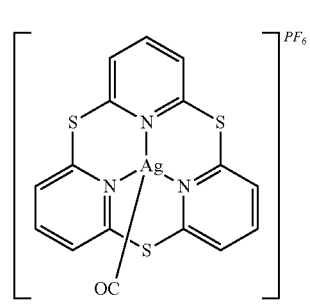
(16) 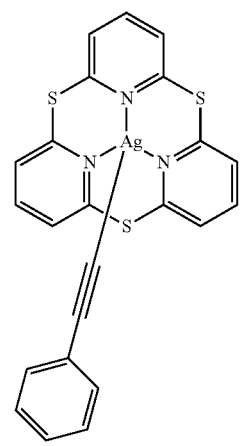
(17) 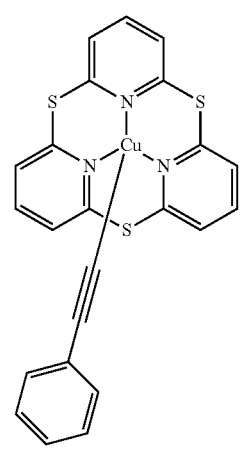
(18) 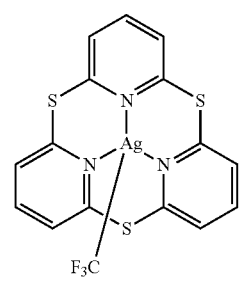

(19)
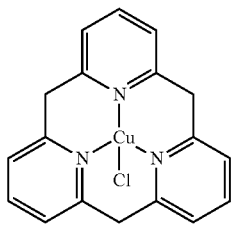
(20)
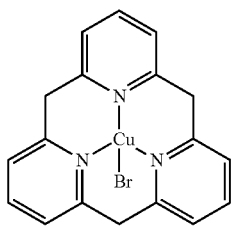
(21)
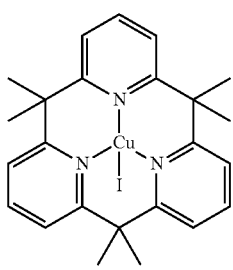
(22)
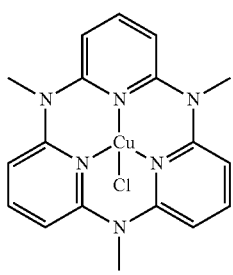
(23)
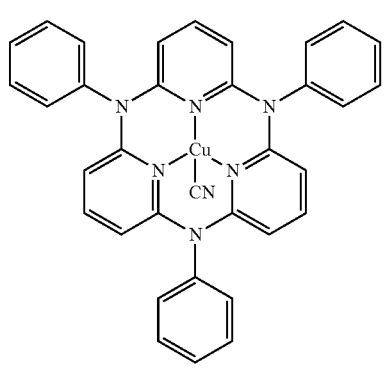
(24)
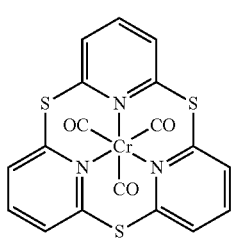
(25)
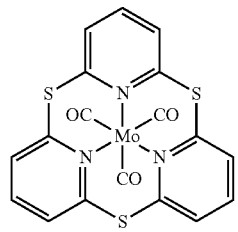
(26)
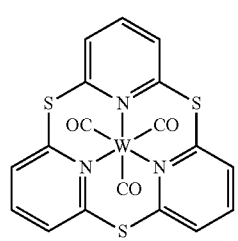
(27)
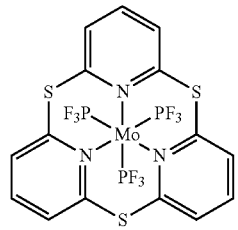
(28)
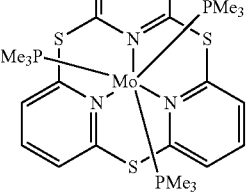
(29)
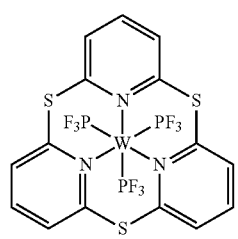
(30)
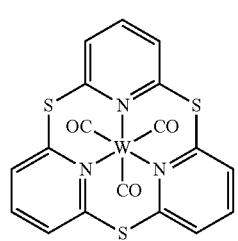

-continued
(31)
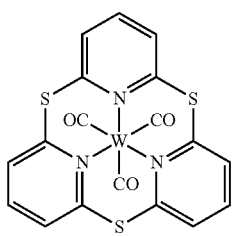
(32)
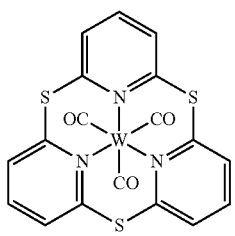
(33)
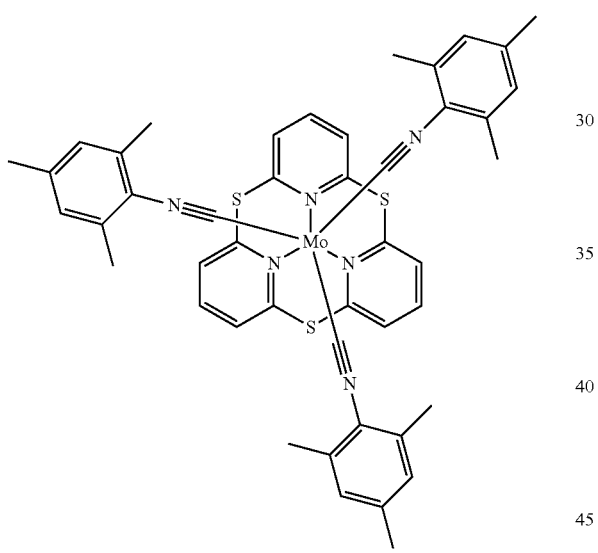
(34)
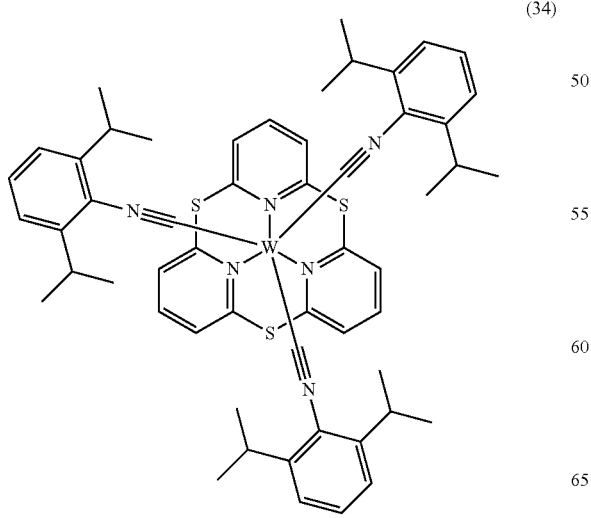
-continued
(35)
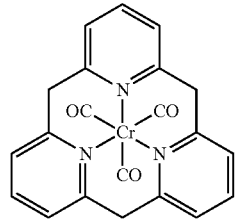
(36)
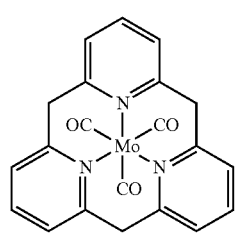
(37)
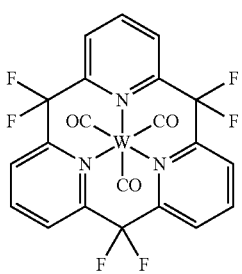
(38)
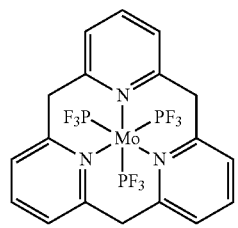
(39)
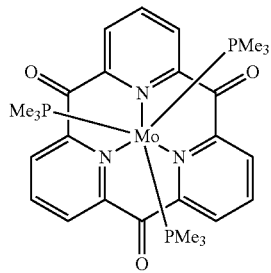
(40)
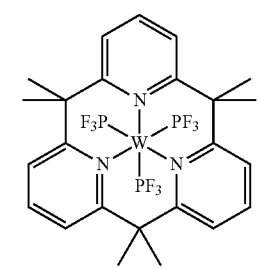

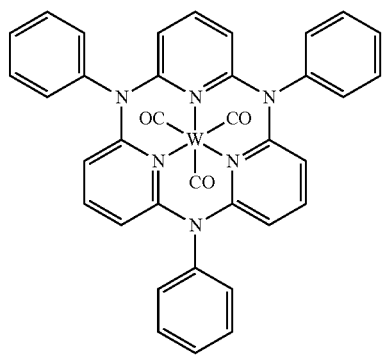 (41)
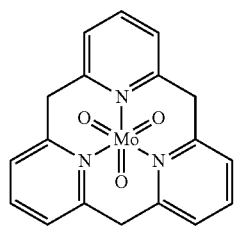 (45)
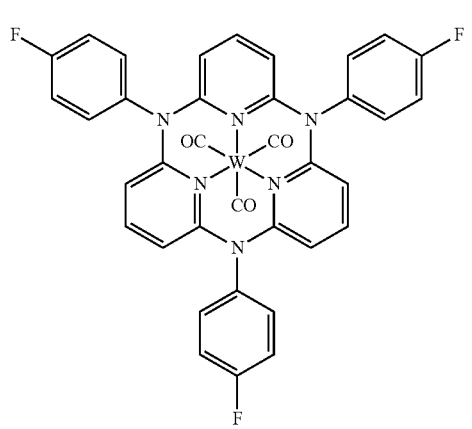 (42)
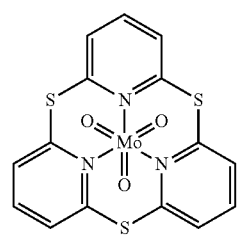 (46)
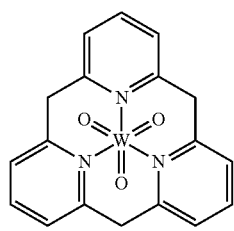 (47)
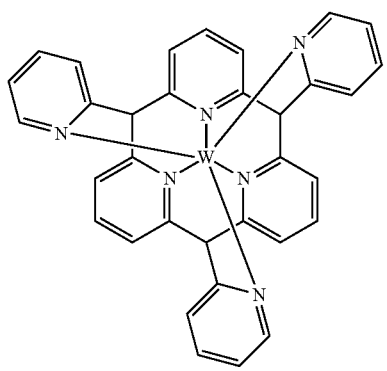 (43)
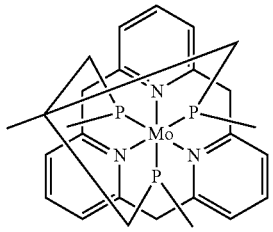 (48)
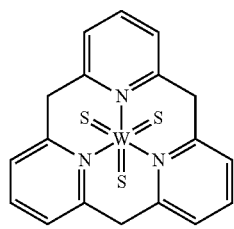 (49)
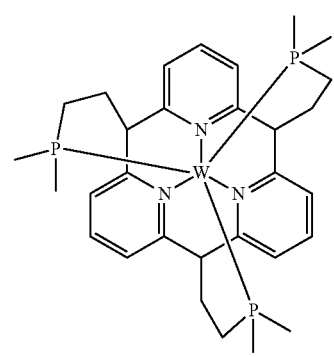 (44)
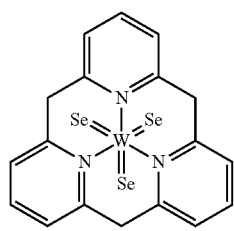 (50)

(51)
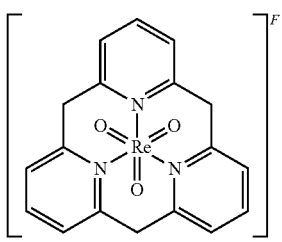
(52)
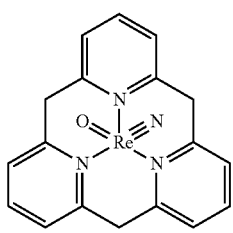
(53)
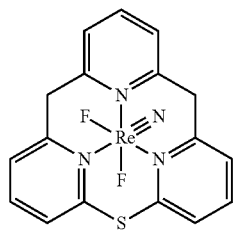
(54)
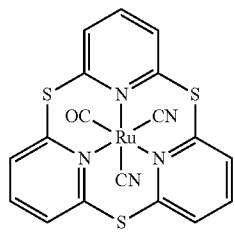
(55)
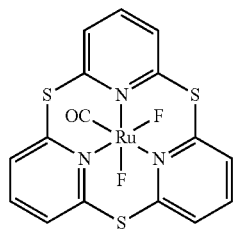
(56)
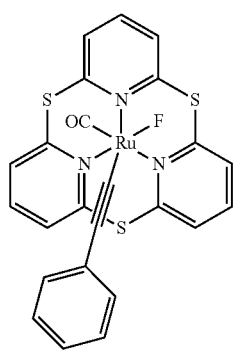
(57)
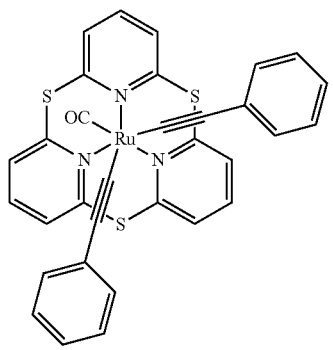
(58)
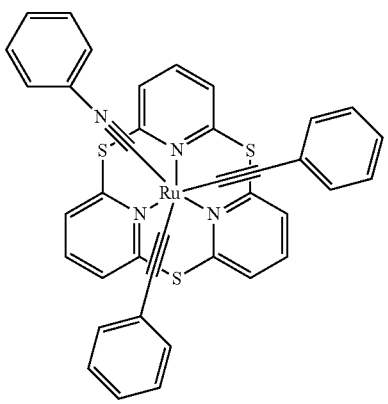
(59)
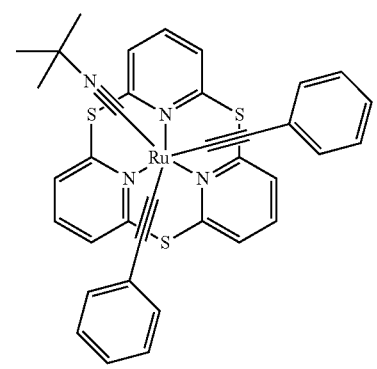
(60)
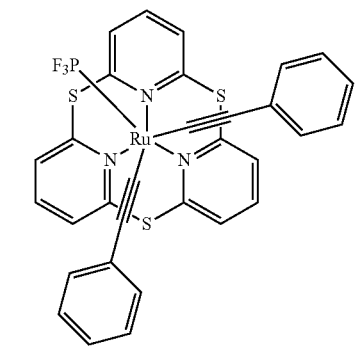

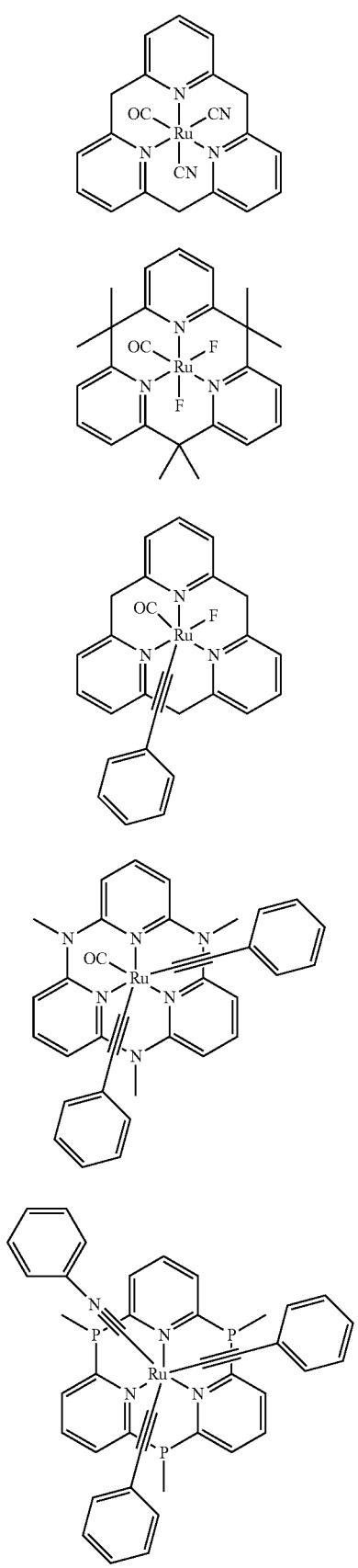
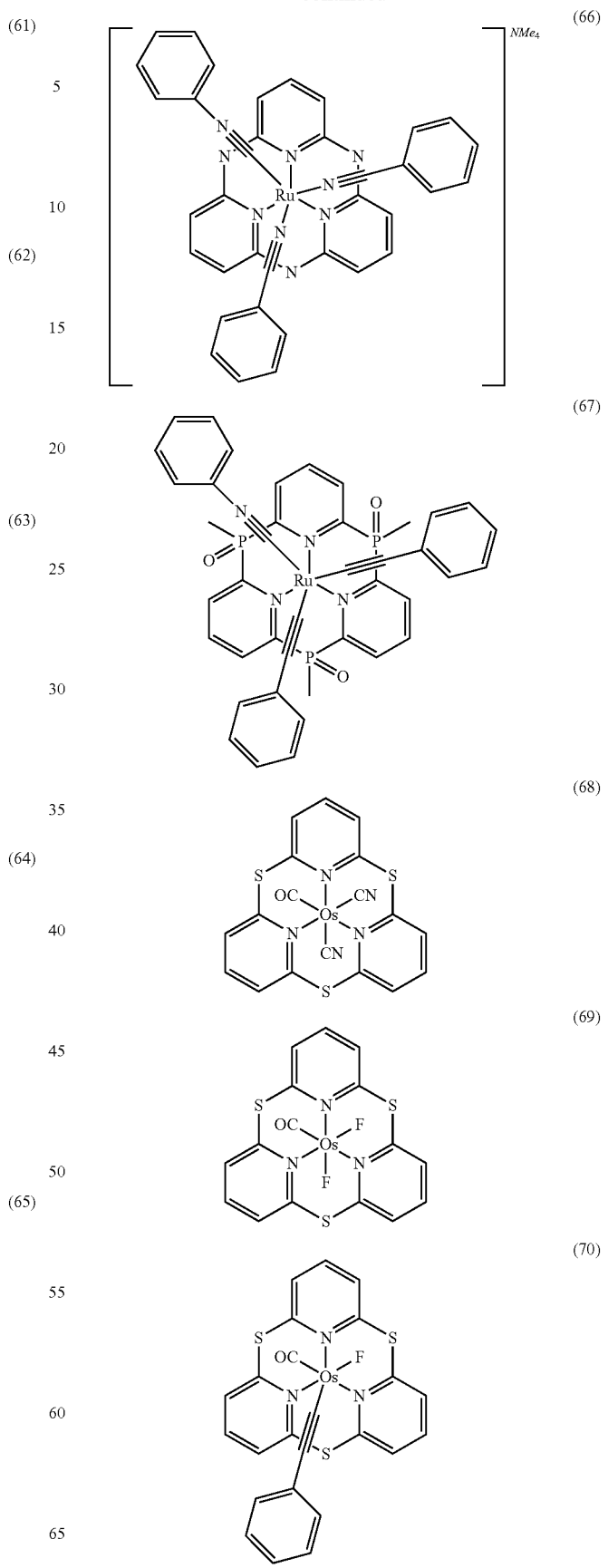

-continued
(71)
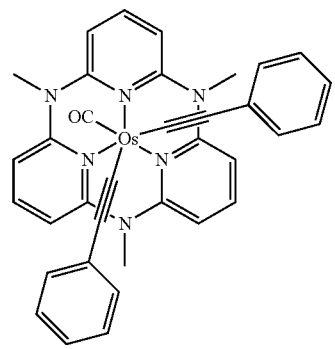
(72)
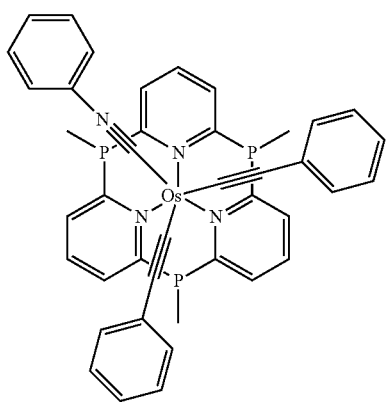
(73)
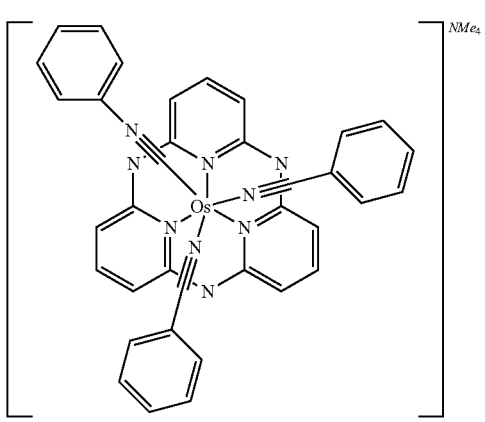
(74)
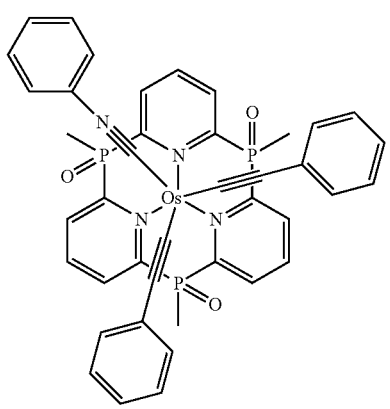
-continued
(75)
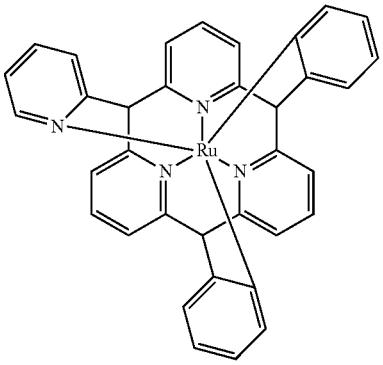
(76)
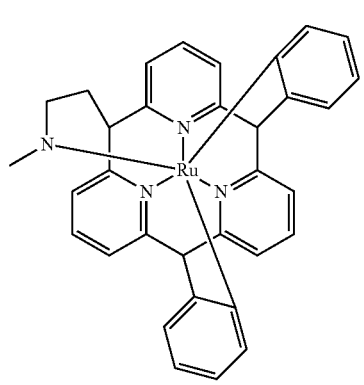
(77)
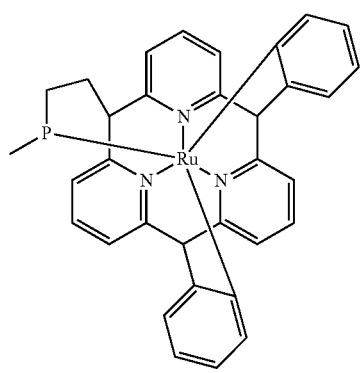
(78)
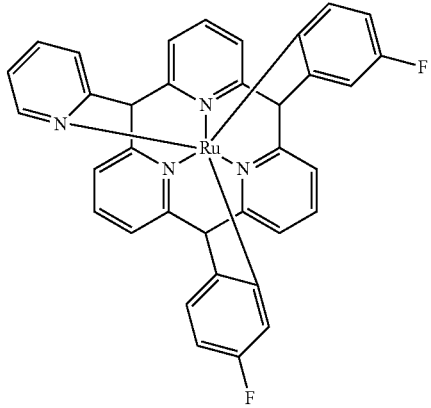

-continued
(79)
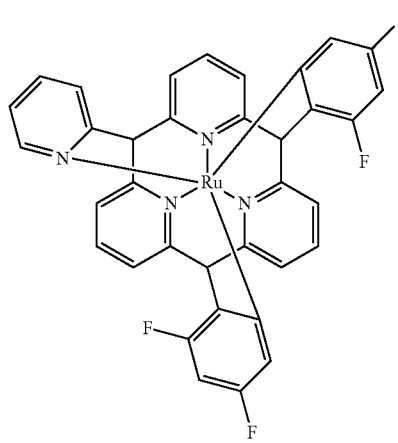
(80)
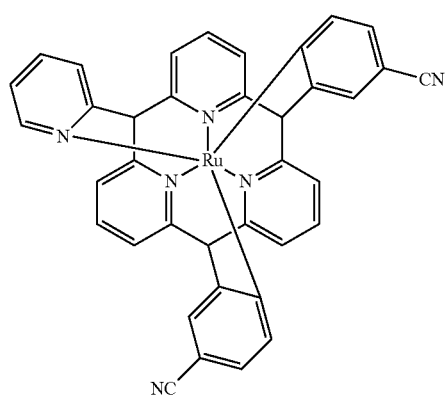
(81)
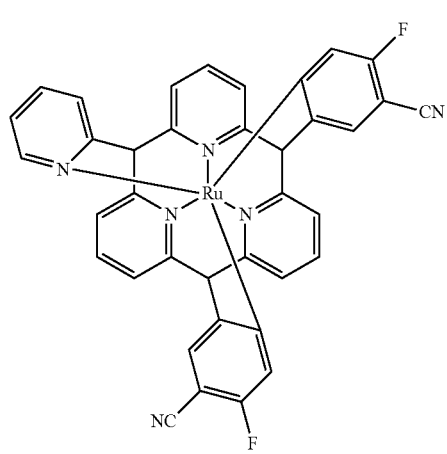
-continued
(82)
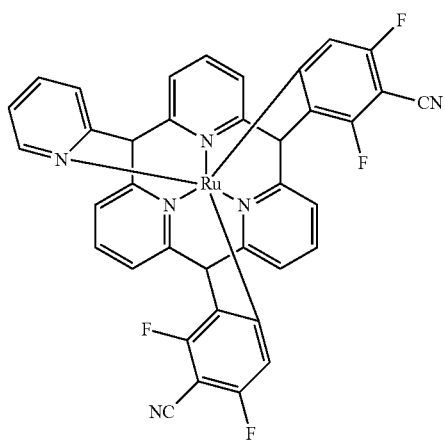
(83)
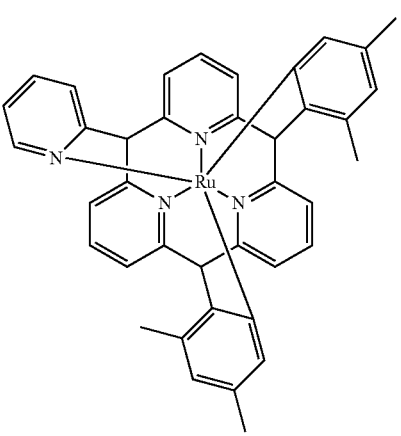
(84)
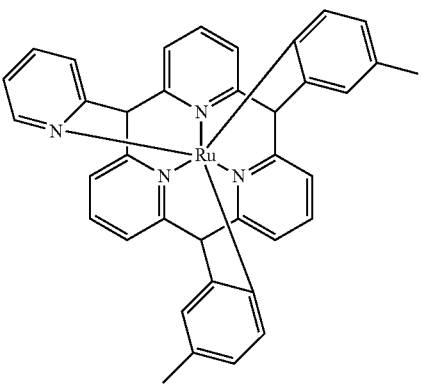

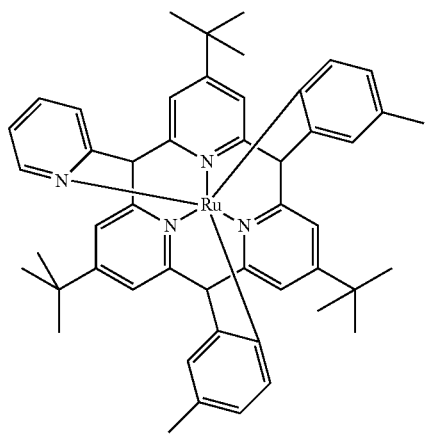
(85)
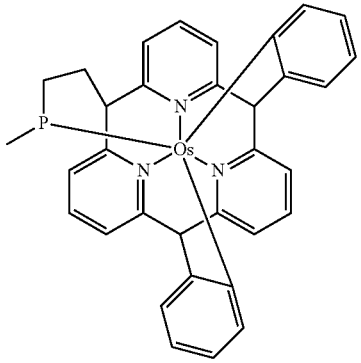
(89)
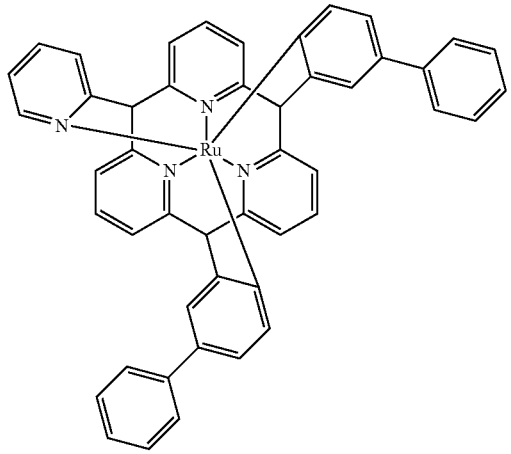
(86)
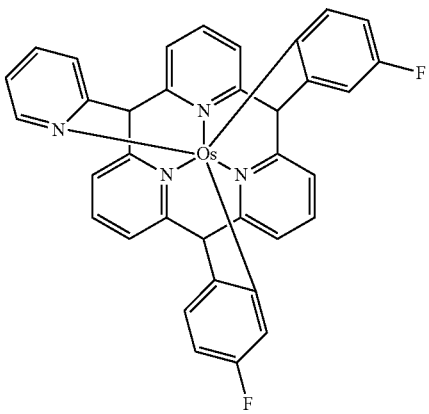
(90)
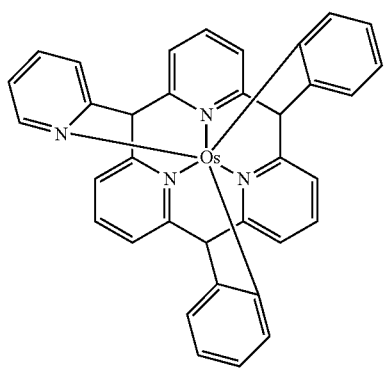
(87)
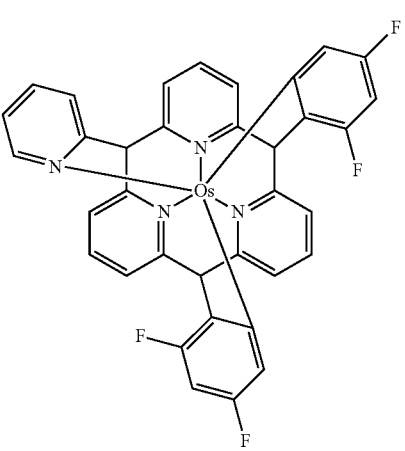
(91)
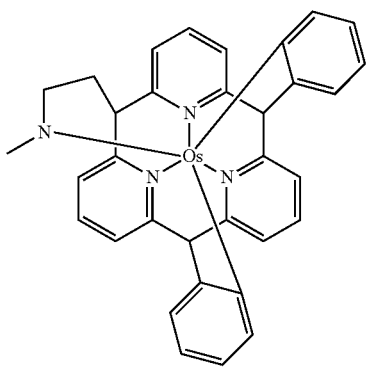
(88)
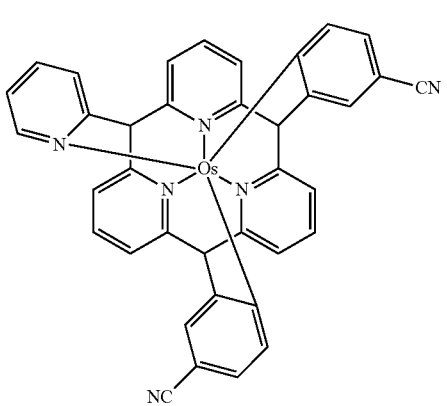
(92)

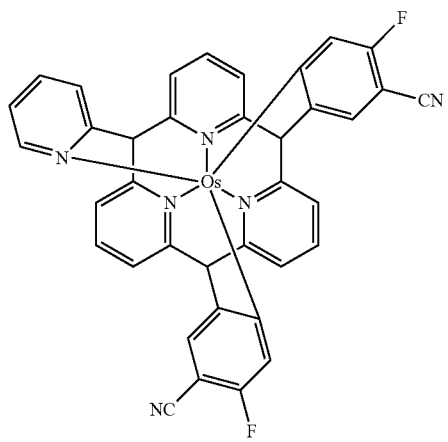
(93)
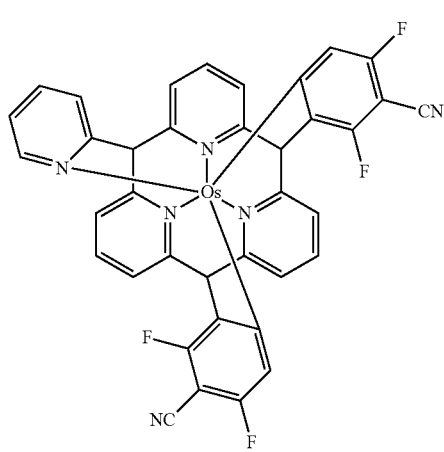
(94)
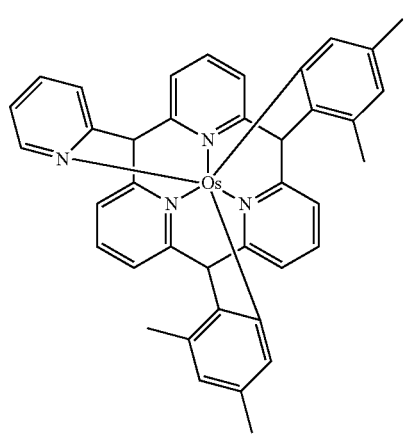
(95)
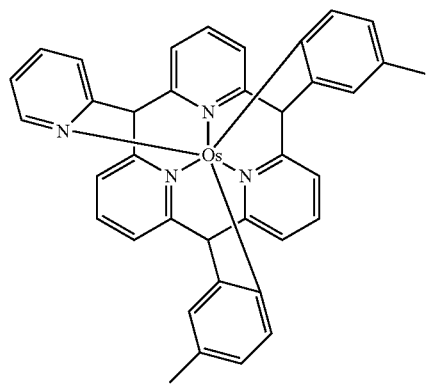
(96)
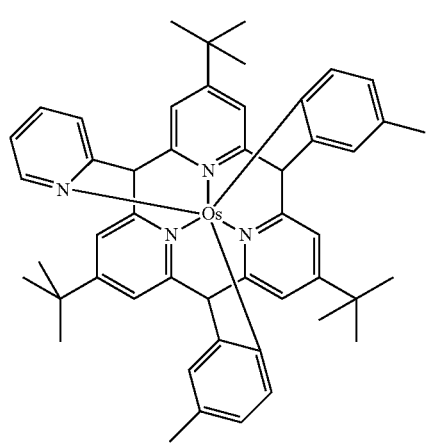
(97)
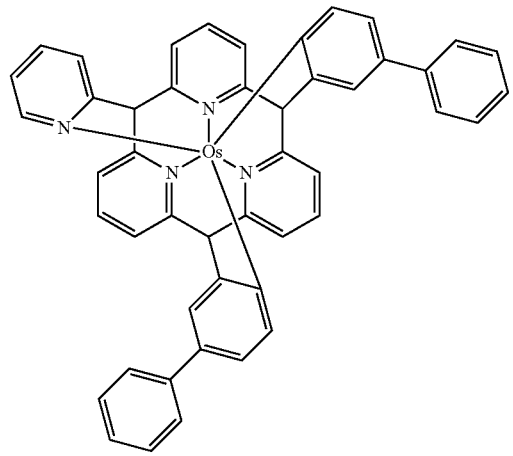
(98)
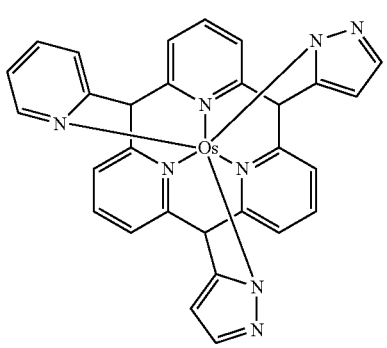
(99)

(100)
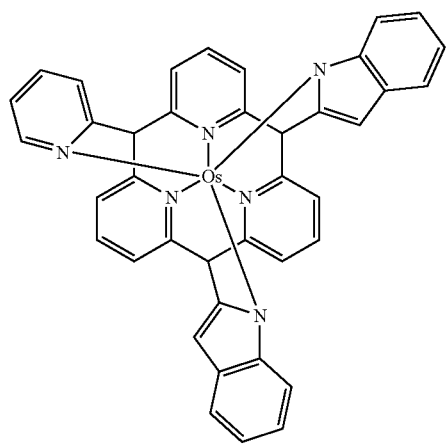
(101)
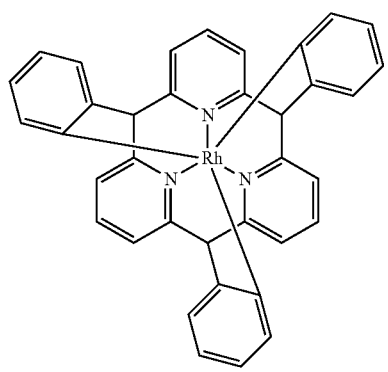
(102)
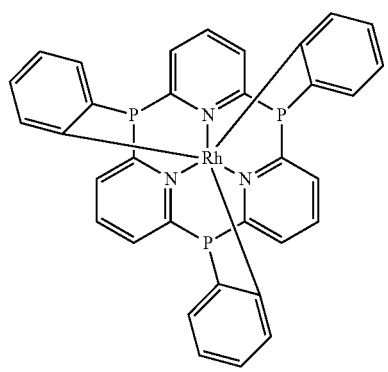
(103)
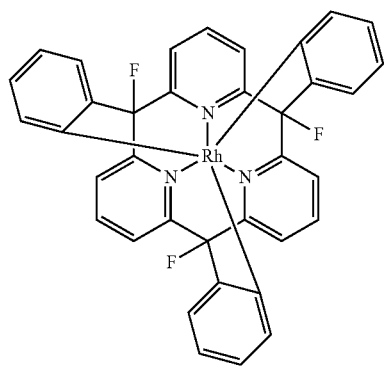
(104)
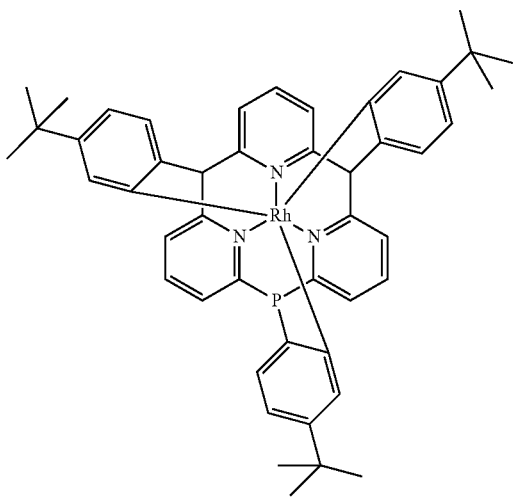
(105)
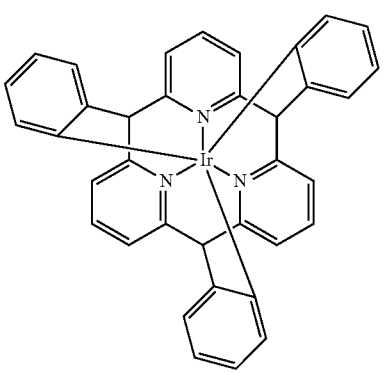
(106)
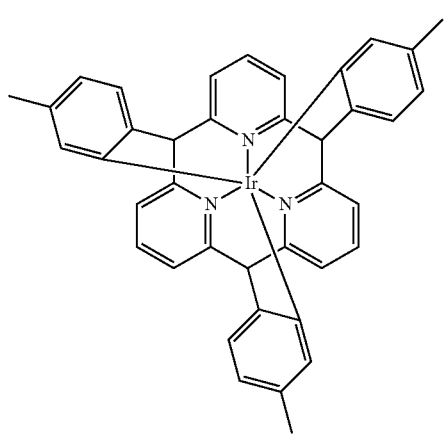

-continued
(107)
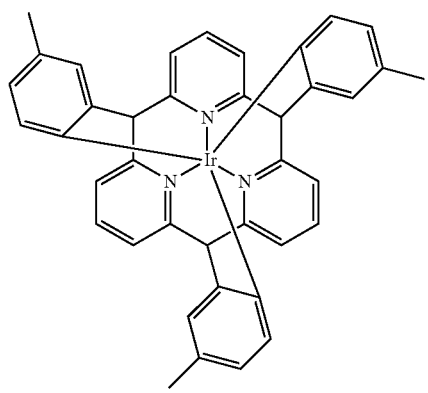
(108)
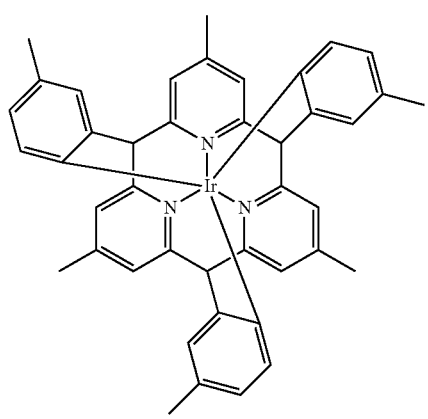
(109)
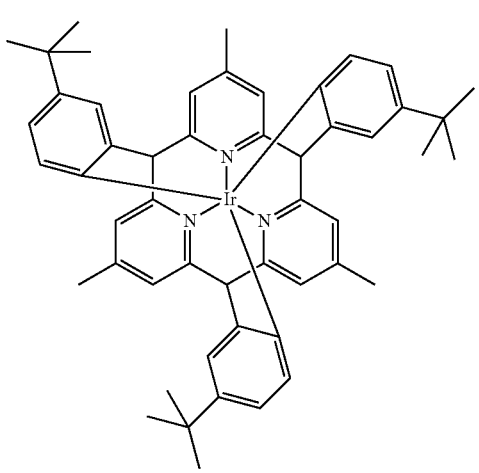
-continued
(110)
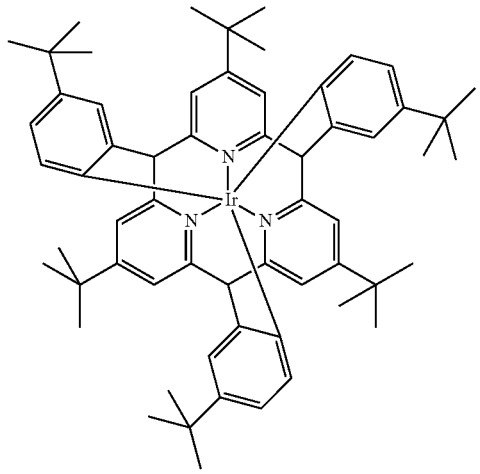
(111)
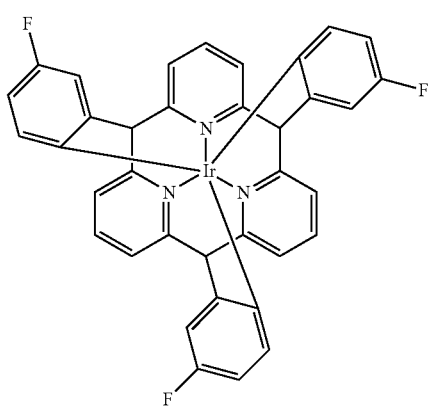
(112)
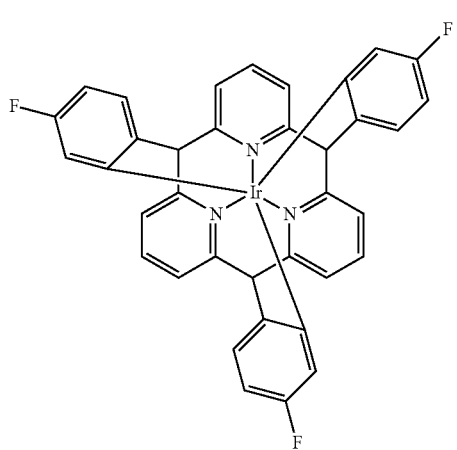

51
-continued
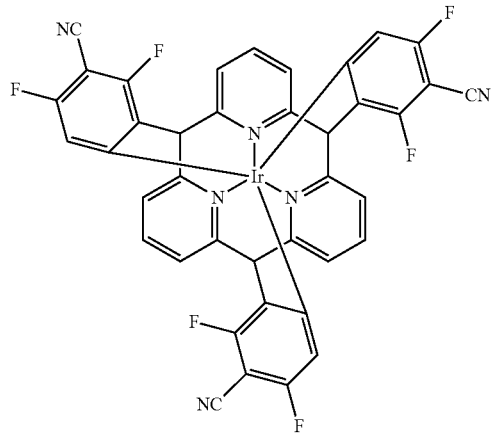
(113)
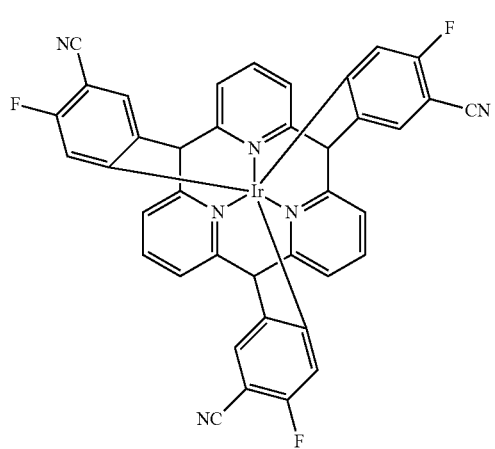
(114)
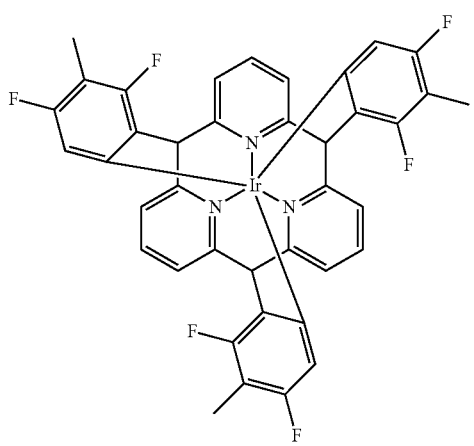
(115)
52
-continued
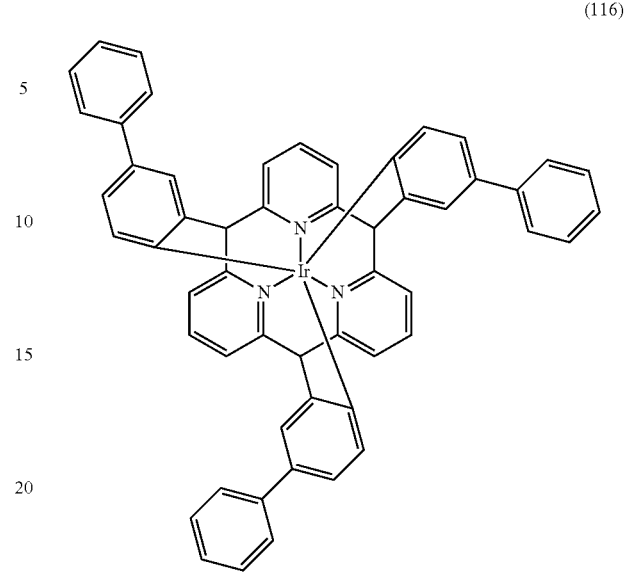
(116)
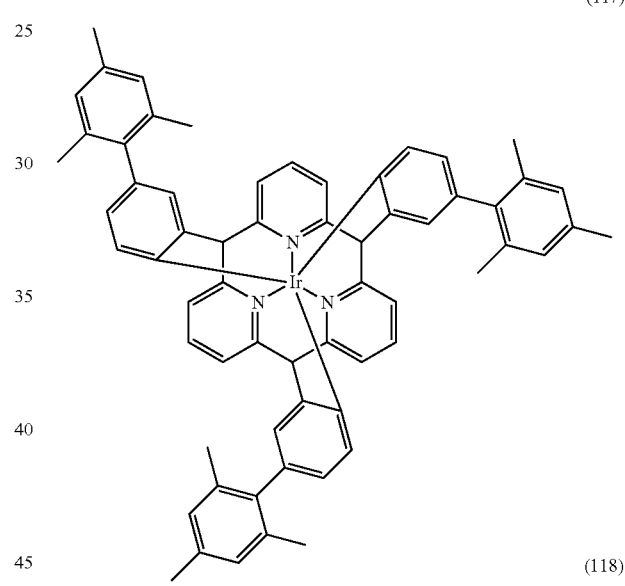
(117)
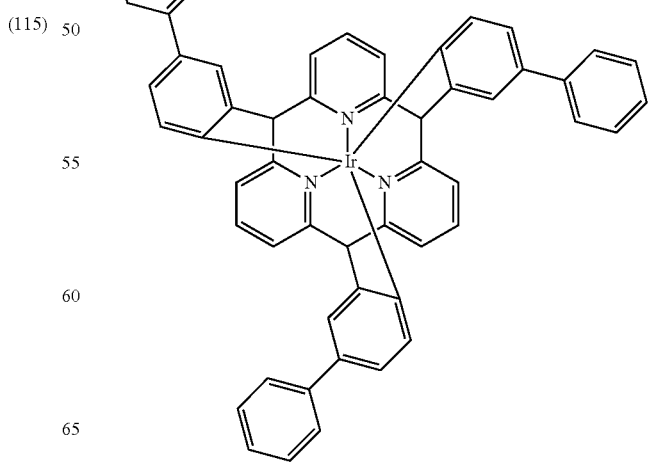
(118)

(119)
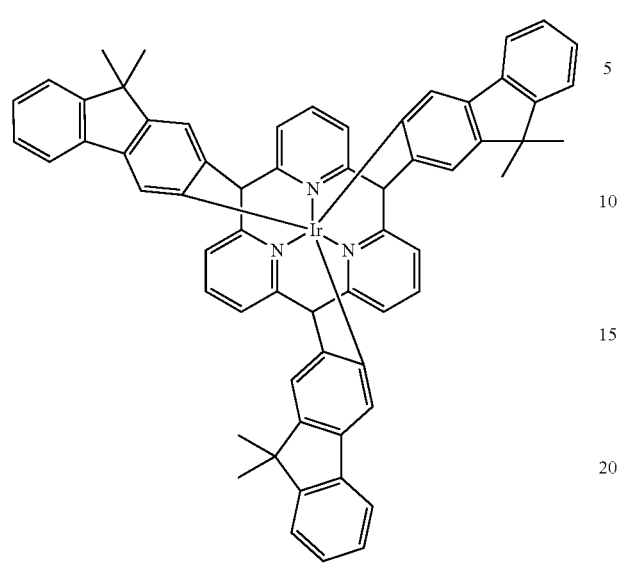
(120)
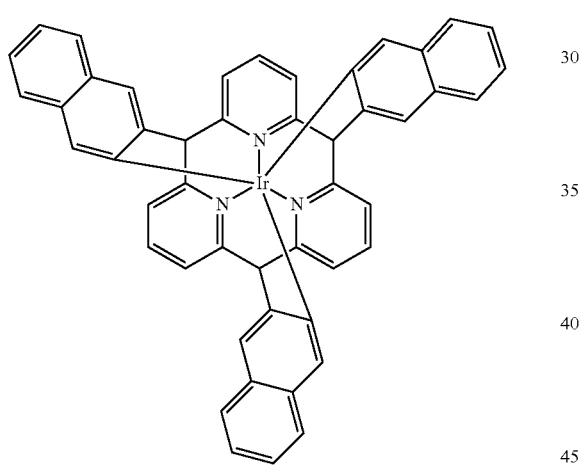
(121)
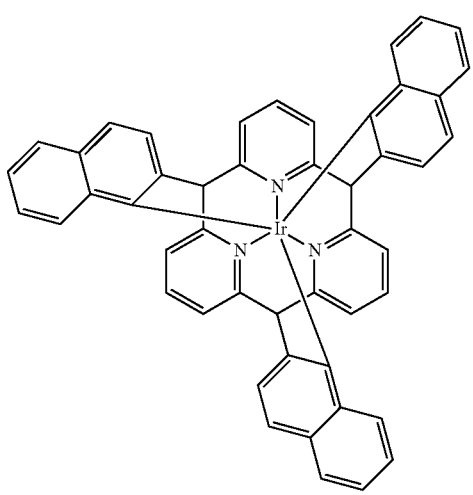
(122)
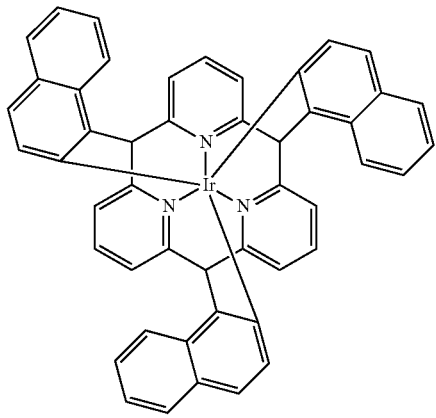
(123)
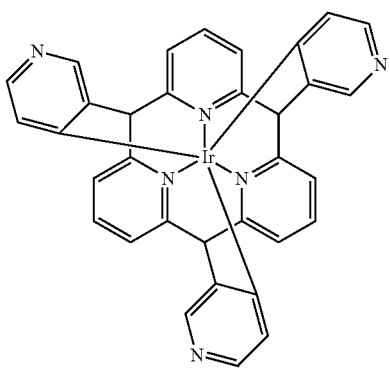
(124)
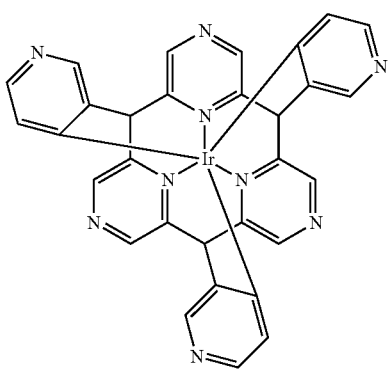
(125)
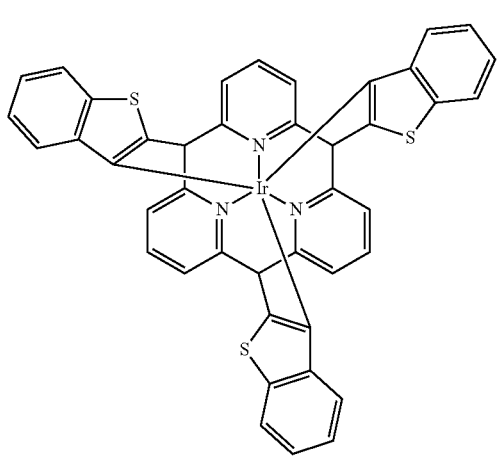

(126)
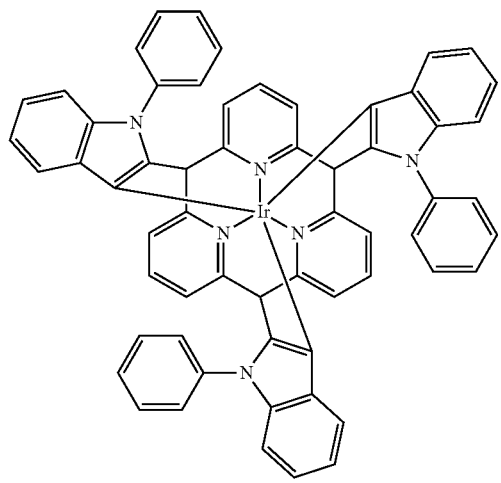
(127)
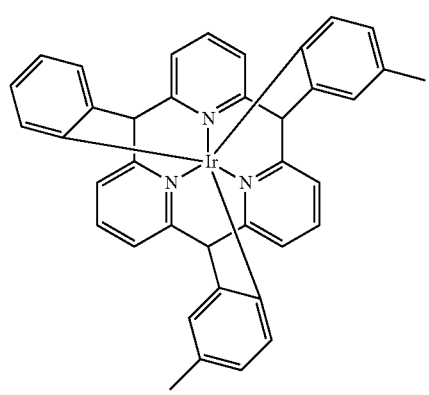
(128)
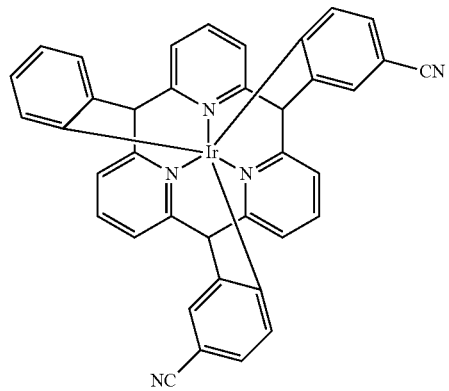
(129)
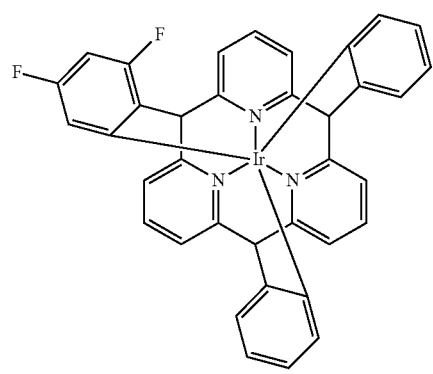
(130)
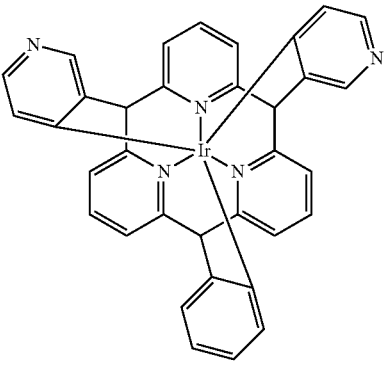
(131)
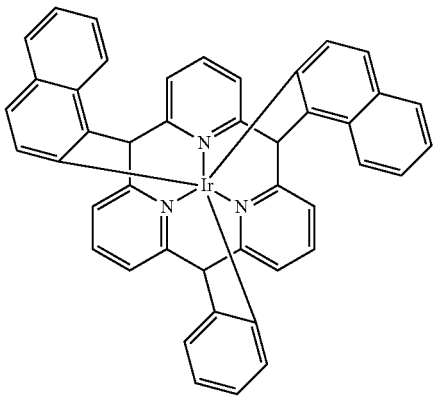
(132)
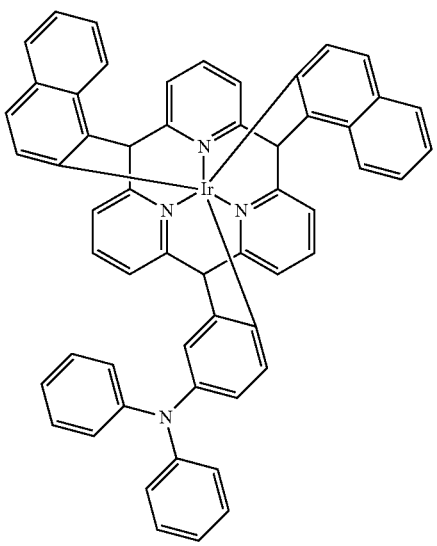
(133)
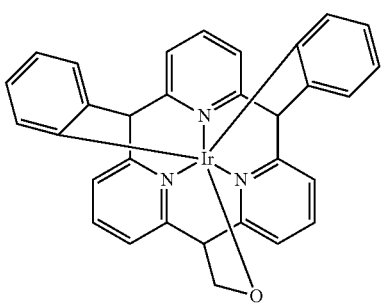

(134) 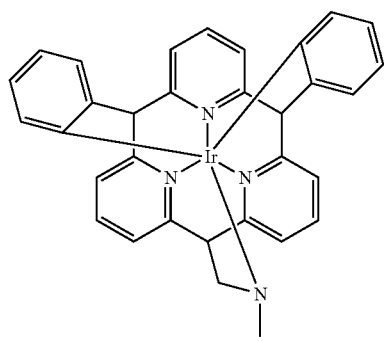
(135) 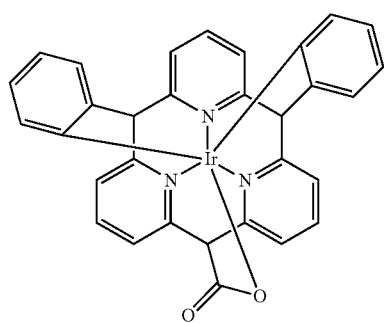
(136) 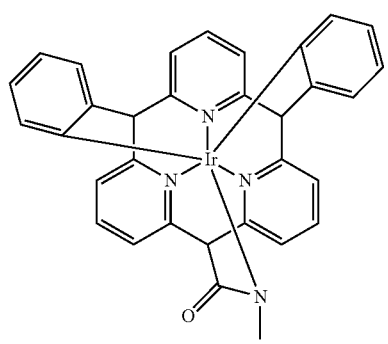
(137) 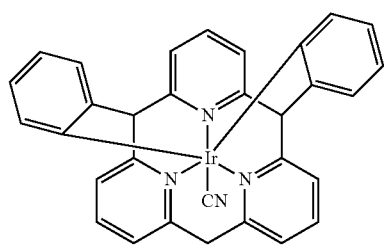
(138) 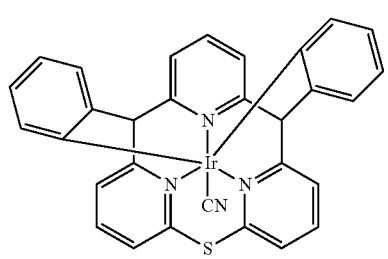
(139) 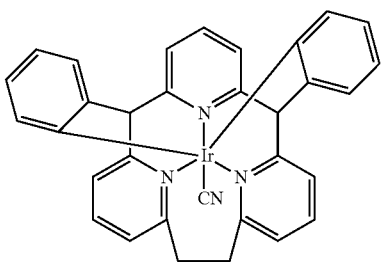
(140) 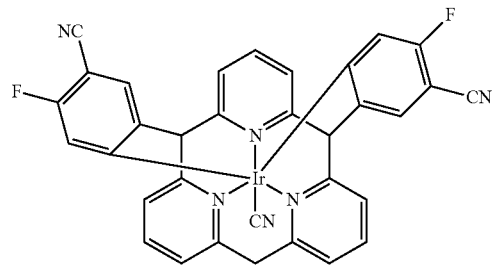
(141) 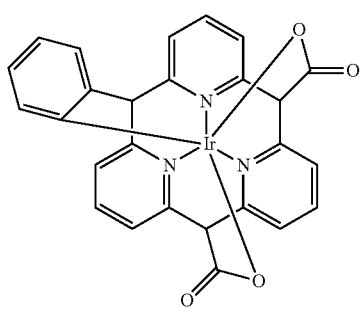
(142) 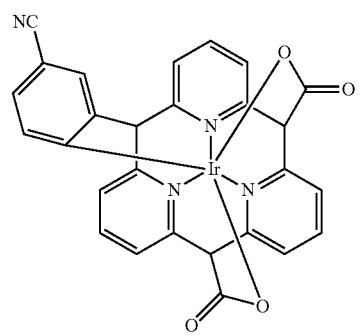
(143) 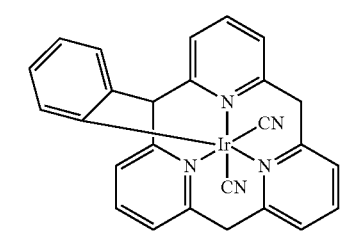
(144) 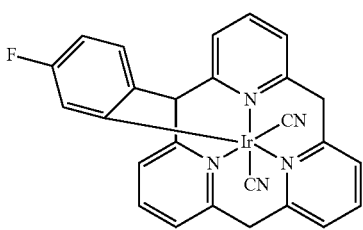

-continued
(145)
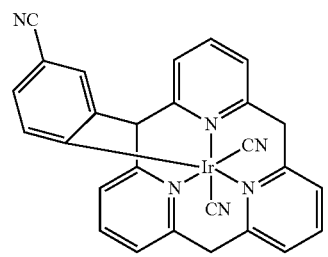
(146)
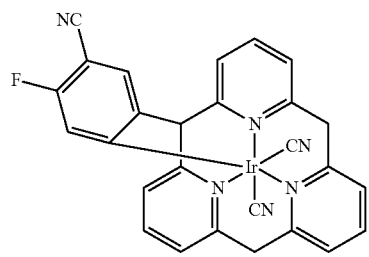
(147)
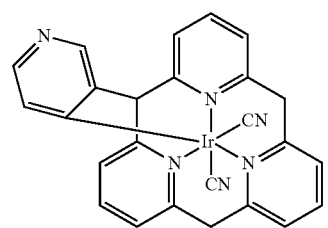
(148)
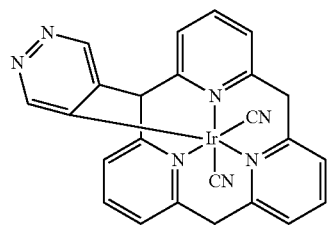
(149)
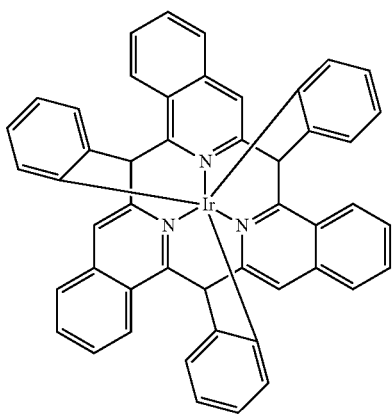
(150)
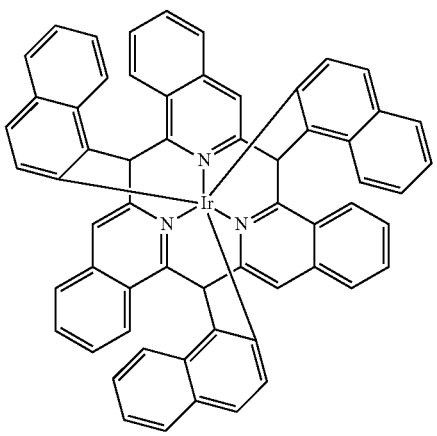
(151)
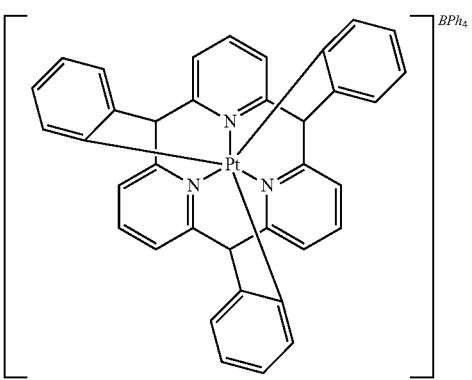
(152)
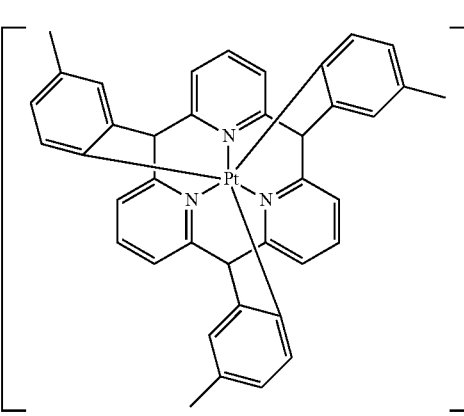
(153)
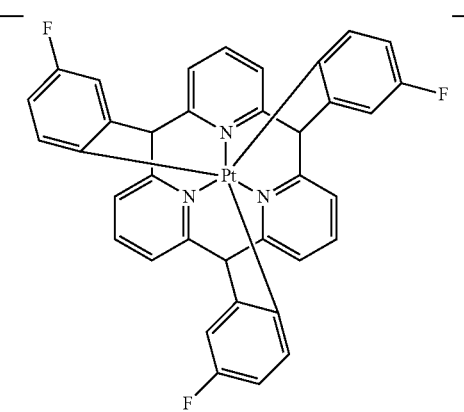

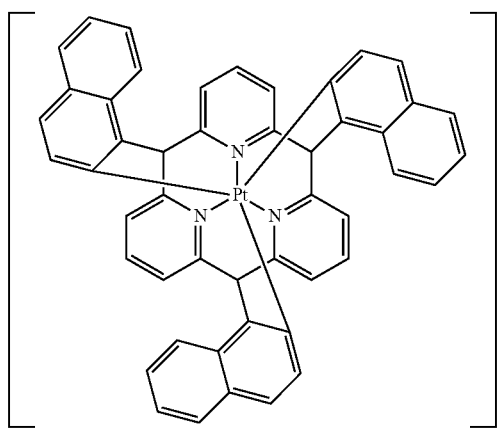
(154)
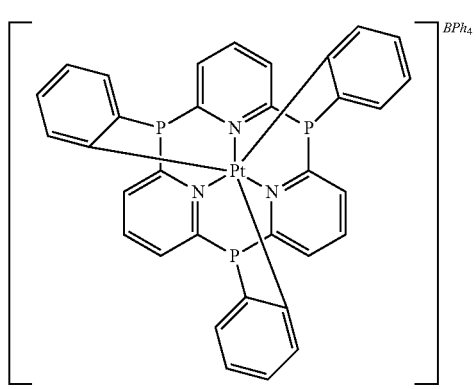
(155)
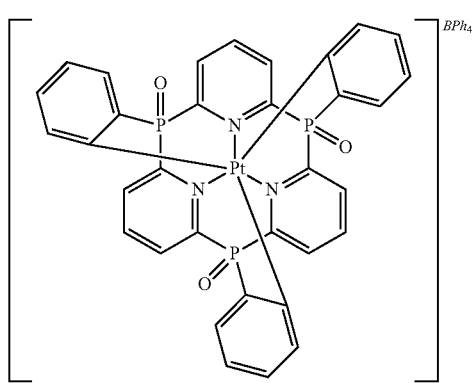
(156)
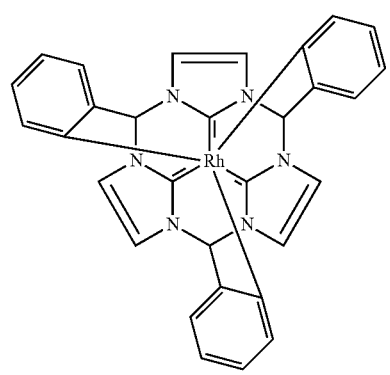
(157)
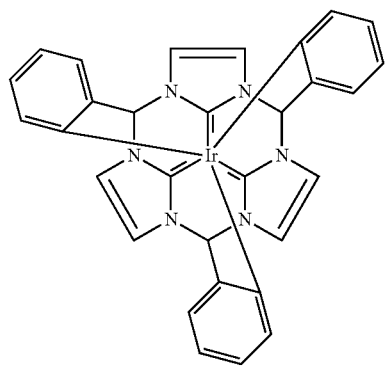
(158)
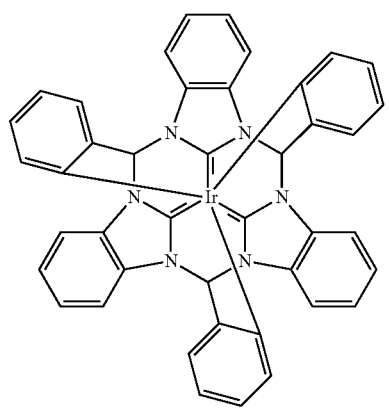
(159)
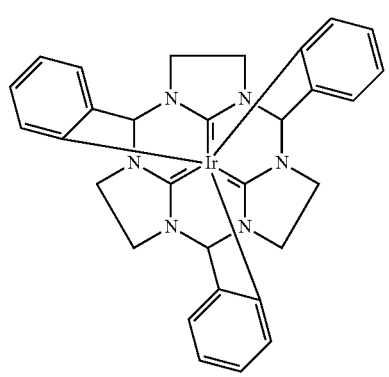
(160)
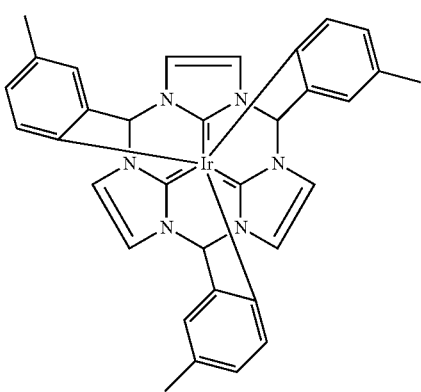
(161)

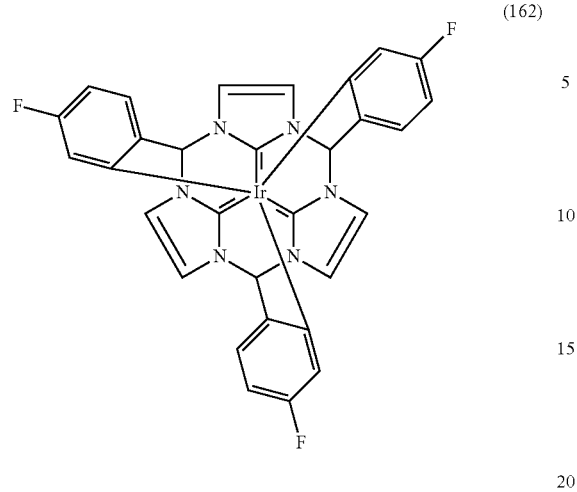
(162)
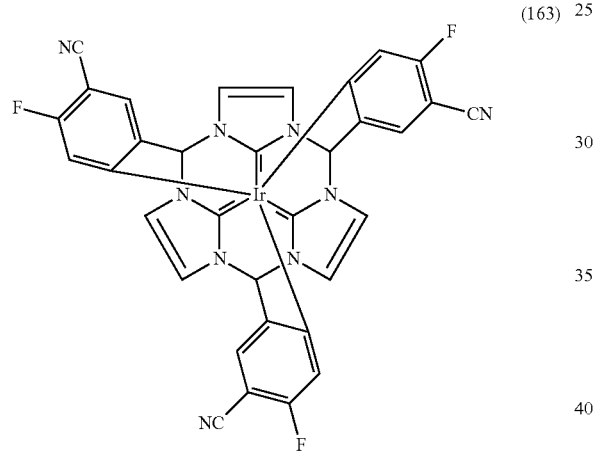
(163)
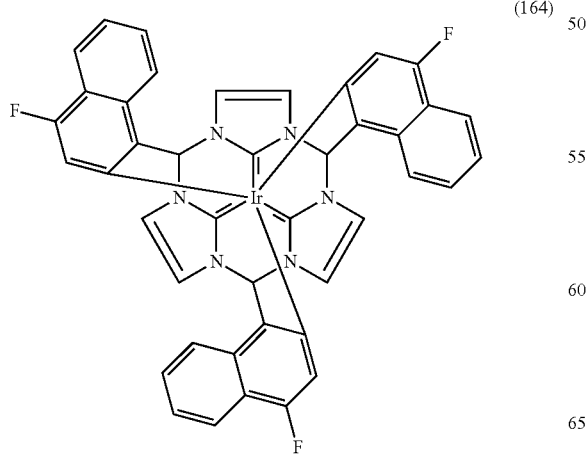
(164)
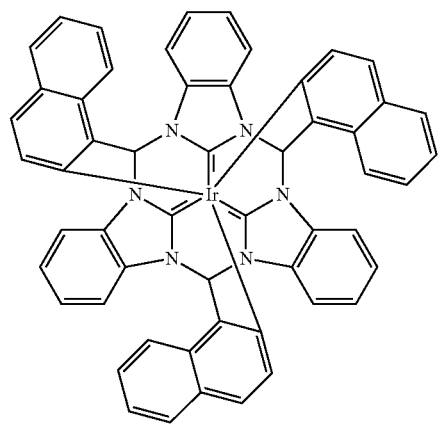
(165)
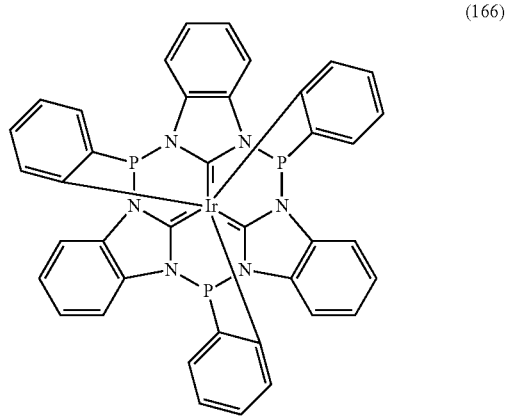
(166)
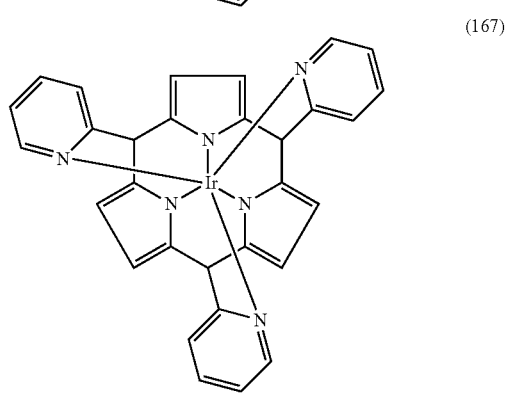
(167)
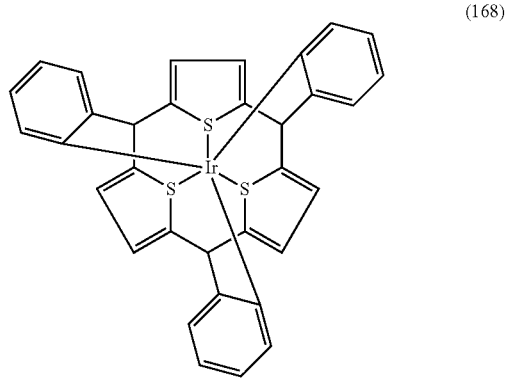
(168)

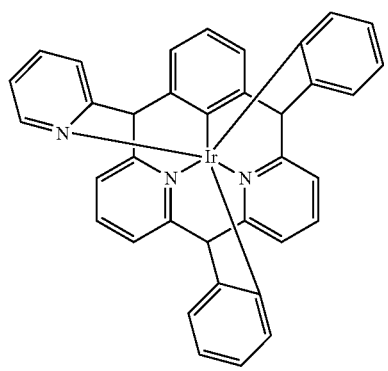
(169)
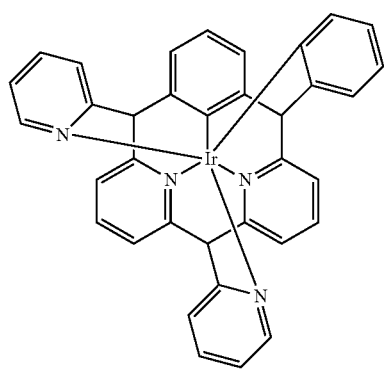
(170)
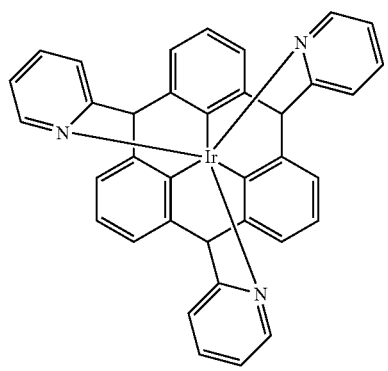
(171)
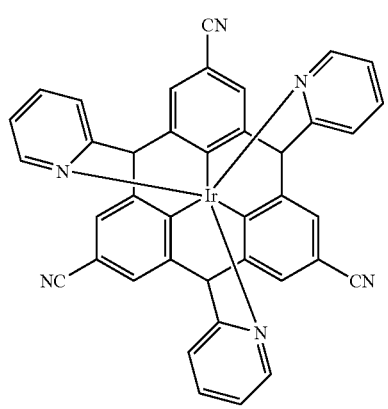
(172)
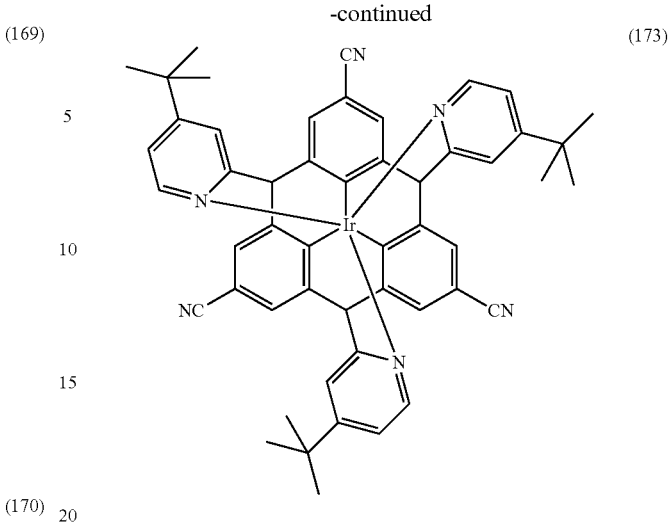
(173)
(174)
(175)

(176)
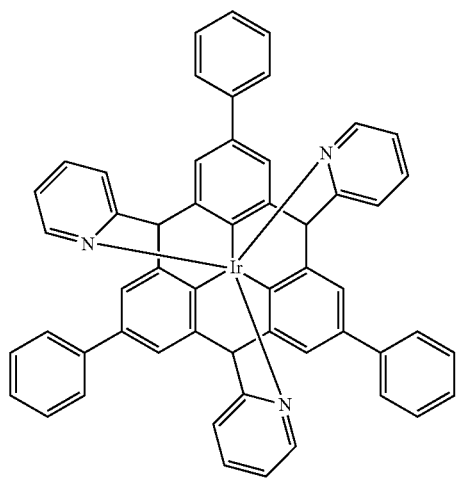
(177)
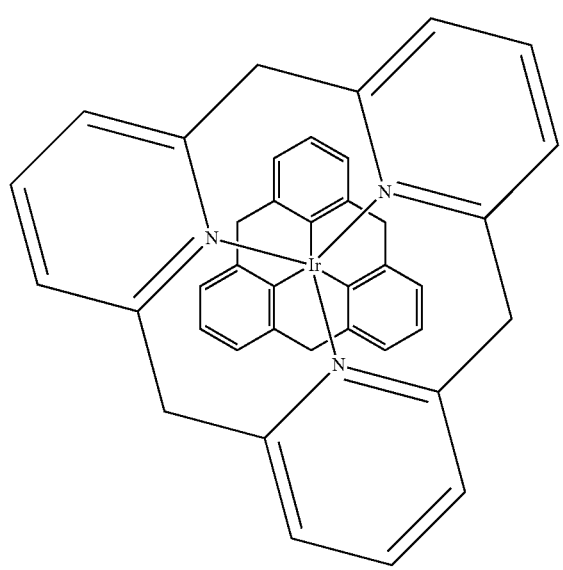
(178)
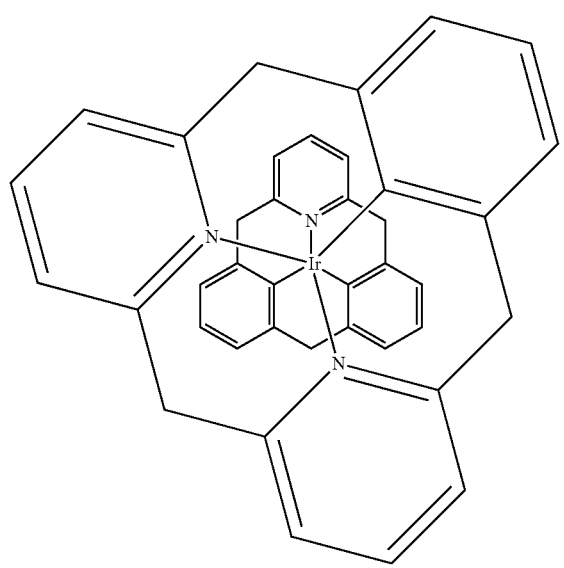
(179)
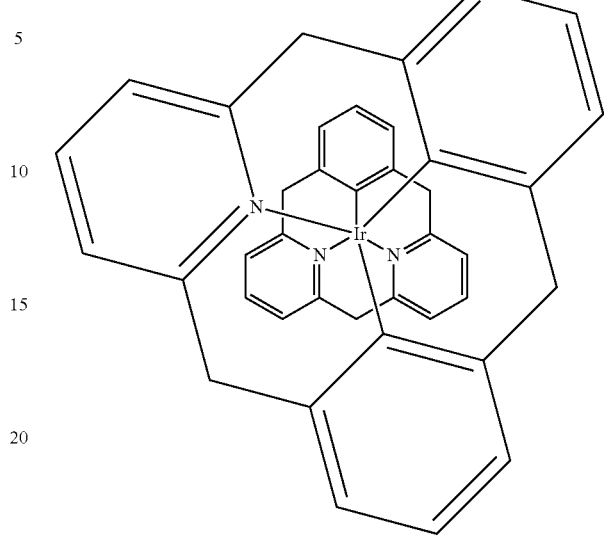
(180)
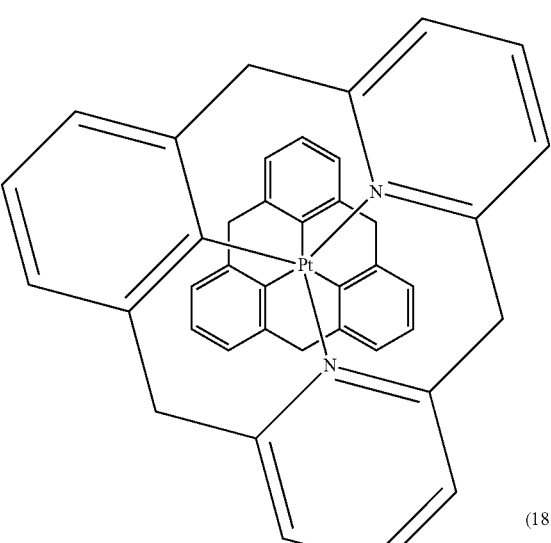
(181)
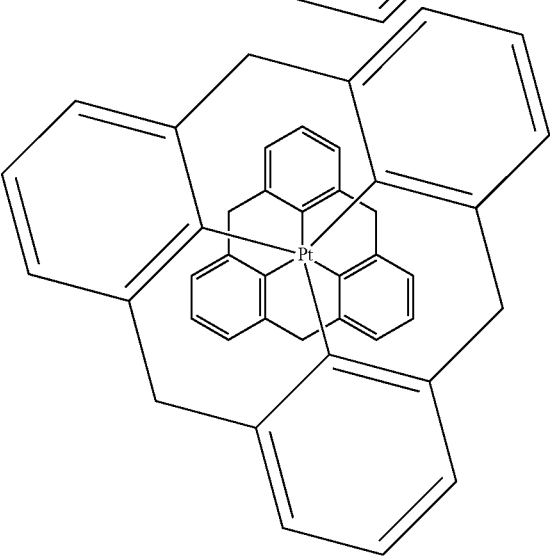

69
-continued
(182)
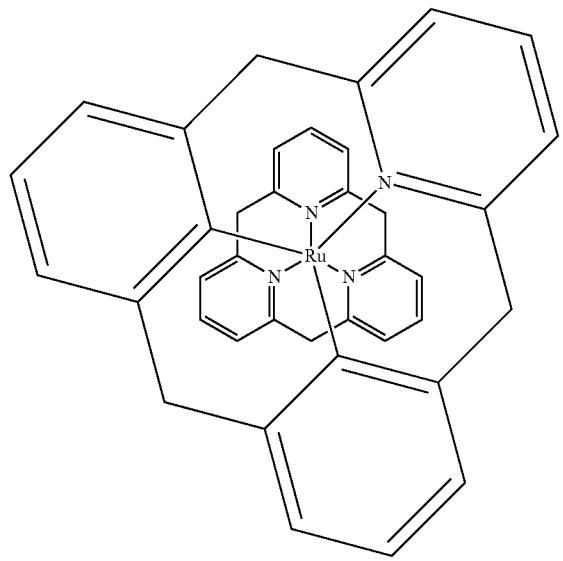
(183)
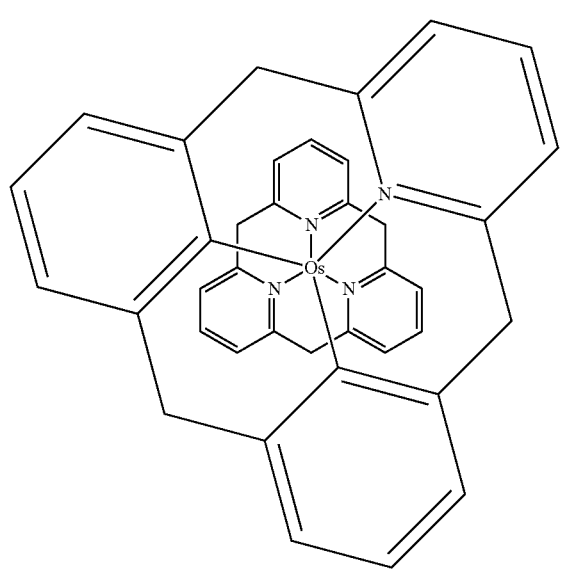
70
-continued
(184)
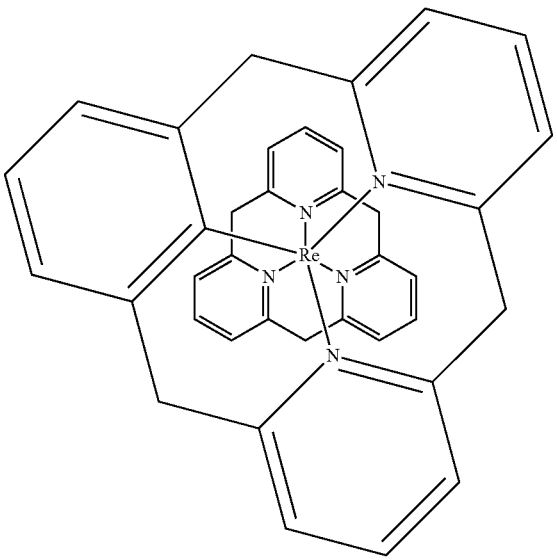
(185)
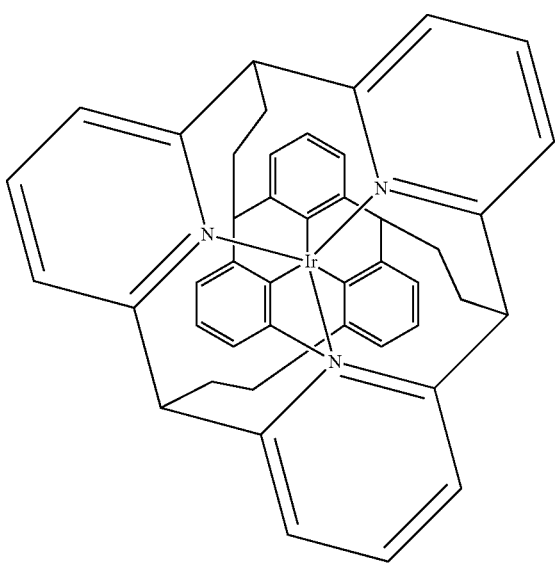

-continued
(186)
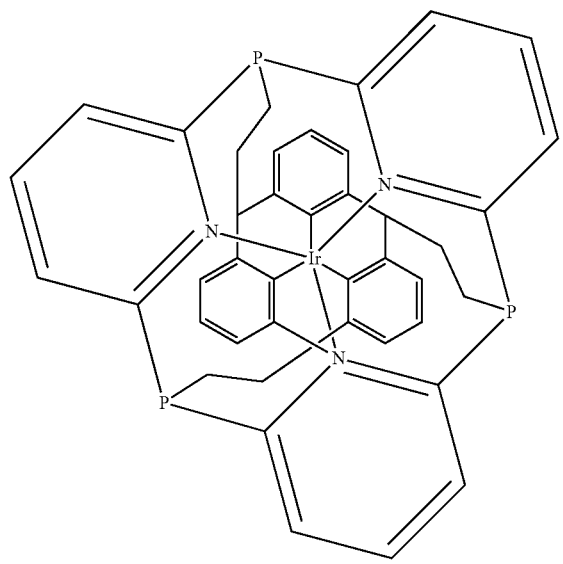
(187)
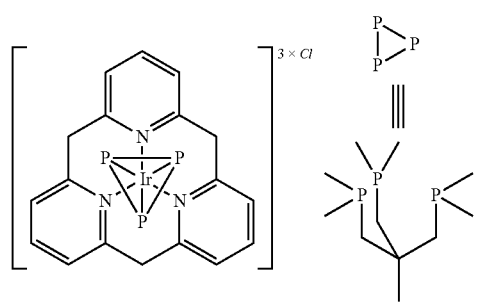
(188)
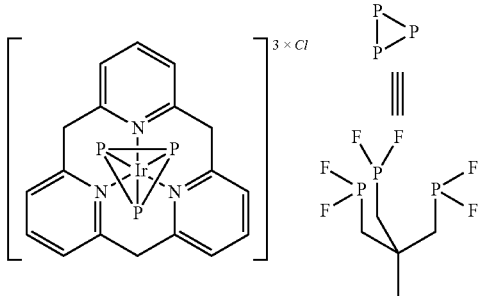
(189)
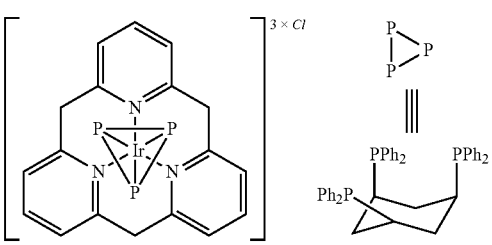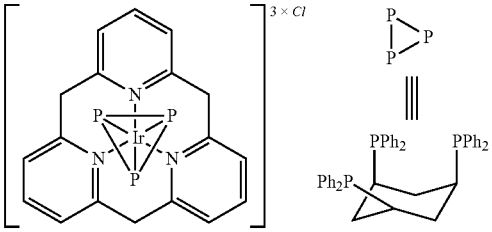
-continued
(190)
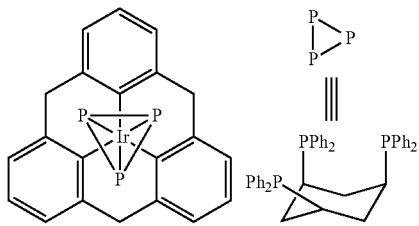
(191)
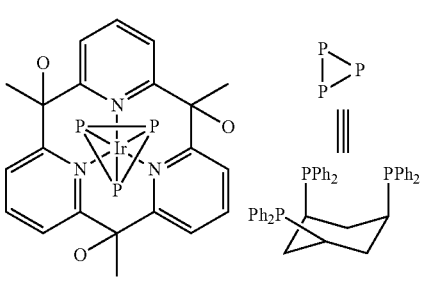
(192)
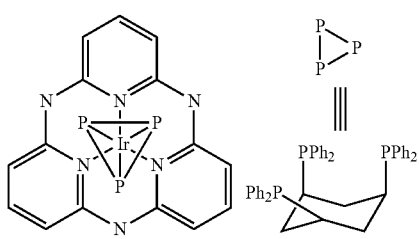
(193)
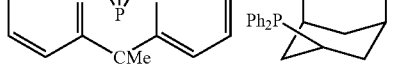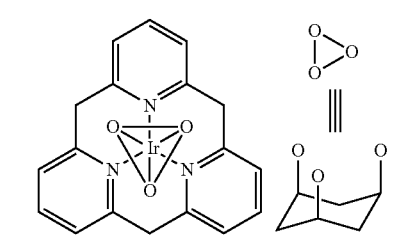
(194)
(195)
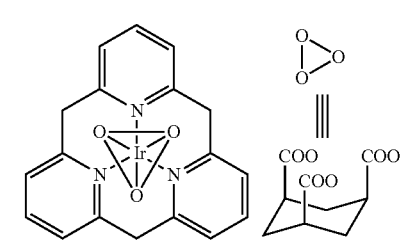

(196) 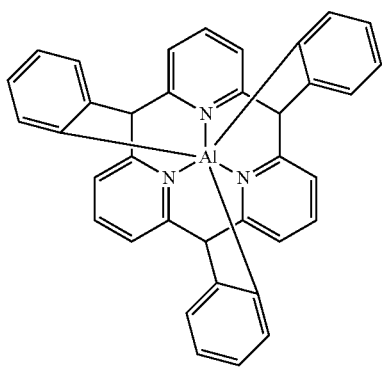
(197) 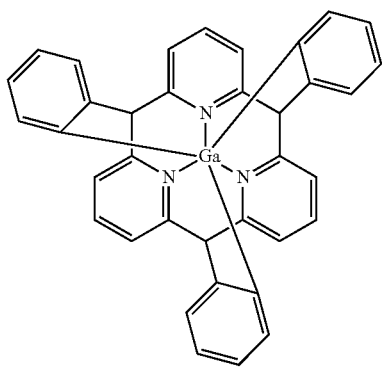
(198) 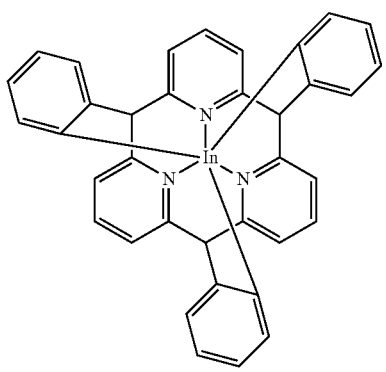
(199) 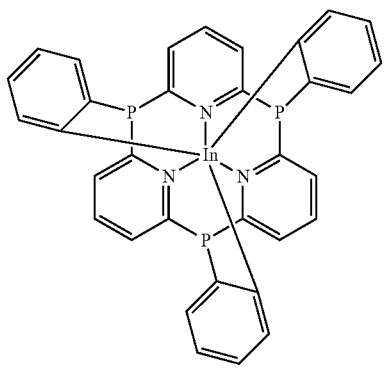
(200) 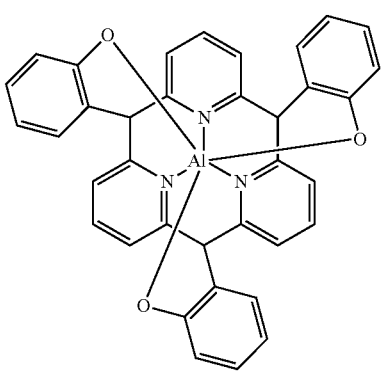
(201) 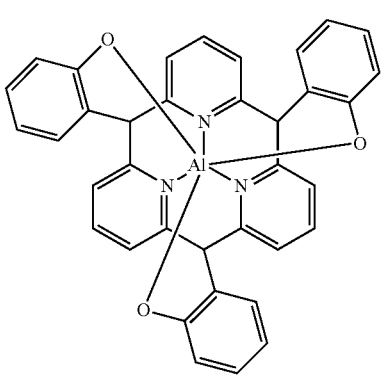
(202) 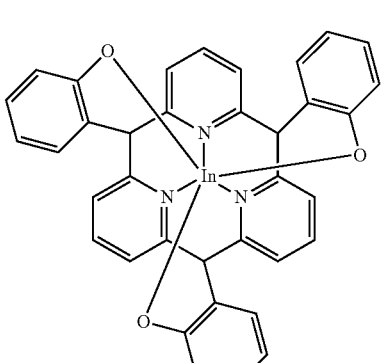
(203) 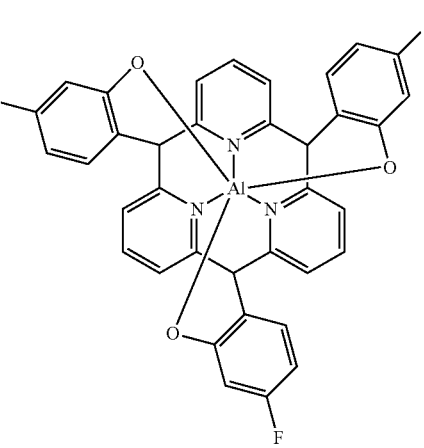

-continued
(204)
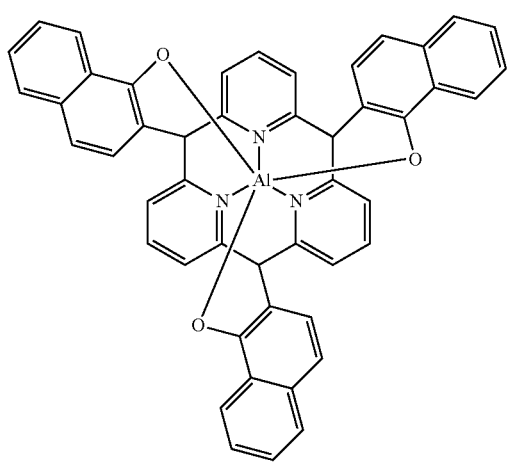
(205)
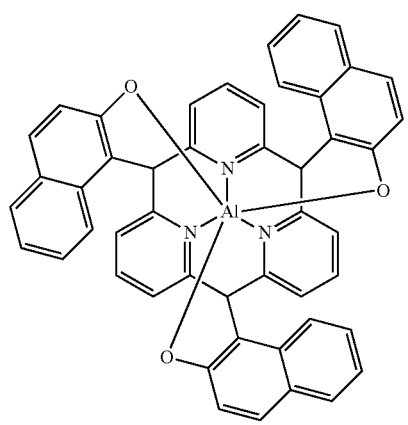
(206)
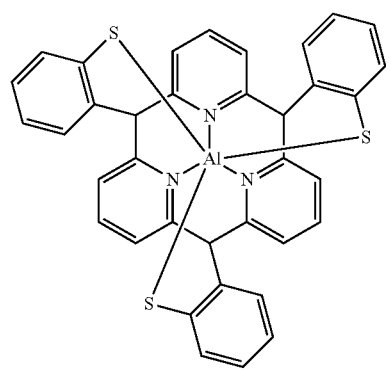
(207)
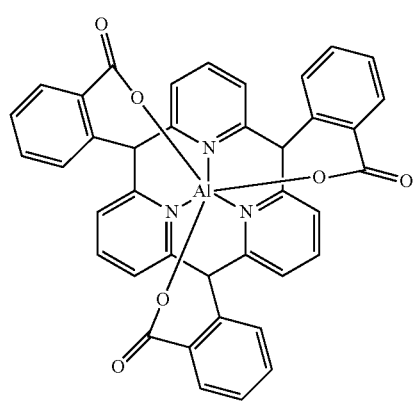
-continued
(208)
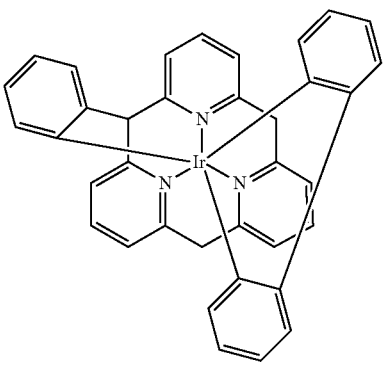
(209)
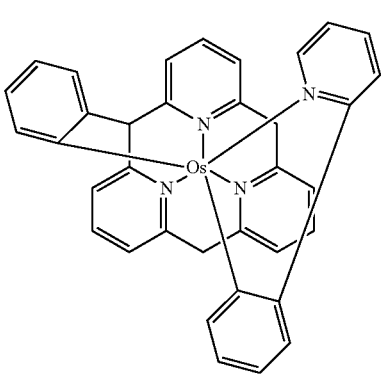
(210)
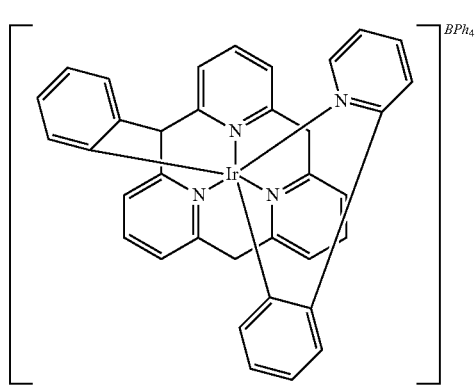
(211)
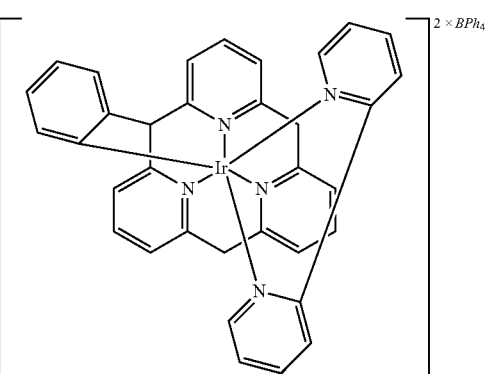

(212)
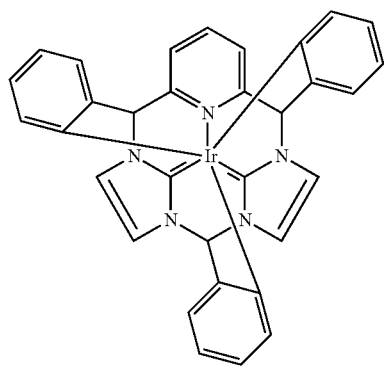
(213)
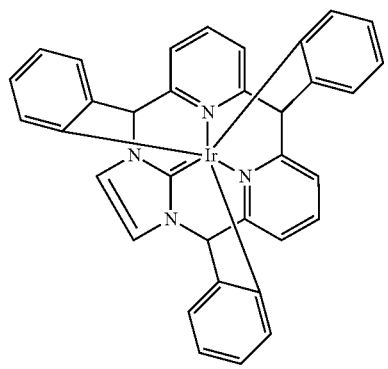
(214)
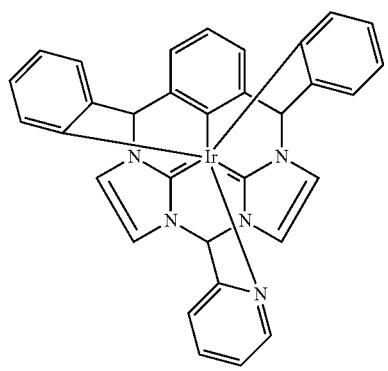
(215)
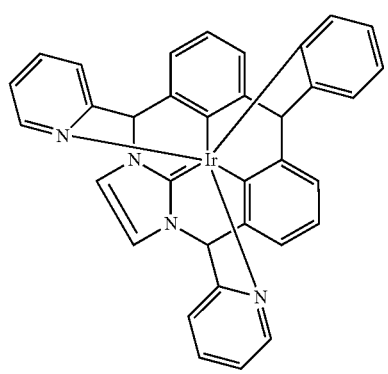
(216)
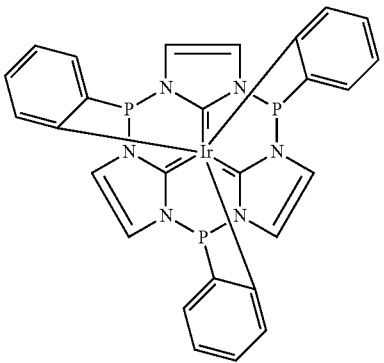
(217)
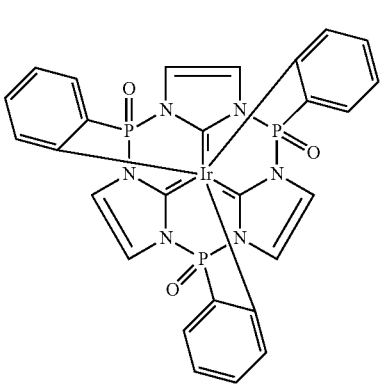
(218)
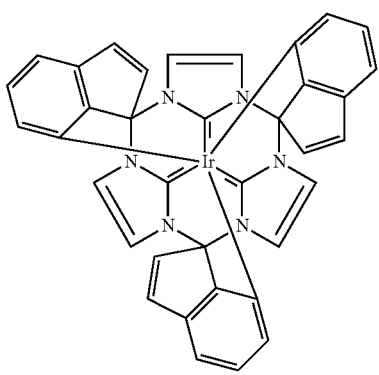
(219)
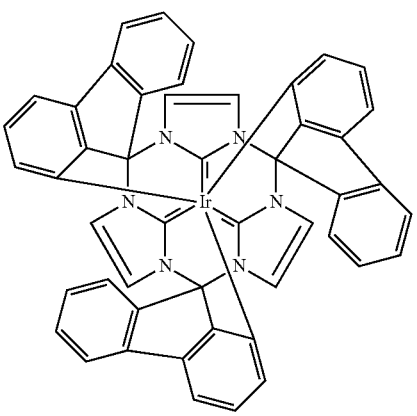

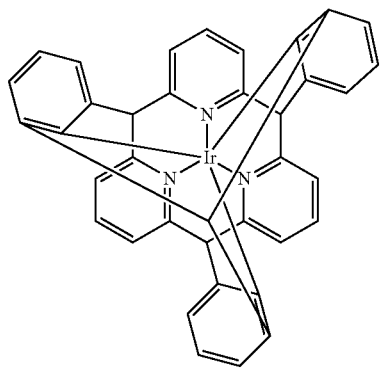
(220)
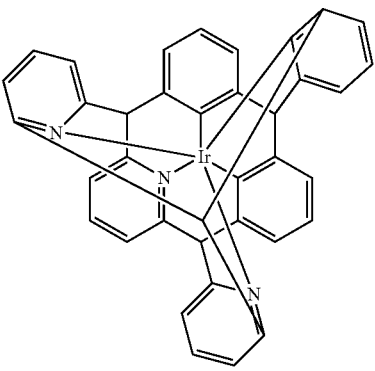
(224)
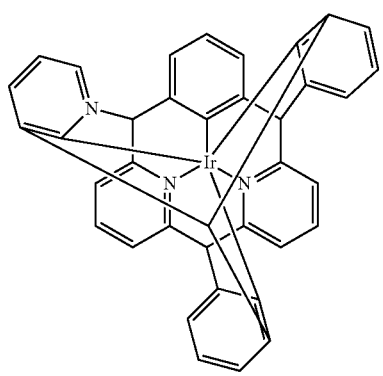
(221)
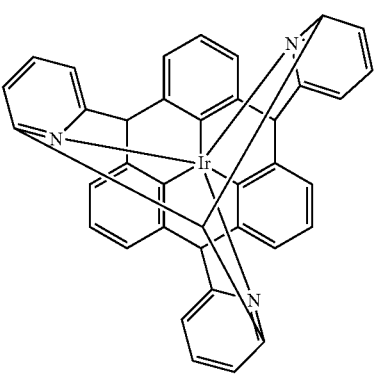
(225)
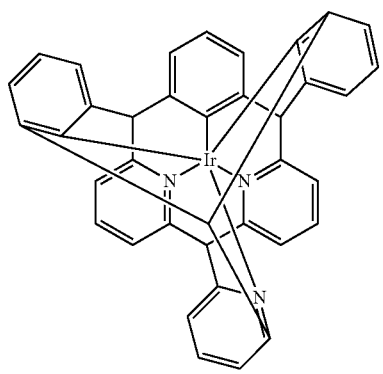
(222)
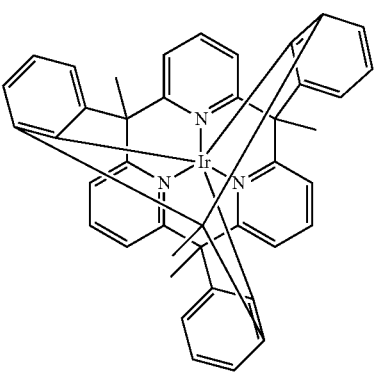
(226)
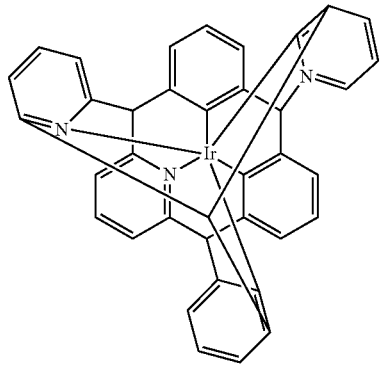
(223)
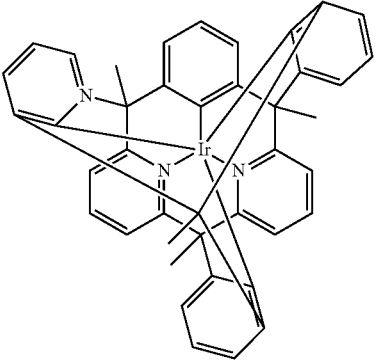
(227)

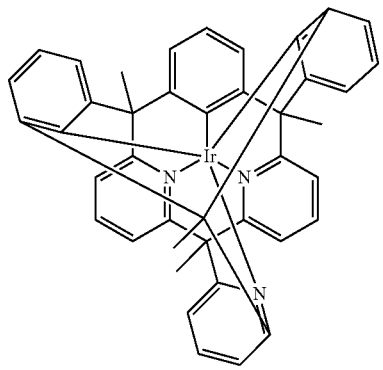
(228)
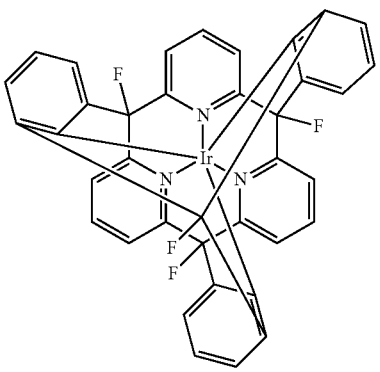
(232)
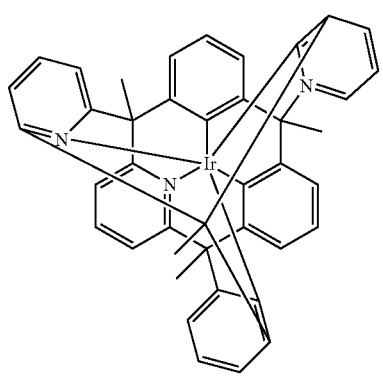
(229)
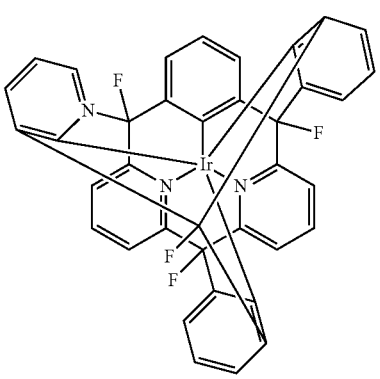
(233)
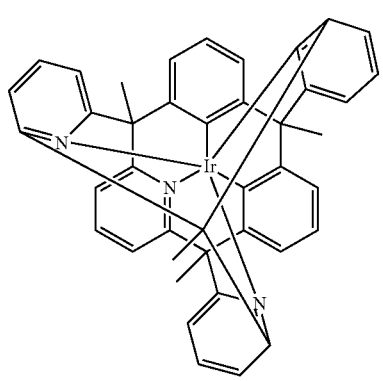
(230)
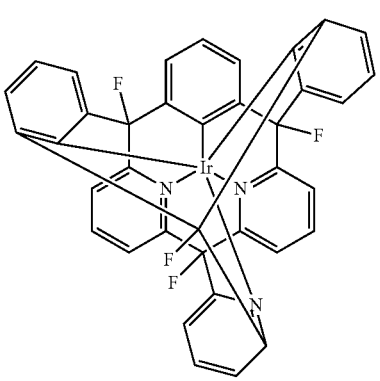
(234)
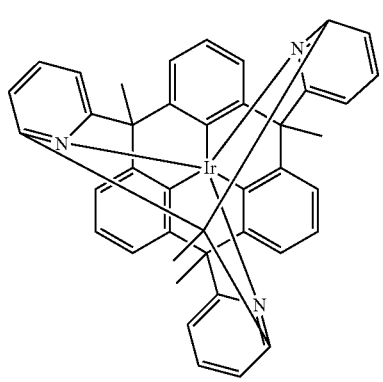
(231)
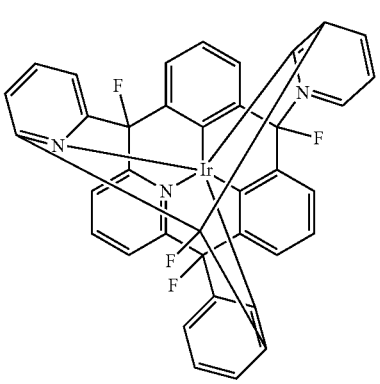
(235)

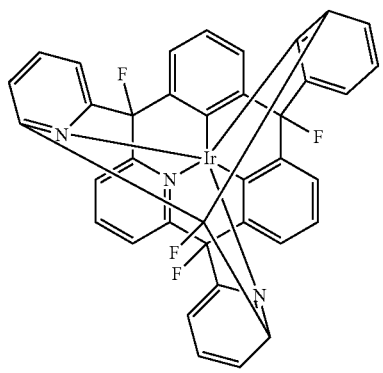 (236)
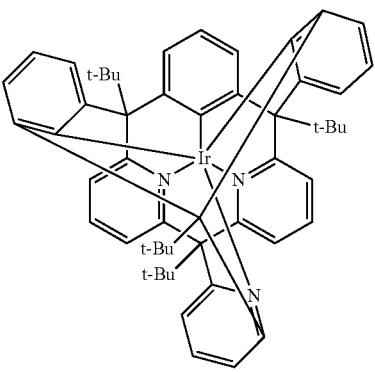 (240)
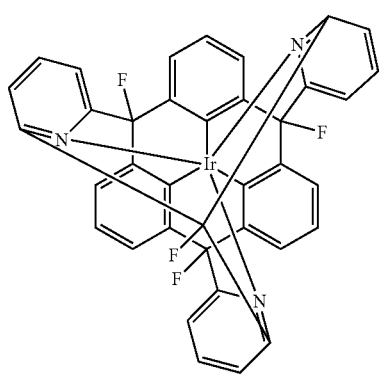 (237)
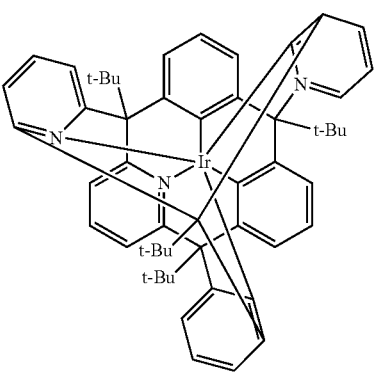 (241)
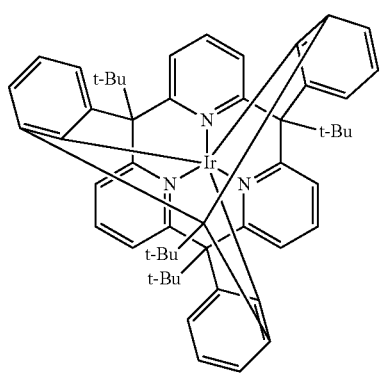 (238)
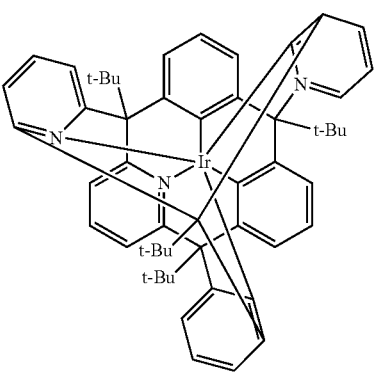 (242)
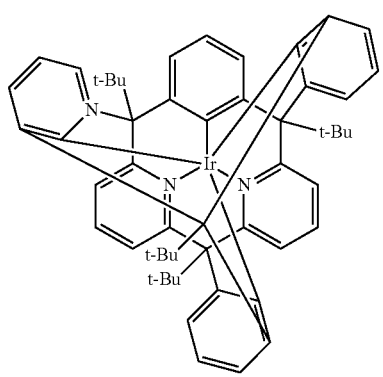 (239)
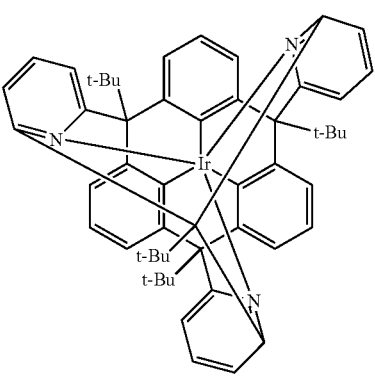 (243)

(244)
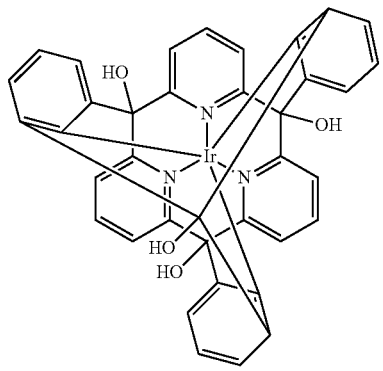
(245)
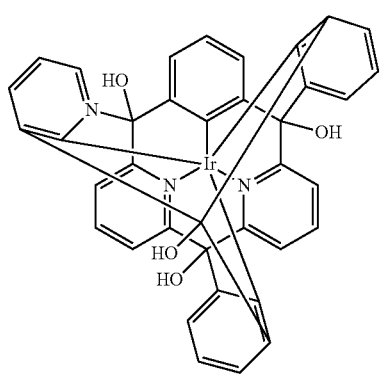
(246)
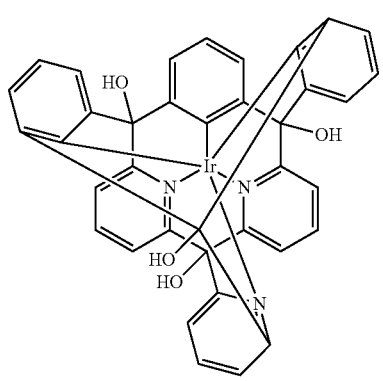
(247)
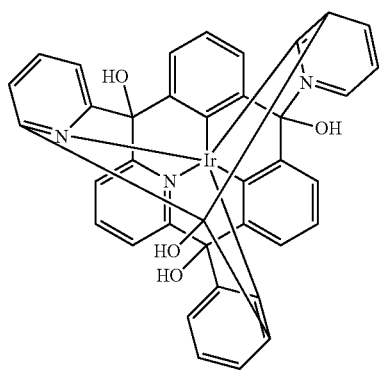
(248)
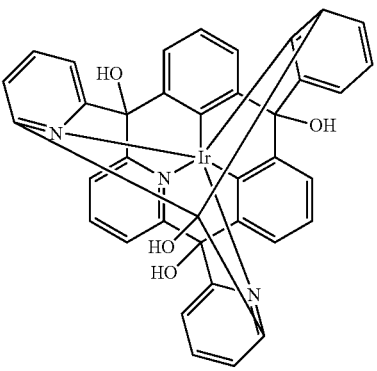
(249)
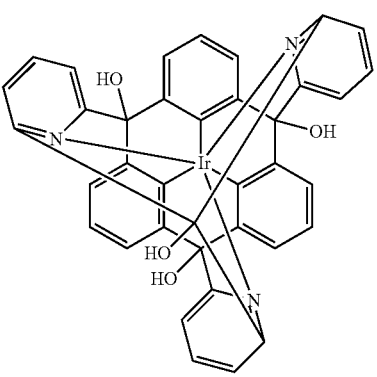
(250)
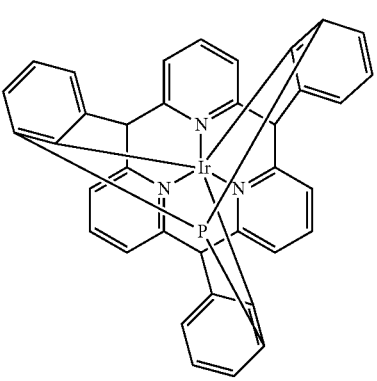
(251)
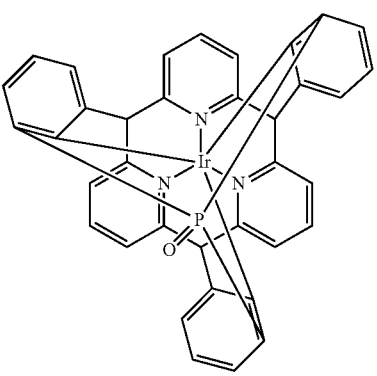

87
-continued
(252)
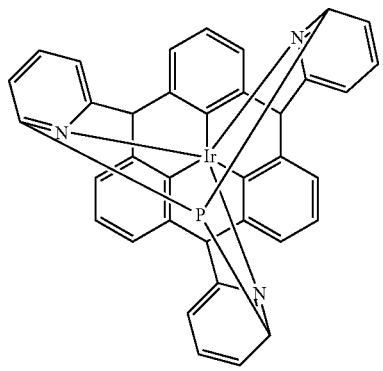
(253)
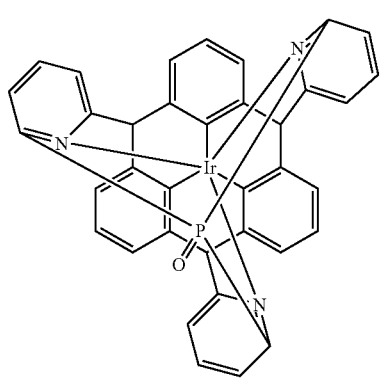
(254)
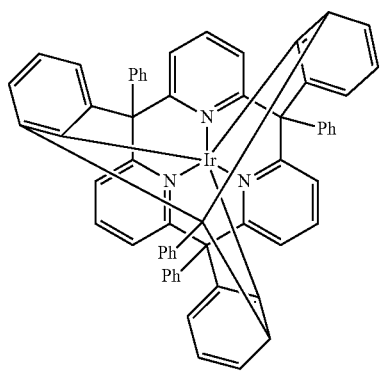
(255)
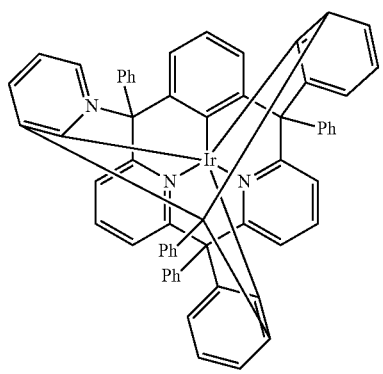
88
-continued
(256)
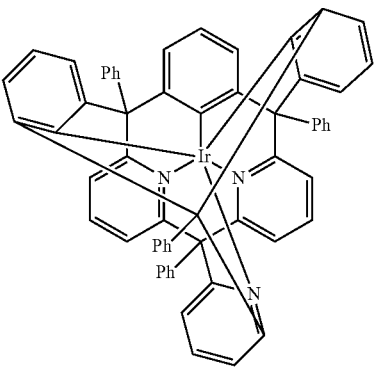
(257)
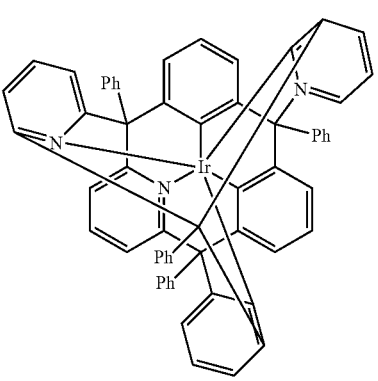
(258)
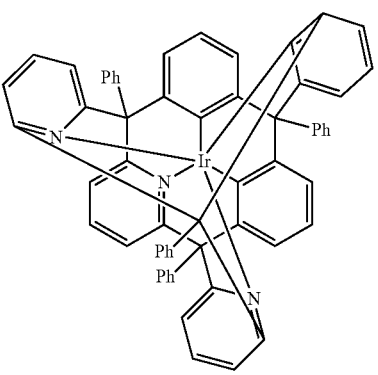
(259)
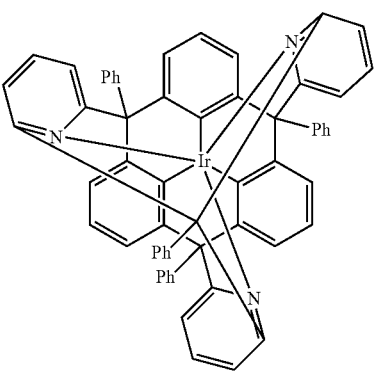

-continued
(260)
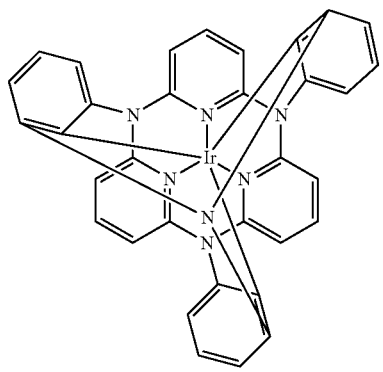
(261)
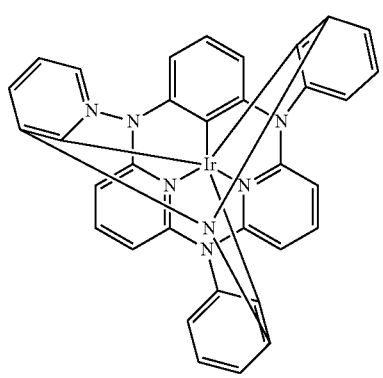
(262)
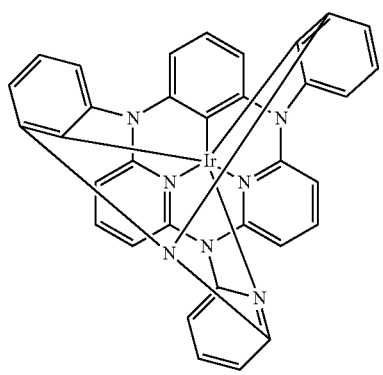
(263)
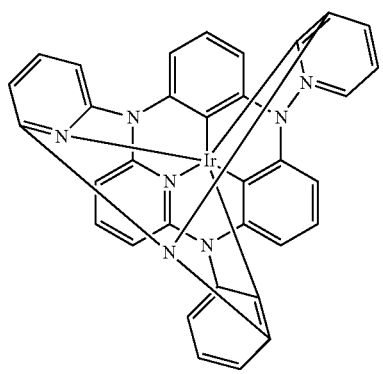
-continued
(264)
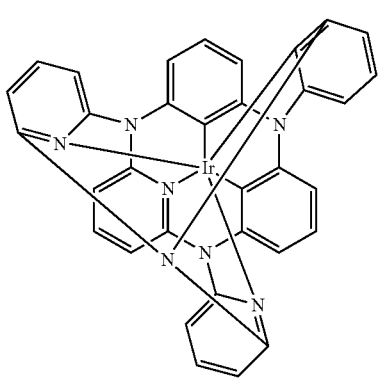
(265)
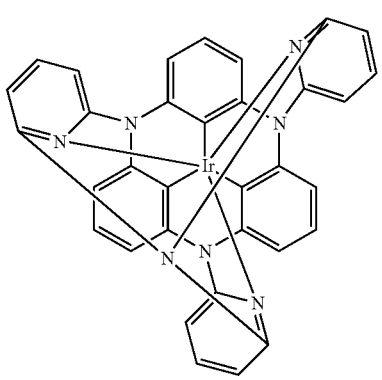
(266)
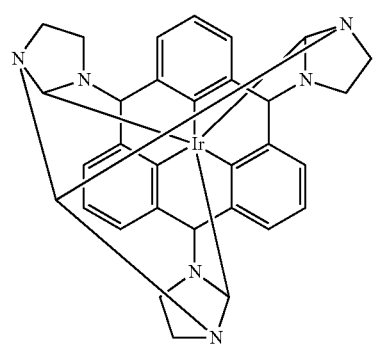
(267)
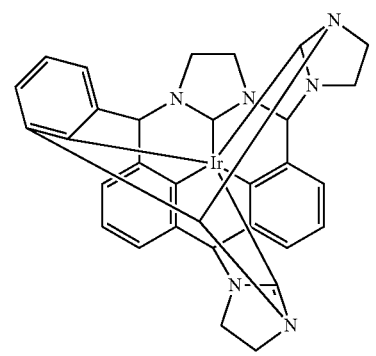

91
-continued
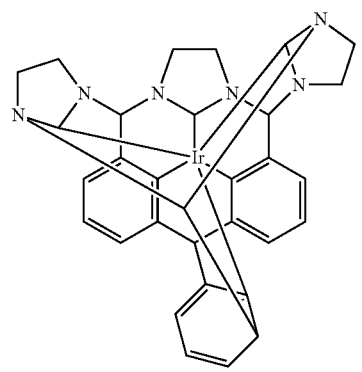
(268)
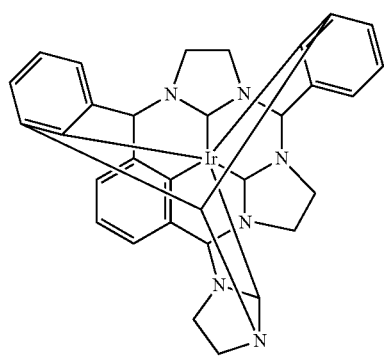
(269)
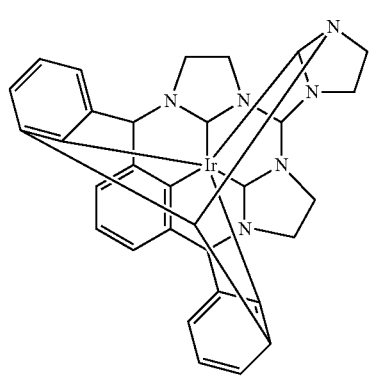
(270)
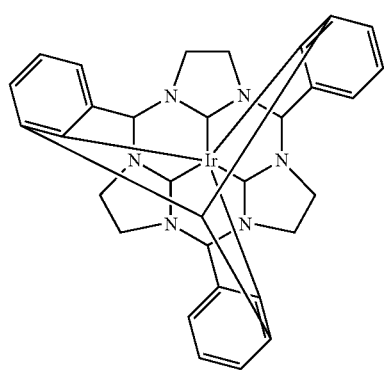
(271)
92
-continued
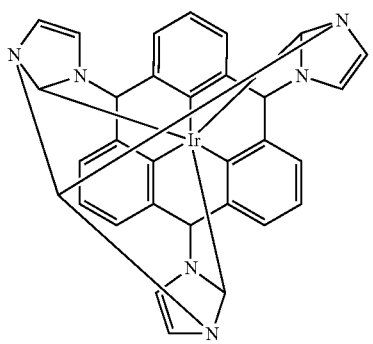
(272)
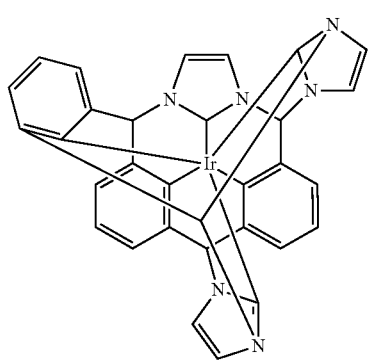
(273)
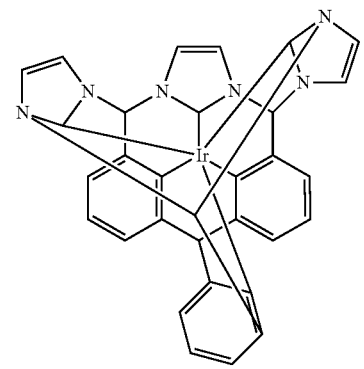
(274)
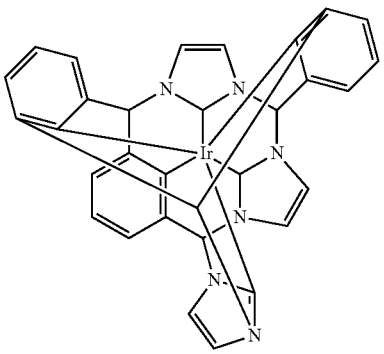
(275)

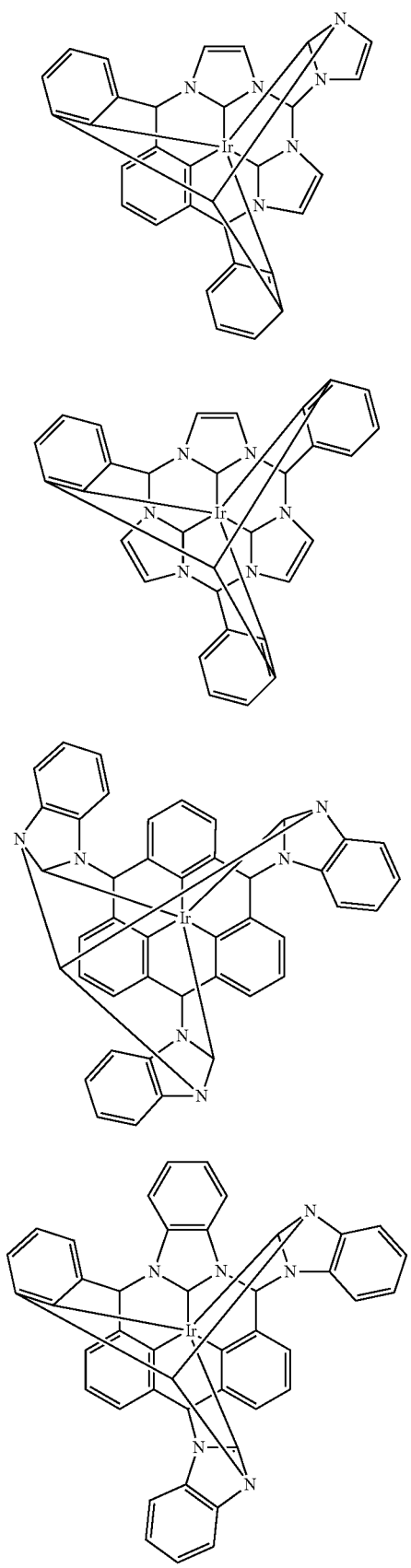
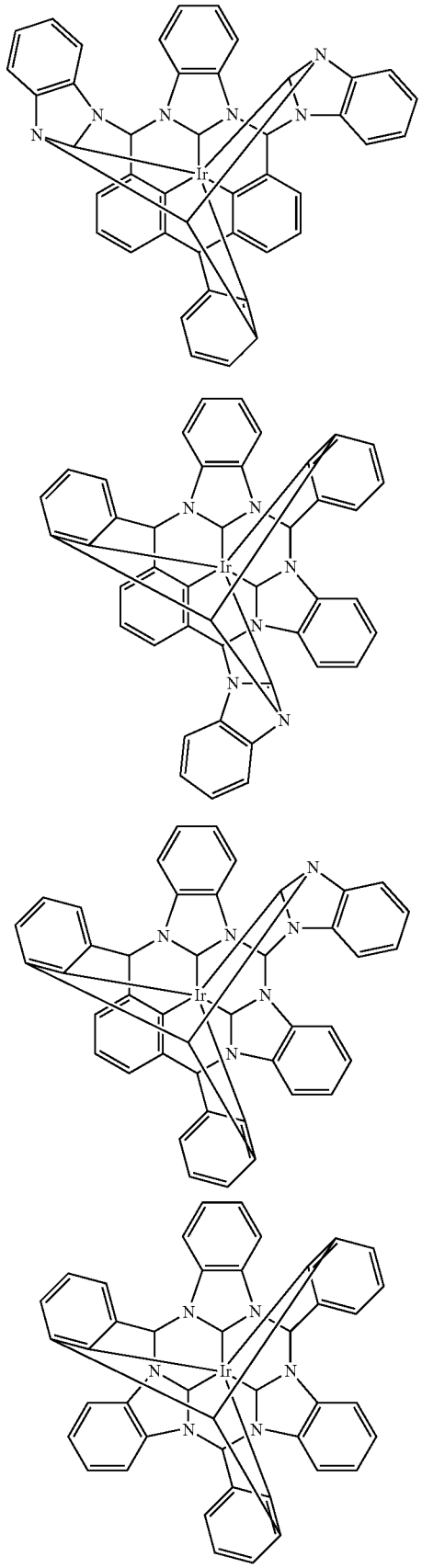

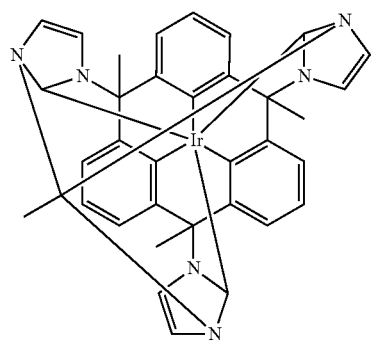
(284)
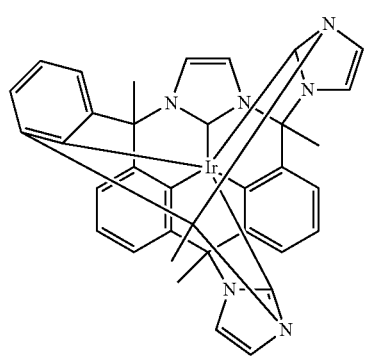
(285)
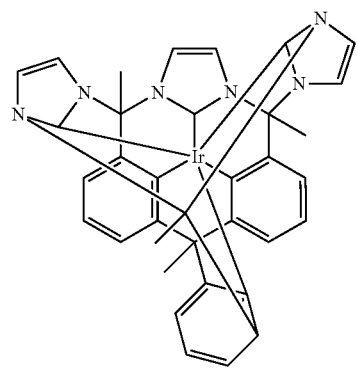
(286)
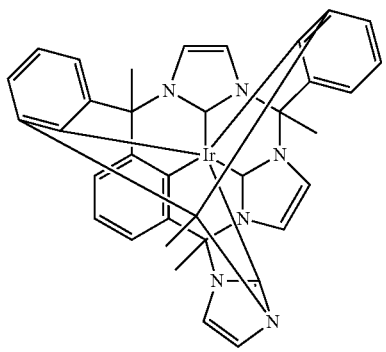
(287)
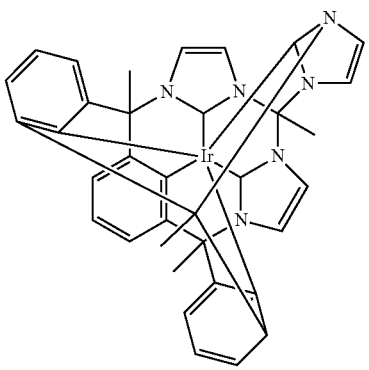
(288)
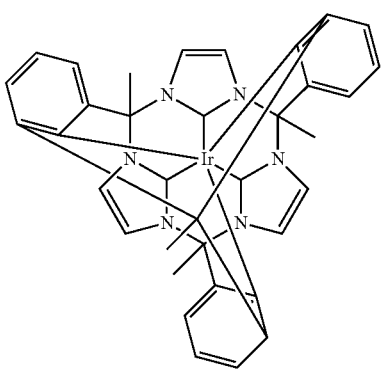
(289)
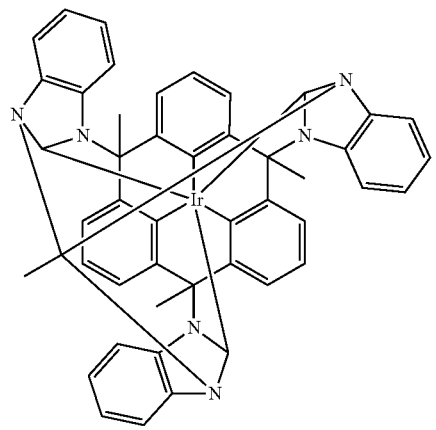
(290)
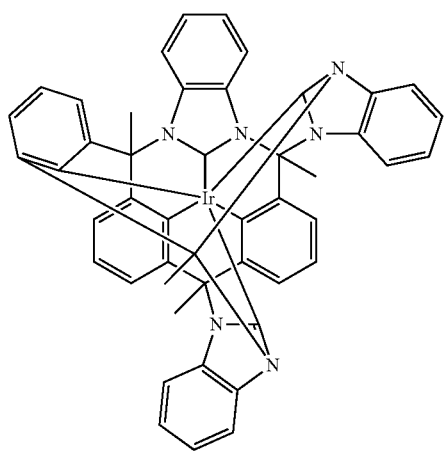
(291)

(292)
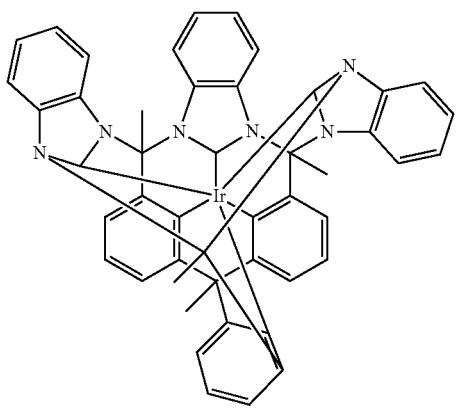
(293)
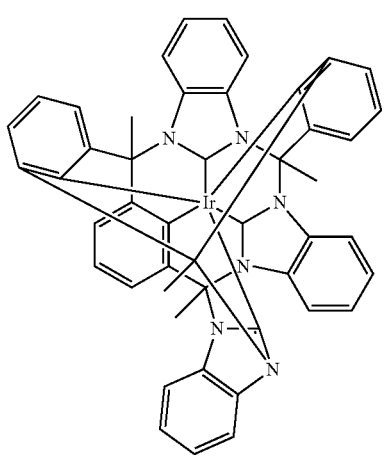
(294)
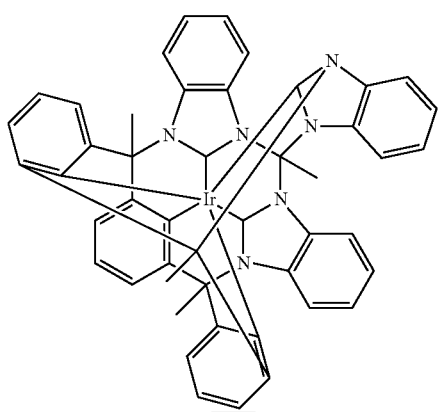
(295)
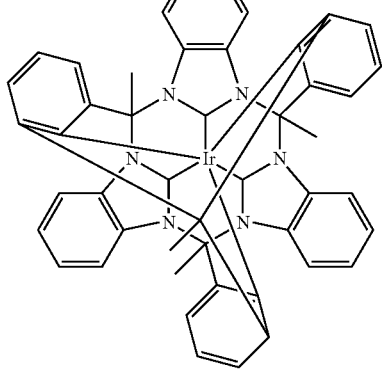
(296)
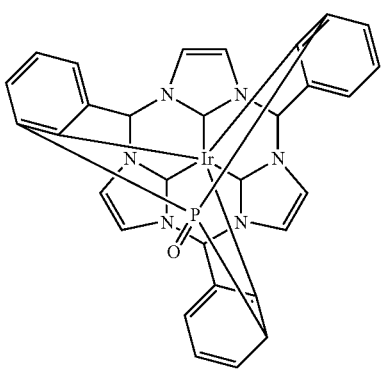
(297)
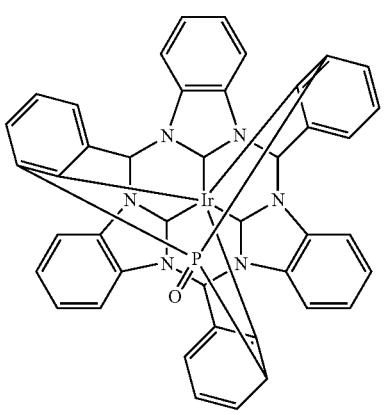
(298)
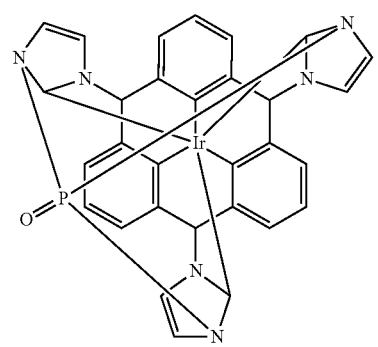
(299)
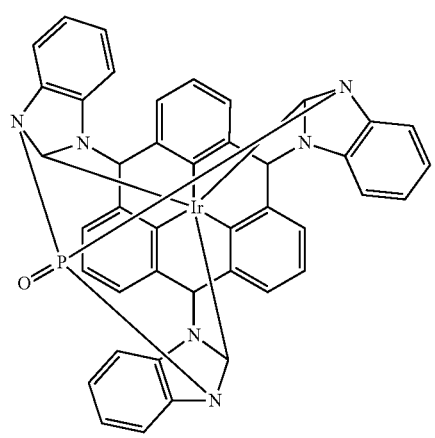

-continued
(300)
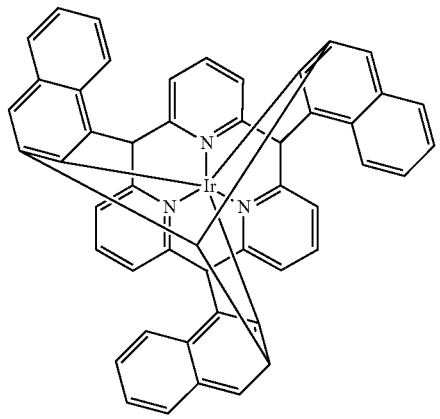
(301)
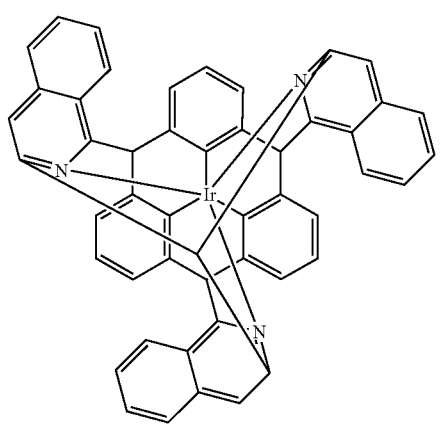
(302)
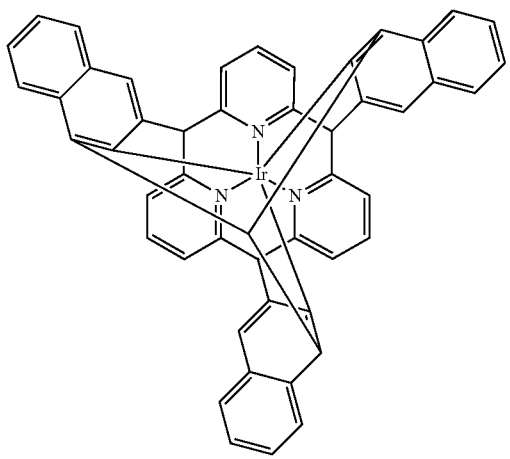
-continued
(303)
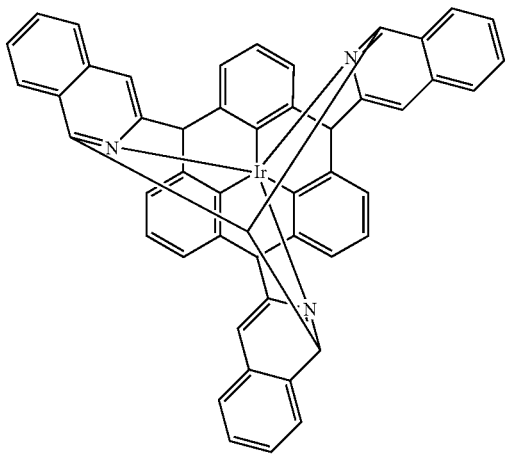
(304)
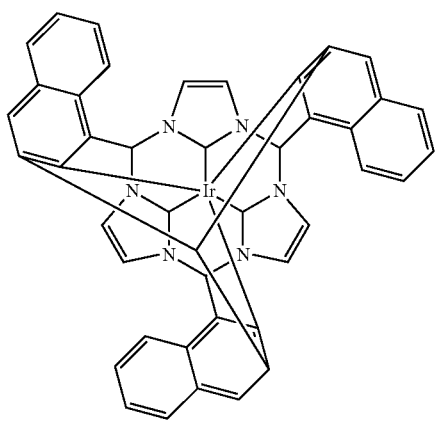
(305)
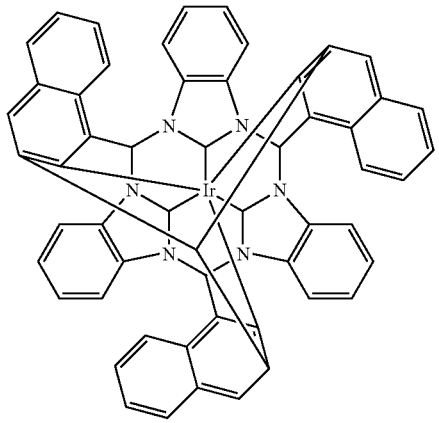

-continued

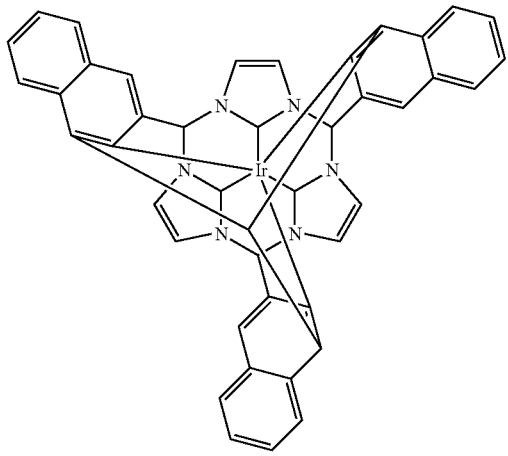

(306)

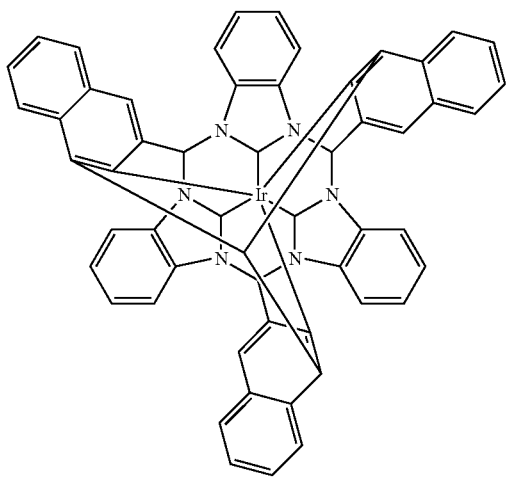

(307)

The above-described complexes of the formula (1) and formulae (3) to (7) and the preferred embodiments indicated above are used as active component in the electronic device. Active components are generally the organic or inorganic materials which are introduced between anode and cathode, for example charge-injection, charge-transport or charge-blocking materials, but in particular emission materials and matrix materials. The compounds according to the invention exhibit particularly good properties for these functions, in particular as emission material in organic electroluminescent devices, as described in greater detail below. A preferred embodiment of the invention are therefore organic electroluminescent devices.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. Interlayers, which have, for example, an exciton-blocking function, may likewise be introduced between two emitting layers. However, it should be pointed out that each of these layers does not necessarily have to be present. The organic electroluminescent device may comprise one emitting layer or it may comprise a plurality of emitting layers, where at least one emitting layer comprises at least one compound of the formula (1) or of the formulae (3) to (7). If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure, see, for example, WO 05/011013).

In a preferred embodiment of the invention, the organic electronic device comprises the compound of the formula (1) or of the formulae (3) to (7) or the preferred embodiments indicated above as emitting compound in an emitting layer. This is the case, in particular, if the metal M is a transition metal, in particular iridium.

If the compound of the formula (1) or of the formulae (3) to (7) is employed as emitting compound in an emitting layer, it is preferably employed in combination with one or more matrix materials. The mixture of the compound of the formula (1) or of the formulae (3) to (7) and the matrix material comprises between 1 and 99% by weight, preferably between 2 and 90% by weight, particularly preferably between 3 and 40% by weight, in particular between 5 and 15% by weight, of the compound of the formula (1) or of the formulae (3) to (7), based on the mixture as a whole comprising emitter and matrix material. Correspondingly, the mixture comprises between 99 and 1% by weight, preferably between 98 and 10% by weight, particularly preferably between 97 and 60% by weight, in particular between 95 and 85% by weight, of the matrix material, based on the mixture as a whole comprising emitter and matrix material.

Suitable matrix materials are ketones, phosphine oxides, sulfoxides and sulfones, for example in accordance with WO 04/013080, WO 04/093207, WO 06/005627 or the unpublished application DE 102008033943.1, triarylamines, carbazole derivatives, for example CBP(N,N-biscarbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056,746, azacarbazoles, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with the unpublished application DE 102008036982.9, WO 07/063,754 or WO 08/056,746, or zinc complexes, for example in accordance with EP 652273 or in accordance with the unpublished application DE 102007053771.0. Furthermore suitable as matrix materials are the compounds of the formula (1) of the present application, as described in greater detail below.

In a further preferred embodiment of the invention, the compound of the formula (1) or of the formulae (3) to (7) or the preferred embodiments indicated above is employed as matrix material for an emitting compound in an emitting layer. This is the case, in particular, if the metal M is a main-group metal, in particular aluminium, gallium or indium.

If the compound of the formula (1) or of the formulae (3) to (7) or the preferred embodiments indicated above is employed as matrix material for an emitting compound in an emitting layer, it is preferably employed in combination with one or more phosphorescent materials (triplet emitters). For the purposes of this invention, phosphorescence is taken to mean the luminescence from an excited state of relatively high spin multiplicity, i.e. a spin state>1, in particular from an excited triplet state or from an MLCT mixed state. For the purposes of the present invention, all luminescent transition-metal complexes from the second and third transition-metal series, in particular all luminescent iridium and platinum complexes, are intended to be regarded as triplet emitters. The mixture of the compound of the formula (1) or of the formulae (3) to (7) or the preferred embodiment indicated above and the emitting compound then comprises between 99 and 1% by weight, preferably between 98 and 10% by weight, particularly preferably between 97 and 60% by weight, in particular between 95 and 85% by weight, of the compound of the formula (1) or of the formulae (3) to (7) or the preferred embodiment indicated above, based on the mixture as a whole comprising emitter and matrix material. Correspondingly, the mixture comprises between 1 and 99% by weight, preferably between 2 and 90% by weight, particularly preferably between 3 and 40% by weight, in particular between 5 and 15% by weight, of the emitter, based on the mixture as a whole comprising emitter and matrix material.

Suitable phosphorescent compounds are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244 or the unpublished application DE 102008015526.8. Furthermore suitable as emitter are the above-indicated compounds of the formula (1) or of the formulae (3) to (7) or the preferred embodiments indicated above. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

In a further preferred embodiment of the invention, the compound of the formula (1) or of the formulae (3) to (7) or the preferred embodiments indicated above is employed as hole-blocking material in a hole-blocking layer and/or as electron-transport material in an electron-transport layer. This is the case, in particular, if the metal M is a main-group metal, in particular an alkali metal, an alkaline-earth metal, aluminium, gallium or indium. The emitting layer here may be fluorescent or phosphorescent.

In a further preferred embodiment of the invention, the compound of the formula (1) or of the formulae (3) to (7) or the preferred embodiments indicated above is employed as hole-transport material in a hole-transport layer and/or as electron-blocking or exciton-blocking material in an exciton-blocking layer.

Preference is furthermore given to an organic electroluminescent device, characterised in that one or more layers are applied by means of a sublimation method, in which the materials are vapour-deposited in vacuum sublimation units at an initial pressure of less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by means of the OVPD (organic vapour phase deposition) method or with the aid of carrier-gas sublimation, in which the materials are applied at a pressure between $10^{-5}$ mbar and 1 bar. A special case of this method is the OVJP (organic vapour jet printing) method, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose, which are obtained, for example, by suitable substitution.

These methods are known in general terms to the person skilled in the art and can be applied by him without problems to organic electroluminescent devices comprising compounds of the formula (1) or of the formulae (3) to (7) or the preferred embodiments indicated above.

The preferred metal complexes of the formulae (4) to (7) and (6a) are novel and are therefore likewise a subject-matter of the present invention. The preferences indicated above for the organic electronic devices also apply entirely analogously to the metal complexes according to the invention.

The present invention still furthermore relates to a process for the preparation of the compounds of the formulae (4) to (7) and (6a) by reaction of the corresponding free ligand of the formula (2) or of the following formulae (69) to (71) with metal compounds of the formula (66), (67) or (68) indicated above.

The present invention furthermore relates to the compounds of the following formulae (69) to (71). These compounds are the free ligands of the metal complexes of the formulae (4) to (6) according to the invention and are thus a valuable intermediate for the synthesis of the metal complexes according to the invention:

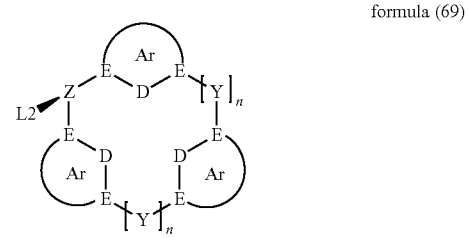

formula (69)

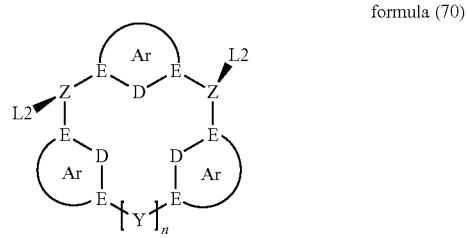

formula (70)

formula (71)

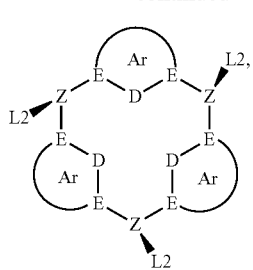

where the following compound is excluded from the invention:

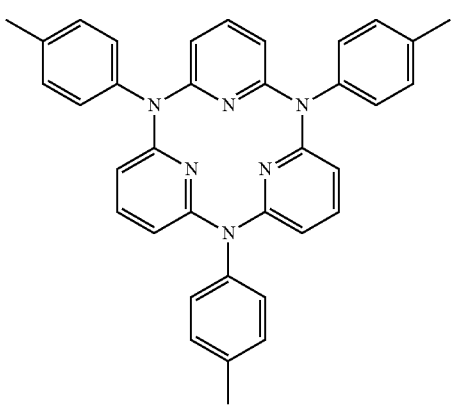

The symbols and indices here have the meanings mentioned above, where the groups D and L2, if they are bonded to the metal M as anionic groups in the complex, additionally each carry a hydrogen atom. Furthermore, the same preferences as described above for the metal complexes apply entirely analogously to the free ligands.

The compounds according to the invention described above, in particular compounds which are substituted by reactive leaving groups, such as bromine, iodine, boronic acid or boronic acid ester, can be used as monomers for the generation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (1) or of the formulae (3) to (7), where one or more bonds are present from the complex of the formula (1) or of the formulae (3) to (7) to the polymer, oligomer or dendrimer. Depending on the linking of the compound of the formula (1) or of the formulae (3) to (7), the complex therefore forms a side chain of the oligomer or polymer or is linked in the main chain. The polymers, oligomers or dendrimers may be conjugated, partially conjugated or non-conjugated. The oligomers or polymers may be linear, branched or dendritic.

The same preferences as described above apply entirely analogously to the recurring units of the formula (1) or of the formulae (3) to (7) in oligomers, dendrimers and polymers.

For the preparation of the oligomers or polymers, the monomers according to the invention are homopolymerised or copolymerised with further monomers. Preference is given to copolymers, where the units of the formula (1) or formulae (3) to (7) are preferably present in an amount of 0.01 to 50 mol %, particularly preferably in the range from 0.1 to 20 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The proportion of these units in total is preferably in the region of at least 50 mol %. The polymers, oligomers and dendrimers may also comprise further units, for example hole-transport units, in particular those based on triarylamines, and/or electron-transport units.

Furthermore, the metal complexes according to the invention may also be further functionalised and thus converted into extended metal complexes. An example which may be mentioned here is the functionalisation with arylboronic acids by the SUZUKI method or with primary or secondary amines by the HARTWIG-BUCHWALD method.

The organic electronic devices according to the invention, in particular organic electroluminescent devices, are distinguished by the following surprising advantages over the prior art:

1. In contrast to many metal complexes in accordance with the prior art, which undergo partial or complete pyrolytic decomposition on sublimation, the compounds according to the invention have high thermal stability.
2. Organic electroluminescent devices comprising compounds of the formula (1) as emitting materials have an excellent lifetime.
3. Blue-phosphorescent complexes which have a deep-blue emission colour and a long lifetime on use in organic electroluminescent devices are accessible. This is a significant advance over the prior art since to date blue-phosphorescent devices were only accessible with poor colour coordinates and in particular a poor lifetime.
4. The compounds according to the invention, employed in organic electroluminescent devices, result in high efficiencies and in steep current/voltage curves.

These above-mentioned advantages are not accompanied by an impairment of the other electronic properties.

The invention is explained in greater detail by the following examples without wishing it to be restricted thereby. The person skilled in the art will be able to prepare further complexes according to the invention without inventive step from the descriptions and use these in organic electronic devices or use the process according to the invention.

EXAMPLES

The following syntheses are, unless indicated otherwise, carried out under a protective-gas atmosphere in dried solvents. The solvents and reagents can be purchased From ALDRICH or ABCR. The syntheses of ligands 1 to 4 below is carried out in accordance with the literature indicated:

Ligand 1:

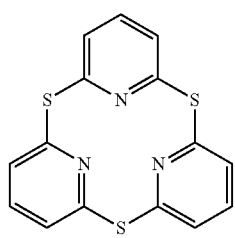

M. Tatazona et al., *Macromolecules* 1992, 25, 5020.

Ligand 2:

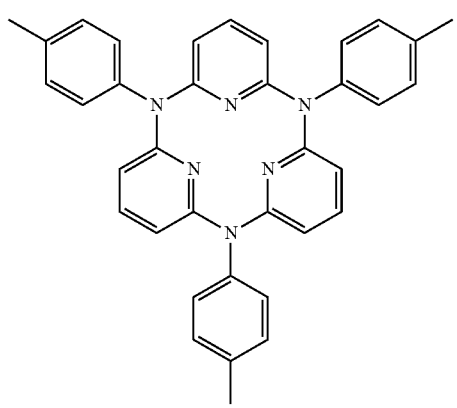

Y. Suzuki et al., *Synlett* 2005, 2, 263.

Ligand 3:

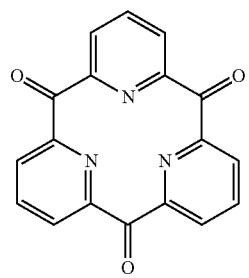

G. R. Newkome et al., *Heterocycles* 1978, 9 (11), 1555.

Ligand 4:

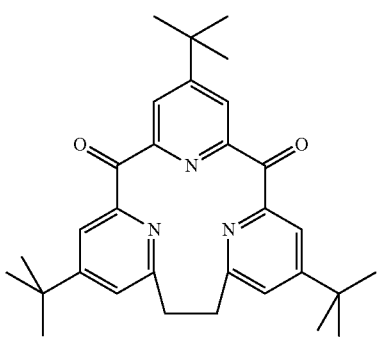

A. N. Vedernikov et al., *J. Org. Chem.* 2003, 68, 4806.

Further Ligand Syntheses

Example 1

Synthesis of Ligand 5

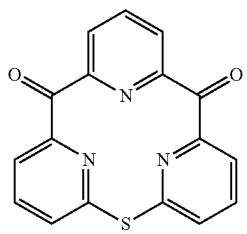 [SMILES: O=C1c2cccc(n2)Sc2cccc(n2)C(=O)c2cccc1n2]

A solution of 26.8 g (50 mmol) of 2,6-bis[2-(6-bromo-2-pyridinyl)-1,3-dioxolan-2-yl]pyridine (synthesised in accordance with G. R. Newkome et al., *J. Am. Chem. Soc.* 1986, 108(19), 6074) and 2.0 g (50 mmol) of anhydrous sodium hydrogensulfide in 300 ml of 1,2-propanediol is stirred at 120° C. for 16 h. After cooling, the mixture is poured into 500 ml of water and stirred for a further 12 h. The solid is filtered off with suction, taken up in a mixture of 50 ml of ethanol and 50 ml of conc. hydrochloric acid and boiled under reflux for 48 h. The ethanol is then removed in vacuo, the mixture is rendered alkaline using solid potassium hydroxide, extracted three times with 50 ml of dichloromethane, and the combined extracts are washed with 100 ml of water, dried over magnesium sulfate and evaporated to dryness. The oily residue is chromatographed on silica gel (eluent acetone/triethylamine 98:2) and then recrystallised from acetone. Yield: 2.2 g (7 mmol), 13.9%. Purity 97% according to $^1$H-NMR.

Example 2

Synthesis of Ligand 6

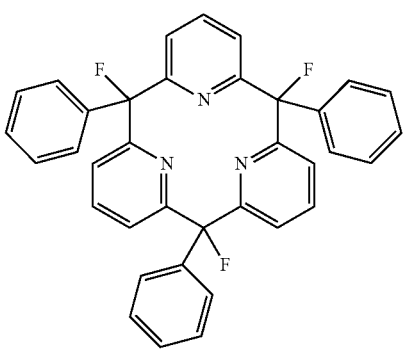 [SMILES: FC1(c2ccccc2)c2cccc(n2)C(F)(c2ccccc2)c2cccc(n2)C(F)(c2ccccc2)c2cccc1n2]

20 ml (20 mmol) of a solution of potassium triethylborohydride (1 N in THF) are added at −78° C. with vigorous stirring to a suspension of 8.3 g (20 mmol) of the complex ligand 3-CuCl (preparation: see Example 5) in 200 ml of THF, and the mixture is stirred for a further 10 min. 40 ml (80 mmol) of a solution of phenyllithium (2 N in di-n-butyl ether) are subsequently added dropwise, and the mixture is stirred at −78° C. for a further 1 h and then allowed to warm slowly to room temperature. 50 ml of a 2 N aqueous sodium cyanide solution are added, the mixture is stirred at room temperature for 12 h, the aqueous phase is separated off, and the organic phase is evaporated to dryness. The residue is dissolved in 200 ml of chloroform, insoluble fractions are filtered off, a solution of 32.0 g (240 mmol) of dimethylaminosulfur trifluoride in 200 ml of chloroform is added dropwise, and the mixture is heated under reflux for 30 min. After cooling, the mixture is hydrolysed dropwise using 50 ml of ice-water, then rendered alkaline using 250 ml of 4 N sodium hydroxide solution. The organic phase is separated off and dried over calcium chloride. After the organic phase has been concentrated to about 10 ml in vacuo, 50 ml of methanol are added. After standing for 12 h, the crystals are filtered off with suction and recrystallised again from chloroform/methanol. Yield: 5.2 g (9 mmol), 46.8%. Purity 97% according to $^1$H-NMR.

Synthesis of the Metal Complexes

Example 3

Synthesis of the Complex Ligand 1-CuI

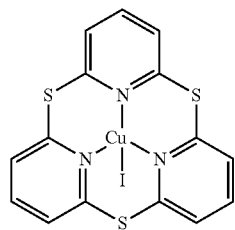

A suspension of 3.3 g (10 mmol) of ligand 1, 1.9 g (10 mmol) of copper(I) iodide and 50 g of glass beads (4 mm diameter) in 200 ml of dichloromethane is stirred at room temperature for 24 h. The glass beads are filtered off via a coarse sieve, the dichloromethane is concentrated to about 20 ml in vacuo, 50 ml of ethanol are added dropwise, the mixture is stirred for a further 2 h, and the orange crystals are filtered off, washed twice with 20 ml of ethanol each time and recrystallised from DMSO. Yield: 4.7 g (9.1 mmol), 90.1%. Purity>99% according to $^1$H-NMR.

Example 4

Synthesis of the Complex Ligand 2-CuI

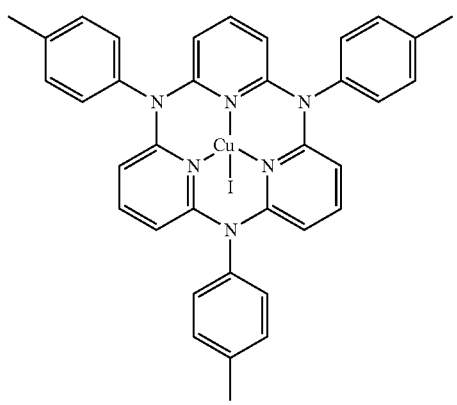

Preparation analogous to Example 3, using 5.5 g (10 mmol) of ligand 2. Yield: 5.5 g (7.5 mmol), 74.6%. Purity>99% according to $^1$H-NMR.

Example 5

Synthesis of the Complex Ligand 3-CuCl

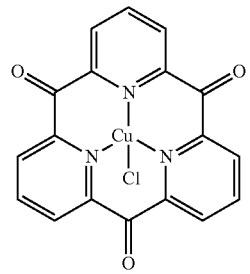

Preparation analogous to Example 3, using 3.2 g (10 mmol) of ligand 3. Yield: 3.9 g (9.3 mmol), 93.3%. Purity>98% according to $^1$H-NMR.

Example 6

Synthesis of the Complex Ligand 4-Mo(CO)$_3$

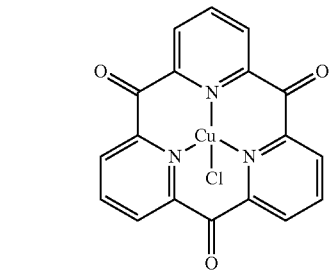

A solution of 2.3 g (5 mmol) of ligand 4 and 1.4 g (5 mmol) of cycloheptatrienemolybdenum tricarbonyl in 50 ml of toluene is heated under reflux for 6 h and subsequently concentrated to about 10 ml in vacuo, and 50 ml of hexane are added with stirring. After 12 h, the crystals are filtered off with suction and washed twice with 10 ml of hexane each time. Yield: 2.6 g (4.1 mmol), 81.8%. Purity>99% according to $^1$H-NMR.

Example 7

Synthesis of the Complex Ligand 5-W(CO)$_3$

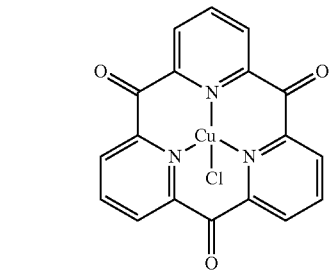

A solution of 1.6 g (5 mmol) of ligand 5, 1.8 g (5 mmol) of tungsten hexa carbonyl and 10 mg of palladium(II) oxide in 50 ml of toluene is heated under reflux for 48 h. After cooling, the solution is filtered through Celite, and the filtrate is evaporated. The residue is recrystallised from dichloromethane/hexane. Yield: 1.6 g (2.7 mmol), 54.0%. Purity>99% according to $^1$H-NMR.

Example 8

Synthesis of the Complex Ligand 6-Ir

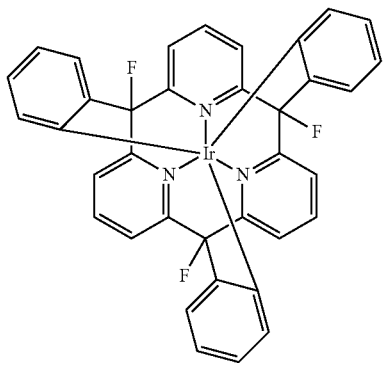

A mixture of 2.8 g (5 mmol) of ligand 6, 1.5 g (5 mmol) of iridium(III) chloride hydrate and 10 ml of ethylene glycol is stirred at 190° C. for 48 h. After cooling, 100 ml of water are added, and the brown precipitate is filtered off, dried and then chromatographed on neutral aluminium oxide with dichloromethane/THF (1:1). Yield: 820 mg (1.1 mmol), 22.0%. Purity>99% according to $^1$H-NMR.

Example 9

Ligand 7-Ir a) Synthesis of the Ligand Precursor:

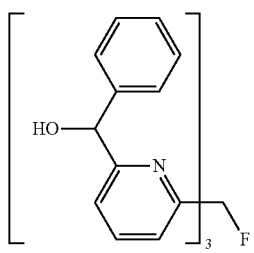

120 ml of n-butyllithium (2.5 M in hexane) are added dropwise over the course of 10 min. to a solution of 53.6 g (100 mmol) of tris(6-bromopyrid-2-yl)fluoromethane [760177-68-2] in 1500 ml of THF at −78° C. with vigorous stirring, the mixture is stirred at −78° C. for a further 30 min., and 32.0 ml (315 mmol) of benzaldehyde are then added dropwise. After warming to room temperature, the THF is removed in vacuo, the residue is taken up in 500 ml of dichloromethane and washed twice with 200 ml of water, and the organic phase is dried over magnesium sulfate and then evaporated to dryness in vacuo. Yield: 54.3 g (93 mmol), 93.0%, about 90% according to $^1$H-NMR (diastereomer mixture). The viscous oil obtained in this way is employed without further purification.

b) Synthesis of Ligand 7-Ir:

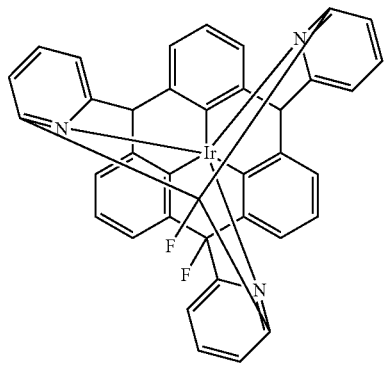

A mixture of 5.8 g (10 mmol) of the ligand precursor from Example 9a) and 2.4 g (5 mmol) of sodium bisacetylacetonatodichloroiridium in 100 ml of ethylene glycol is stirred at 80° C. for 16 h and then at 140° C. for 24 h under a continuous stream of argon. After cooling, 200 ml of water are added to the suspension, the brown solid is filtered off with suction, washed with water and subsequently dried at 70° C. in a stream of nitrogen. The solid obtained in this way is suspended in 50 ml of glacial acetic acid, 0.5 ml of sulfuric acid is added to the suspension, and the mixture is subsequentially heated under reflux for 2 h. After cooling, the glacial acetic acid is removed in vacuo, the residue is taken up in 500 ml of dichloromethane, and the organic phase is washed once with 200 ml of saturated sodium hydrogencarbonate solution, once with 200 ml of water and then dried over magnesium sulfate. After removal of the dichloromethane, the residue is chromatographed on silica gel with THF. The yellow solid obtained in this way is then sublimed twice in a high vacuum (p=$10^{-5}$ mbar, T=340° C.). Yield: 270 mg (0.37 mmol). 7.5%, 99.8% according to HPLC.

Example 10

Production and Characterisation of Organic Electroluminescent Devices

LEDs are produced by the general process outlined below. This must of course be adapted in individual cases to the particular circumstances (for example layer-thickness variation in order to achieve optimum efficiency or colour).

General Process for the Production of OLEDs:

After the ITO-coated substrates (for example glass support, PET film) have been cut to the correct size, they are cleaned in an ultrasound bath in a number of cleaning steps (for example soap solution, Millipore water, isopropanol). For drying, they are blown with an N$_2$ gun and stored in a desiccator. Before vapour-coating with the organic layers, they are treated with an ozone plasma device for about 20 minutes. It may be advisable to use a polymeric hole-injection layer as the first organic layer. This is generally a conjugated, conductive polymer, such as, for example, a polyaniline derivative (PANI) or a polythiophene derivative (for example PEDOT, BAYTRON P™ from BAYER). This is then applied by spin coating. The organic layers are applied successively by vapour deposition in a high-vacuum unit. The layer thickness of the respective layer and the vapour-deposition rate are monitored and adjusted via a quartz resonator. It is also possible for individual layers to consist of more than one compound, i.e. in general a host material may be doped with a guest material. This is achieved by co-evaporation from two or more sources. An electrode is also applied to the organic layers. This is generally carried out by thermal evaporation (Balzer BA360 or Pfeiffer PL S 500). The transparent ITO electrode is subsequently contacted as anode and the metal electrode as cathode, and the device parameters are determined.

OLEDs having the following structure 1 are produced analogously to the general process mentioned above:

PEDOT 20 nm (spin-coated from water; PEDOT purchased from BAYER AG; poly[3,4-ethylenedioxy-2,5-thiophene]

HIM1 20 nm of 2,2',7,7'-tetrakis(di-p-tolylamino)spiro-9,9'-bifluorene (vapour-deposited)

NPB 20 nm of 4,4'-bis(1-naphthylphenylamino)biphenyl (vapour-deposited)

mCP 20 nm of 1,3-bis(N-carbazolyl)benzene (vapour-deposited)

doped with 10% of triplet emitter examples according to the invention, see table BCP 5 nm of 2,9-dimethyl-4,7-diphenyl-1,10-phenanthroline (vapour-deposited)

AlQ$_3$ 30 nm (vapour-deposited)

Li/Al 5 nm of LiF, 150 nm of Al on top as cathode.

This as yet unoptimised OLED is characterised by standard methods. The table shows the efficiency and voltage at 500 cd/m$^2$ and the colour.

| Ex. | Emitter | Efficiency [cd/A] at 500 cd/m$^2$ | Voltage [V] at 500 cd/m$^2$ | Colour CIE x/y |
|---|---|---|---|---|
| 11 | Example 6 (ligand 4-Mo(CO)$_3$) | 17.8 | 6.5 | 0.28/0.61 |
| 12 | Example 9 (ligand 7-Ir) | 34.6 | 4.8 | 0.32/0.64 |

Furthermore, OLEDs having the following structure 2 are produced analogously to the general process mentioned above:

PEDOT 20 nm (spin-coated from water; PEDOT purchased from BAYER AG; poly[3,4-ethylenedioxy-2,5-thiophene]

PVK 60 nm (spin-coated from chlorobenzene, PVK Mw=1,100,000 purchased from Aldrich, solution comprising 5% by weight of emitter according to Example 4)

Ba/Ag 10 nm of Ba/150 nm of Ag as cathode.

This as yet unoptimised OLED is characterised by standard methods. The table shows the efficiency and voltage at 500 cd/m$^2$ and the colour.

| Ex. | Emitter | Efficiency [cd/A] at 500 cd/m$^2$ | Voltage [V] at 500 cd/m$^2$ | Colour CIE x/y |
|---|---|---|---|---|
| 10 | Example 4 (ligand 2-CuI) | 5.4 | 7.2 | 0.70/0.30 |

The invention claimed is:

1. An electronic device comprising at least one metal complex of formula (4), (5), (6), (6a) or (7):

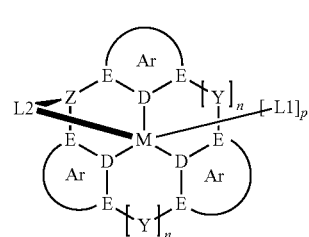

formula (4)

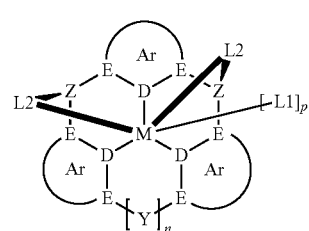

formula (5)

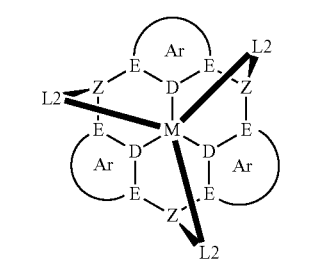

formula (6)

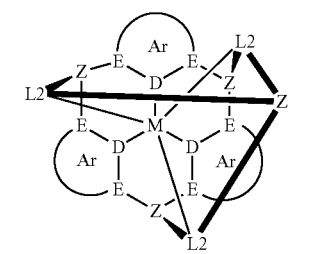

formula (6a)

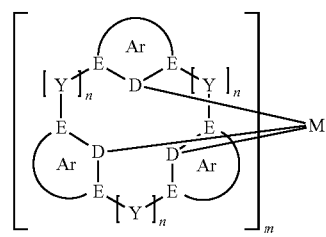

formula (7)

wherein Y is, identically or differently on each occurrence, an optionally substituted atom selected from C, N or P wherein the substituent, which is optionally present might also be coordinated to the metal M;

L1 is, identically or differently on each occurrence, a mono-, bi-, tri-, tetra-, penta-, or hexadentate ligand;

n is, identically or differently on each occurrence, 0, 1 or 2, where n=0 means that the group Y is not present and a single bond is present between two E;

p is 0, 1, 2, or 3,

M is a transition metal or a main-group metal from the third main group;

D is, identically or differently on each occurrence, C or N;
E is, identically or differently on each occurrence, C or N;
Ar is, identically or differently on each occurrence, a group which forms an aryl or heteroaryl group having 5 to 14 aromatic ring atoms together with the group E—D—E and is optionally substituted by one or more radicals R;
R is, identically or differently on each occurrence, H, deuterium, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 40 C atoms optionally substituted by one or more radicals $R^2$, a straight-chain alkenyl or alkynyl group having 2 to 40 C atoms optionally substituted by one or more radicals $R^2$, a branched or cyclic alkyl, alkenyl, alkynyl, alkoxy; or thioalkoxy group having 3 to 40 C atoms optionally substituted by one or more radicals $R^2$, wherein one or more non-adjacent $CH_2$ groups of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$, and wherein one or more H atoms of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by F, Cl, Br, I, CN, or $NO_2$, an aromatic or heteroaromatic ring system having 5 to 60 aromatic ring atoms optionally substituted by one or more radicals $R^2$, an aryloxy or heteroaryloxy group having 5 to 60 aromatic ring atoms optionally substituted by one or more radicals $R^2$, a diarylamino group, diheteroarylamino group or arylheteroarylamino group having 10 to 40 aromatic ring atoms optionally substituted by one or more radicals $R^2$, or a combination of these systems; and wherein two or more R optionally define a mono- or polycyclic, aliphatic, aromatic, and/or benzo-fused ring system with one another;
$R^2$ is, identically or differently on each occurrence, H, F, or an aliphatic, aromatic, and/or heteroaromatic radical having 1 to 20 C atoms, wherein one or more H atoms is optionally replaced by F; and wherein two or more $R^2$ optionally define a mono- or polycyclic, aliphatic, or aromatic ring system with one another;
Z is, identically or differently on each occurrence, $C^-$, $CR^1$, N, or P;
$R^1$ is, identically or differently on each occurrence, R or a group L2;
L2 is, identically or differently on each occurrence, a donor group having 1 to 40 C atoms, which optionally forms a further bond or coordination to M and is optionally substituted by one or more radicals R; and
m is 2, 3, or 4.

2. The electronic device of claim 1, wherein said electronic device comprises an anode, cathode, and at least one layer which comprises said at least one metal complex of formula (4), (5), (6), (6a) or (7), and wherein said electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

3. The electronic device of claim 2, wherein said electronic device is an organic electroluminescent device.

4. The electronic device of claim 1, wherein M is zirconium, hafnium, molybdenum, tungsten, rhenium, ruthenium, osmium, rhodium, iridium, palladium, platinum, copper, silver, gold, scandium, yttrium, lanthanum, aluminum, gallium, or indium.

5. The electronic device of claim 1, wherein the aryl or heteroaryl group formed by Ar together with the group E-D-E is a group of formulae (8), (9), and (11)-(19), wherein the dashed bonds in each formula indicate the bonds of each group to Y, and wherein * in each case is the position of coordination to M:

formula (8)

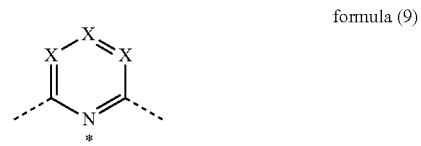

formula (9)

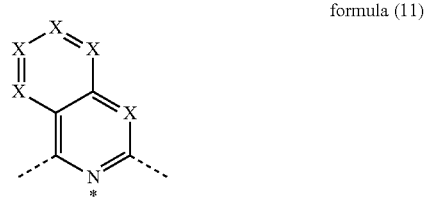

formula (11)

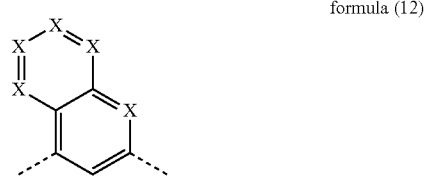

formula (12)

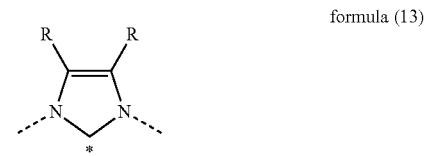

formula (13)

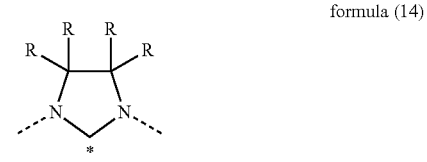

formula (14)

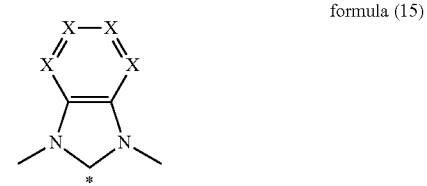

formula (15)

-continued

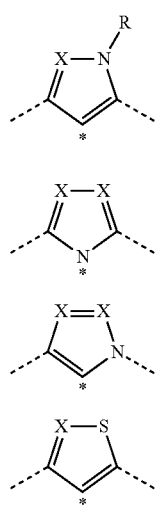

formula (16)

formula (17)

formula (18)

formula (19)

wherein X is, identically or differently on each occurrence, CR or N, with the proviso that a maximum of three X in each group is N;

R is, identically or differently on each occurrence, H, deuterium, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 40 C atoms optionally substituted by one or more radicals $R^2$, a straight-chain alkenyl or alkynyl group having 2 to 40 C atoms optionally substituted by one or more radicals $R^2$, a branched or cyclic alkyl, alkenyl, alkynyl, alkoxy, or thioalkoxy group having 3 to 40 C atoms optionally substituted by one or more radicals $R^2$, wherein one or more non-adjacent $CH_2$ groups of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$, and wherein one or more H atoms of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by F, Cl, Br, I, CN, or $NO_2$, an aromatic or heteroaromatic ring system having 5 to 60 aromatic ring atoms optionally substituted by one or more radicals $R^2$, an aryloxy or heteroaryloxy group having 5 to 60 aromatic ring atoms optionally substituted by one or more radicals $R^2$, a diarylamino group, diheteroarylamino group or arylheteroarylamino group having 10 to 40 aromatic ring atoms optionally substituted by one or more radicals $R^2$, or a combination of these systems; and wherein two or more R optionally define a mono- or polycyclic, aliphatic, aromatic, and/or benzo-fused ring system with one another;

$R^2$ is, identically or differently on each occurrence, H, F, or an aliphatic, aromatic, and/or heteroaromatic radical having 1 to 20 C atoms, wherein one or more H atoms is optionally replaced by F; and wherein two or more $R^2$ optionally define a mono- or polycyclic, aliphatic, or aromatic ring system with one another.

6. The electronic device of claim 1, wherein L1 is selected from carbon monoxide, isonitriles, amines, imines, diimines, phosphines, phosphites, arsines, stibines-, nitrogen-containing heterocyclic compounds, hydride, deuteride, the halides F, Cl, Br, and I, alkylacetylides, arylacetylides, cyanide, cyanate, isocyanate, thiocyanate, isothiocyanate, aliphatic or aromatic alcoholates, aliphatic or aromatic thioalcoholates, amides, carboxylates, anionic, nitrogen-containing heterocyclic compounds, $O^{2-}$, $S^{2-}$, nitrenes, $N^{3-}$, diamines, heterocyclic compounds containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, borates of nitrogen-containing heterocyclic compounds, bidentate monoanionic ligands which, with the metal, form a cyclometallated five-membered ring containing at least one metal-carbon bond, $\eta^5$-cyclopentadienyl, $\eta^5$-pentamethylcyclopentadienyl, $\eta^6$-benzene, $\eta^7$-cycloheptatrienyl, each of which are optionally substituted by R, 1,3,5-cis-cyclohexane derivatives, 1,1,1-tri(methylene)methane derivatives, and 1,1,1-trisubstituted methanes.

7. The electronic device of claim 1, wherein said electronic device is an organic electroluminescent device comprising a cathode, an anode, and at least one emitting layer and optionally further layers in each case selected from the group consisting of one or more hole-injection layers, hole-transport layers, hole-blocking layers, electron-transport layers, electron-injection layers, exciton-blocking layers, charge-generation layers, organic p/n junctions, and inorganic p/n junctions.

8. The electronic device of claim 7, wherein the compound of formula (4), (5), (6), (6a) or (7) is employed as emitting compound in an emitting layer, or in that the compound of formula (4), (5), (6), (6a) or (7) is employed as matrix material for an emitting compound in an emitting layer, or in that the compound of formula (4), (5), (6), (6a) or (7) is employed as hole-blocking material in a hole-blocking layer and/or as electron-transport material in an electron-transport layer, or in that the compound of formula (4), (5), (6), (6a) or (7) is employed as hole-transport material in a hole-transport layer and/or as exciton-blocking material in an exciton-blocking layer.

9. The electronic device of claim 1, wherein said electronic device comprises a compound of formula (4), (5), (6), or (7):

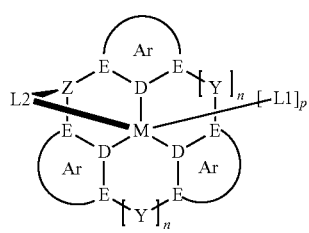

formula (4)

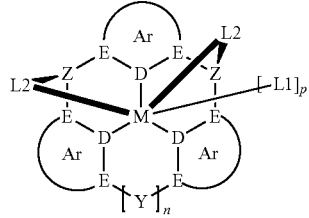

formula (5)

-continued

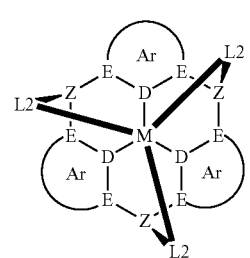
formula (6)

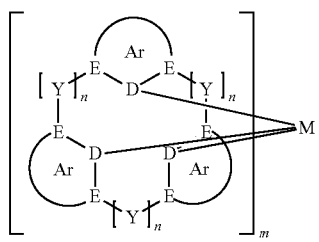
formula (7)

wherein
Y is, identically or differently on each occurrence, an optionally substituted atom selected from C, N or P wherein the substituent, which is optionally present does not coordinate to the metal M;
n is, identically or differently on each occurrence, 0, 1 or 2,
Z is, identically or differently on each occurrence, C⁻, CR¹, N, or P;
R¹ is, identically or differently on each occurrence, R or a group L2;
L2 is, identically or differently on each occurrence, a donor group having 1 to 40 C atoms, which optionally forms a further bond or coordination to M and is optionally substituted by one or more radicals R; and
m is 2, 3, or 4.

10. The electronic device of claim 9, wherein the aryl or heteroaryl group formed by Ar together with the group E-D-E is a group of formulae (8), (9), and (11)-(19), wherein the dashed bonds in each formula indicate the bonds of each group to Y, and wherein * in each case is the position of coordination to M:

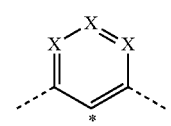
formula (8)

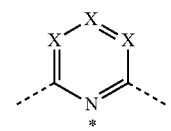
formula (9)

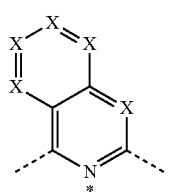
formula (11)

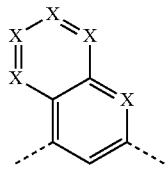
formula (12)

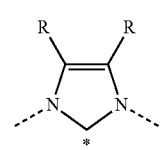
formula (13)

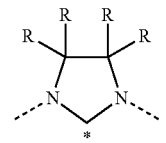
formula (14)

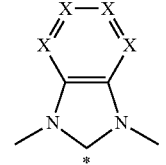
formula (15)

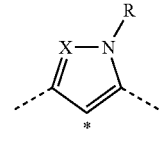
formula (16)

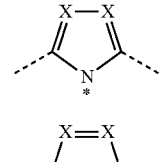
formula (17)

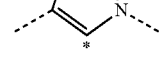
formula (18)

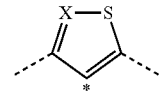
formula (19)

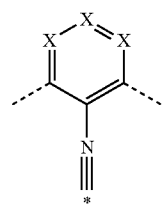
formula (20)

wherein X is, identically or differently on each occurrence, CR or N, with the proviso that a maximum of three X in each group is N;
R is, identically or differently on each occurrence, H, deuterium, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thio-alkoxy group having 1 to 40 C atoms optionally substituted by one or more radicals $R^2$, a straight-chain alkenyl or alkynyl group having 2 to 40 C atoms optionally substituted by one or more radicals $R^2$, a branched or cyclic alkyl, alkenyl, alkynyl, alkoxy, or thioalkoxy group having 3 to 40 C atoms optionally substituted by one or more radicals $R^2$, wherein one or more non-adjacent $CH_2$ groups of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, $SO$, $SO_2$, $NR^2$, O, S, or $CONR^2$, and wherein one or more H atoms of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by F, Cl, Br, I, CN, or $NO_2$, an aromatic or heteroaromatic ring system having 5 to 60 aromatic ring atoms optionally substituted by one or more radicals $R^2$, an aryloxy or heteroaryloxy group having 5 to 60 aromatic ring atoms optionally substituted by one or more radicals $R^2$, a diarylamino group, diheteroarylamino group or arylheteroarylamino group having 10 to 40 aromatic ring atoms optionally substituted by one or more radicals $R^2$, or a combination of these systems; and wherein two or more R optionally define a mono- or polycyclic, aliphatic, aromatic, and/or benzo-fused ring system with one another;

$R^2$ is, identically or differently on each occurrence, H, F, or an aliphatic, aromatic, and/or heteroaromatic radical having 1 to 20 C atoms, wherein one or more H atoms is optionally replaced by F; and wherein two or more $R^2$ optionally define a mono- or polycyclic, aliphatic, or aromatic ring system with one another.

11. The electronic device of claim 1, wherein said electronic device comprises a compound of formula (6a):

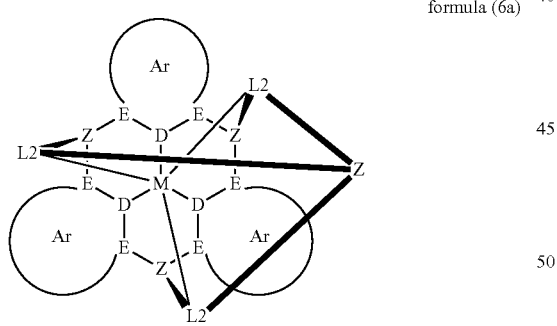

formula (6a)

wherein

Z is, identically or differently on each occurrence, $C^-$, $CR^1$, N, or P;

$R^1$ is, identically or differently on each occurrence, R or a group L2; and

L2 is, identically or differently on each occurrence, a donor group having 1 to 40 C atoms, which optionally forms a further bond or coordination to M and is optionally substituted by one or more radicals R.

12. The electronic device of claim 1, wherein said electronic device comprises at least one compound of formulae (56) to (65):

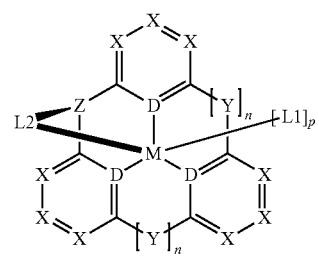

formula (56)

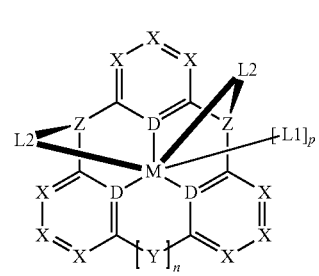

formula (57)

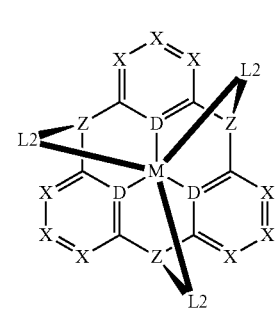

formula (58)

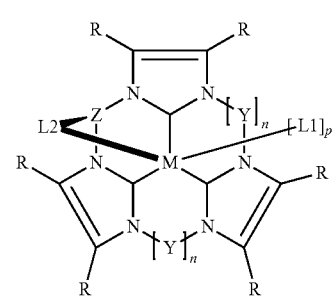

formula (59)

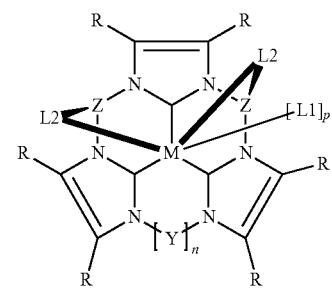

formula (60)

-continued formula (61)
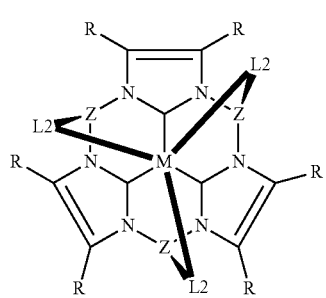

formula (62)
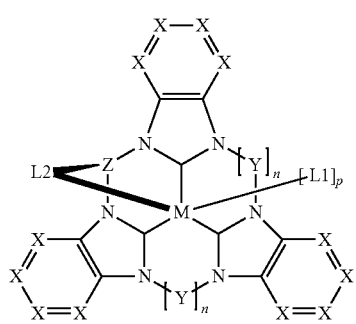

formula (63)
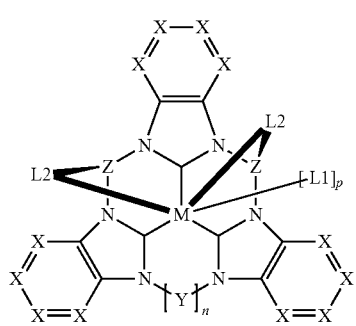

formula (64)
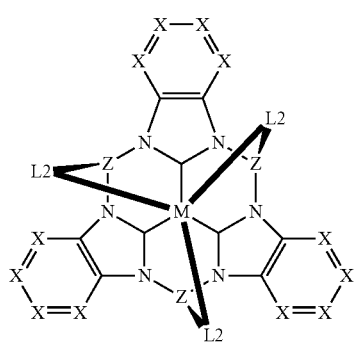

formula (65)
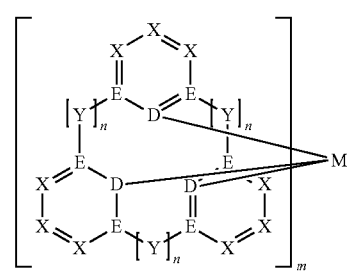

wherein D is, identically or differently on each occurrence, C or N, m is 2, 3, or 4, X is identically or differently on each occurrence, and is CR or N, with the proviso that a maximum of three X in each group stand for N;

Z is, identically or differently on each occurrence, $C^-$, $CR^1$, N, or P;

Y is, identically or differently on each occurrence, an optionally substituted atom selected from C, N or P wherein the substituent, which is optionally present might also be coordinated to the metal M;

$R^1$ is, identically or differently on each occurrence, R or a group L2;

L2 is, identically or differently on each occurrence, a donor group having 1 to 40 C atoms, which optionally forms a further bond or coordination to M and is optionally substituted by one or more radicals R;

R is, identically or differently on each occurrence, H, deuterium, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 40 C atoms optionally substituted by one or more radicals $R^2$, a straight-chain alkenyl or alkynyl group having 2 to 40 C atoms optionally substituted by one or more radicals $R^2$, a branched or cyclic alkyl, alkenyl, alkynyl, alkoxy, or thioalkoxy group having 3 to 40 C atoms optionally substituted by one or more radicals $R^2$, wherein one or more non-adjacent $CH_2$ groups of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$, and wherein one or more H atoms of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by F, Cl, Br, I, CN, or $NO_2$, an aromatic or heteroaromatic ring system having 5 to 60 aromatic ring atoms optionally substituted by one or more radicals $R^2$, an aryloxy or heteroaryloxy group having 5 to 60 aromatic ring atoms optionally substituted by one or more radicals $R^2$, a diarylamino group, diheteroarylamino group or arylheteroarylamino group having 10 to 40 aromatic ring atoms optionally substituted by one or more radicals $R^2$, or a combination of these systems; and wherein two or more R optionally define a mono- or polycyclic, aliphatic, aromatic, and/or benzo-fused ring system with one another; and $R^2$ is, identically or differently on each occurrence, H, F, or an aliphatic, aromatic, and/or heteroaromatic radical having 1 to 20 C atoms, wherein one or more H atoms is optionally replaced by F; and wherein two or more $R^2$ optionally define a mono- or polycyclic, aliphatic, or aromatic ring system with one another.

13. The electronic device of claim 1, wherein

Y is, identically or differently on each occurrence, $C(R^1)^-$, $C(R^1)_2$, $C(=O)$, $C(=NR)$, $N^-$, $NR^1$, $N(R^1)_2^+$, $PR^1$, $P(R^1)_2^+$, or $P(=S)R^1$, $R^1$ is, identically or differently on each occurrence, R or a group L2;

L2 is, identically or differently on each occurrence, a donor group having 1 to 40 C atoms, which optionally forms a further bond or coordination to M and is optionally substituted by one or more radicals R.

14. The electronic device of claim 13, wherein L2 is an aryl or heteroaryl group and is selected from groups of formulae (21) to (49), wherein the dashed bond in each formula indicates the bonds of each group to Y, and wherein * in each case is the position of coordination to M formula (21)

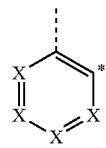

formula (22)

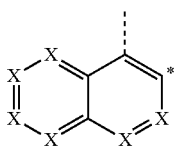

formula (23)

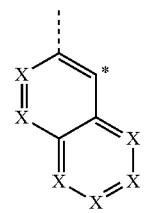

formula (24)

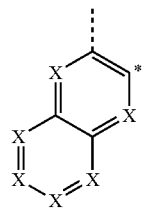

formula (25)

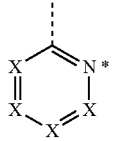

formula (26)

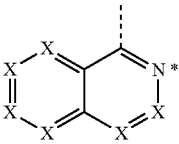

formula (27)

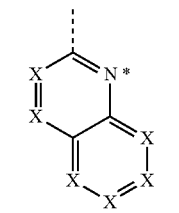

formula (28)

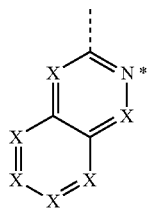

formula (29)

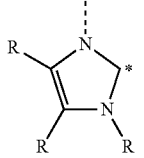

formula (30)

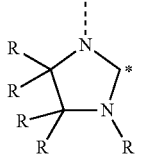

formula (31)

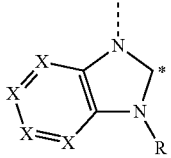

formula (32)

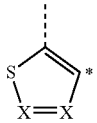

formula (33)

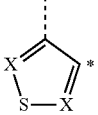

formula (34)

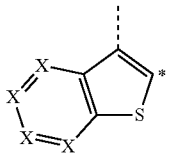

formula (35)

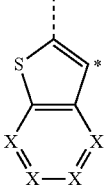

formula (36)

formula (37)
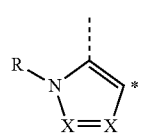

formula (38)
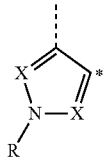

formula (39)
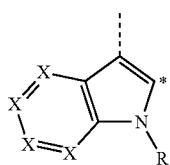

formula (40)
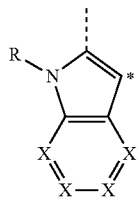

formula (41)
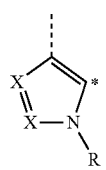

formula (42)
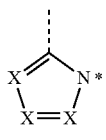

formula (43)
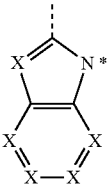

formula (44)
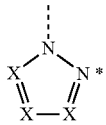

formula (45)
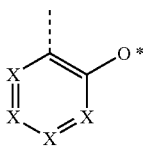

formula (46)
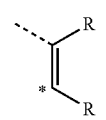

formula (47)
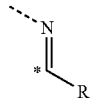

formula (48)
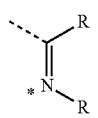

formula (49)
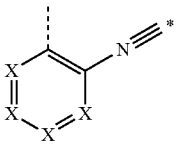

or L2 is a neutral or anionic donor group selected from carbon-containing donor groups which are selected from aliphatic or aromatic acetylides or aliphatic or aromatic isonitriles, nitrogen-containing donor groups of aliphatic amines, aliphatic cyclic amines, nitriles, amides, imides, and imines, each of which are optionally substituted by R, phosphorus-containing donor groups $PF_2$, $P(NR_2)_2$, wherein R is, identically or differently on each occurrence, a $C_1$-$C_{20}$-alkyl group or an aryl or heteroaryl group, alkyl-, aryl-, or mixed alkylarylphosphines, alkylhalo-, arylhalo-, or mixed alkylarylhalophosphines, wherein the halogen in each case is F, Cl, Br, or I, alkyl, aryl or mixed alkyl aryl phosphites or phosphaaromatic compounds, each of which are optionally substituted by R, oxygen-containing donor groups of alcohols, alcoholates, open-chain or cyclic, aliphatic or aromatic ethers, oxygen heterocycles, aldehydes, ketones, phosphine oxide groups, phosphates, phosphonates, borates, silicates, sulfoxide groups, carboxylates, phenols, phenolates, oximes, hydroxamates, β-ketoketonates, β-keto esters and β-diesters, each of which are optionally substituted by R, sulfur-containing donor groups of aliphatic or aromatic thiols and thiolates, open-chain or cyclic thioethers, thiocarbonyl groups, phosphine sulfides and thiocarboxylates, each of which are optionally substituted by R, or bidentate-chelated groups formed from these groups and X is identically or differently on each occurrence, and is CR or N, with the proviso that a maximum of three symbols X in each group stand for N.

15. An electronic device comprising at least one compound of formula (54) or (55)

formula (54)
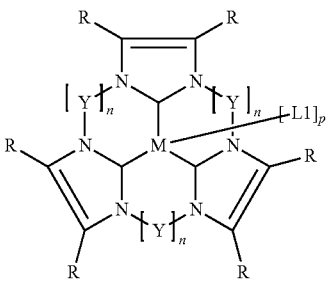

-continued

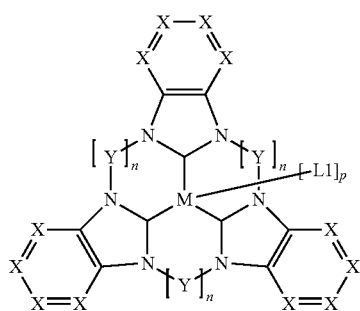

(formula 55)

wherein
X is identically or differently on each occurrence, and is CR or N, with the proviso that a maximum of three X is each group stand for N;
Y is, identically or differently on each occurrence, an optionally substituted atom selected from C, N or P wherein the substituent, which is optionally present might also be coordinated to metal M;
L1 is, identically or differently on each occurrence, a mono-, bi-, tri-, tetra-, penta-, or hexadentate ligand;
n is, identically or differently on each occurrence, 0, 1 or 2,
where n=0 mean that the group Y is not present and a single bond is present;
p is 0, 1, 2, or 3,
M is a transition metal or a main-group metal from the third main group;
R is, identically or differently on each occurrence, H, deuterium, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 40 C atoms optionally substituted by one or more radicals $R^2$, a straight-chain alkenyl or alkynyl group having 2 to 40 C atoms optionally substituted by one or more radicals $R^2$, a branched or cyclic alkyl, alkenyl, alkynyl, alkoxy, or thioalkoxy group having 3 to 40 C atoms optionally substituted by one or more radicals $R^2$, wherein one or more non-adjacent $CH_2$ groups of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$, and wherein one or more H atoms of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by F, Cl, Br, I, CN, or $NO_2$, an aromatic or heteroaromatic ring system having 5 to 60 aromatic ring atoms optionally substituted by one or more radicals $R^2$, an aryloxy or heteroaryloxy group having 5 to 60 aromatic ring atoms optionally substituted by one or more radicals $R^2$, a diarylamino group, diheteroarylamino group or arylheteroarylamino group having 10 to 40 aromatic ring atoms optionally substituted by one or more radicals $R^2$, or a combination of these systems; and wherein two or more R optionally define a mono- or polycyclic, aliphatic, aromatic and/or benzo-fused ring system with one another; and $R^2$ is, identically or differently on each occurrence, H, F or an aliphatic, aromatic and/or heteroaromatic radical having 1 to 20 C atoms, wherein one or more H atoms is optionally replaced by F; and wherein two or more $R^2$ optionally define a mono- or polycyclic, aliphatic, or aromatic ring system with one another.

16. The electronic device of claim 15, wherein said electronic device comprises at least one compound of the formula (54):

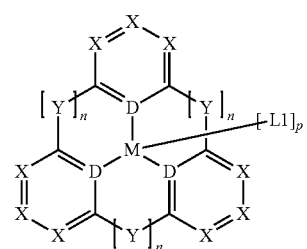

formula (53)

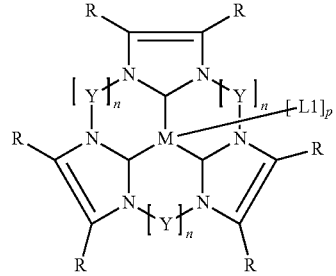

formula (54)

Y is, identically or differently on each occurrence, an optionally substituted atom selected from C, N, or P wherein the substituent, which is optionally present might also be coordinated to the metal M;
R is, identically or differently on each occurrence, H, deuterium, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 40 C atoms optionally substituted by one or more radicals $R^2$, a straight-chain alkenyl or alkynyl group having 2 to 40 C atoms optionally substituted by one or more radicals $R^2$, a branched or cyclic alkyl, alkenyl, alkynyl, alkoxy, or thioalkoxy group having 3 to 40 C atoms optionally substituted by one or more radicals $R^2$, wherein one or more non-adjacent $CH_2$ groups of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$, and wherein one or more H atoms of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by F, Cl, Br, I, CN, or $NO_2$, an aromatic or heteroaromatic ring system having 5 to 60 aromatic ring atoms optionally substituted by one or more radicals $R^2$, an aryloxy or heteroaryloxy group having 5 to 60 aromatic ring atoms optionally substituted by one or more radicals $R^2$, a diarylamino group, diheteroarylamino group or arylheteroarylamino group having 10 to 40 aromatic ring atoms optionally substituted by one or more radicals $R^2$, or a combination of these systems; and wherein two or more R optionally define a mono- or polycyclic, aliphatic, aromatic, and/or benzo-fused ring system with one another; and $R^2$ is, identically or differently on each occurrence, H, F, or an aliphatic, aromatic, and/or heteroaromatic radical having 1 to 20 C atoms, wherein one or more H atoms is optionally replaced by F; and wherein two or more $R^2$ optionally define a mono- or polycyclic, aliphatic, or aromatic ring system with one another.

17. The electronic device of claim 15, wherein said electronic device comprises at least one compound of formula (55)

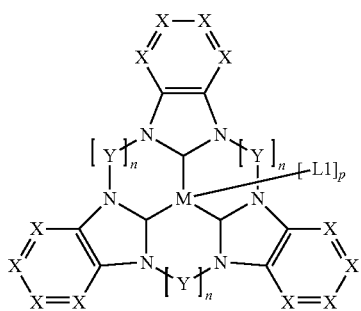

(formula 55)

wherein

X is identically or differently on each occurrence, and is CR or N, with the proviso that a maximum of three X in each group stand for N;

Y is, identically or differently on each occurrence, an optionally substituted atom selected from C, N, or P wherein the substituent, which is optionally present might also be coordinated to the metal M;

R is, identically or differently on each occurrence, H, deuterium, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 40 C atoms optionally substituted by one or more radicals $R^2$, a straight-chain alkenyl or alkynyl group having 2 to 40 C atoms optionally substituted by one or more radicals $R^2$, a branched or cyclic alkyl, alkenyl, alkynyl, alkoxy; or thioalkoxy group having 3 to 40 C atoms optionally substituted by one or more radicals $R^2$, wherein one or more non-adjacent $CH_2$ groups of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by $R^2C=CR^2$, $C=C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$, and wherein one or more H atoms of said straight-chain alkyl, alkoxy, thioalkoxy group, said straight-chain alkenyl or alkynyl group, and said branched or cyclic alkyl, alkenyl, alkynyl, alkoxy, or thioalkoxy group is optionally replaced by F, Cl, Br, I, CN, or $NO_2$, an aromatic or heteroaromatic ring system having 5 to 60 aromatic ring atoms optionally substituted by one or more radicals $R^2$, an aryloxy or heteroaryloxy group having 5 to 60 aromatic ring atoms optionally substituted by one or more radicals $R^2$, a diarylamino group, diheteroarylamino group or arylheteroarylamino group having 10 to 40 aromatic ring atoms optionally substituted by one or more radicals $R^2$, or a combination of these systems; and wherein two or more R optionally define a mono- or polycyclic, aliphatic, aromatic, and/or benzo-fused ring system with one another; and $R^2$ is, identically or differently on each occurrence, H, F, or an aliphatic, aromatic, and/or heteroaromatic radical having 1 to 20 C atoms, wherein one or more H atoms is optionally replaced by F; and wherein two or more $R^2$ optionally define a mono- or polycyclic, aliphatic, or aromatic ring system with one another.

* * * * *